United States Patent
Law et al.

(10) Patent No.: US 10,344,307 B2
(45) Date of Patent: Jul. 9, 2019

(54) PROCESSES FOR THE FORMATION OF FURANDICARBOXYLIC ACID (FDCA) VIA A MULTISTEP BIOCATALYTIC OXIDATION REACTION OF 5-HYDROXYMETHYLFURFURAL (HMF)

(71) Applicant: Biome Bioplastics Limited, Southampton (GB)

(72) Inventors: Paul Law, Southampton (GB); Paul Mines, Southampton (GB); Andrew Carnell, Liverpool (GB); Shane Mckenna, Liverpool (GB)

(73) Assignee: BIOME BIOPLASTICS LIMITED, Southampton (GB)

( * ) Notice: Subject to any disclaimer, the term of this patent is extended or adjusted under 35 U.S.C. 154(b) by 0 days.

(21) Appl. No.: 15/580,261

(22) PCT Filed: Jun. 15, 2016

(86) PCT No.: PCT/EP2016/063757
§ 371 (c)(1),
(2) Date: Dec. 6, 2017

(87) PCT Pub. No.: WO2016/202858
PCT Pub. Date: Dec. 22, 2016

(65) Prior Publication Data
US 2018/0187224 A1    Jul. 5, 2018

(30) Foreign Application Priority Data

Jun. 15, 2015 (GB) .................................. 1510460.7
Apr. 20, 2016 (GB) .................................. 1606898.3
Apr. 20, 2016 (GB) .................................. 1606901.5

(51) Int. Cl.
| | | |
|---|---|---|
| *C08G 63/133* | (2006.01) |
| *C12P 17/04* | (2006.01) |
| *C12P 7/62* | (2006.01) |
| *C08G 63/181* | (2006.01) |
| *C08G 63/199* | (2006.01) |
| *C12N 9/04* | (2006.01) |
| *C08L 67/02* | (2006.01) |

(52) U.S. Cl.
CPC ............ *C12P 17/04* (2013.01); *C08G 63/181* (2013.01); *C08G 63/199* (2013.01); *C08L 67/02* (2013.01); *C12N 9/0006* (2013.01); *C12P 7/625* (2013.01); *C12Y 101/03009* (2013.01); *C12Y 102/01003* (2013.01); *C12Y 106/03001* (2013.01); *C12Y 111/01006* (2013.01); *C12Y 111/01007* (2013.01); *C12Y 117/03002* (2013.01)

(58) Field of Classification Search
USPC ........................................................ 528/302
See application file for complete search history.

(56) References Cited

FOREIGN PATENT DOCUMENTS

| CN | 103483571 | 1/2014 |
| WO | WO 2011/054926 | 5/2011 |
| WO | WO 2012/142605 | 10/2012 |

OTHER PUBLICATIONS

McKenna et al., Enzyme Cascade Reactions; Green Chem., 2015, 17, p. 3271-3275 (Year: 2015).*
Mckenna et al., "Enzyme cascade reactions: synthesis of furandicarboxylic acid (FDCA) and carboxylic acids using oxidases in tandem", Green Chemistry, 2015, 17: 3271-3275.
Mckenna et al., Enzyme cascade reactions: synthesis of furandicarboxylic Acid (FDCA) and Unactivated Carboxylic Acids, Green Chemistry, 2015, pp. 1-27.
Bechi et al., "Catalytic bio-chemo and bio-bio tandem oxidation reactions for amide and carboxylic acid synthesis", Green Chemistry, 2014, 16: 4524-4529.
Escalettes et al., "Directed Evolution of Galactose Oxidase: Generation of Enantioselective Secondary Alcohol Oxidases", ChemBioChem, 2008, 9: 857-860.
Dijkman et al., "Enzyme-Catalyzed Oxidation of 5-Hydroxymethylfurfural to Furan-2,5-dicarboxylic Acid", Angewandte Chemie—International Edition, 2014, 53: 6515-6518.
Zhang et al., "Advances in catalytic production of bio-based polyester monomer 2,5-furandicarboxylic acid derived from lignocellulosic biomass", Carbohydrate Polymers, 2015, 130: 420-428.
Database WPI Week 201431, Thomson Scientific, XP002763731, CN103483571 (Chinese Acad Sci Ningbo Material Technol), abstract, 2014.
Yu et al., "Chemosynthesis and Characterization of Fully Biomass-Based Copolymers of Ethylene Glycol, 2,5-Furandicarboxylic Acid, and Succinic Acid", Journal of Applided Polymer Science, 2013, 130(2): 1415-1420.
Ma et al., "The copolymerization reactivity of diols with 2,5-furandicarboxylic acid for furan-based copolyester materials", Journal of Materials Chemistry, 2012, 22: 3457-3461.

* cited by examiner

*Primary Examiner* — Terressa Boykin
(74) *Attorney, Agent, or Firm* — James S. Keddie; Bozicevic, Field & Francis LLP

(57) ABSTRACT

The present invention relates to processes for the formation of furandicarboxylic acid (FDCA), in particular 2,5-furandicarboxylic acid (2,5-FDCA), and mono- and diester derivatives thereof, via a multistep biocatalytic oxidation reaction of 5-hydroxymethylfurfural (HMF) using, for example, an enzyme selected from the group consisting of xanthine oxidoreductase (XOR), galactose oxidase variant $M_{3-5}$, aldehyde dehydrogenase, and/or ketoreductase. The invention also relates to copolymers that comprise the furandicarboxylic acid monomers and derivatives thereof, processes for the formation of the copolymers and uses for the copolymers.

30 Claims, 24 Drawing Sheets

PROCESSES FOR THE FORMATION OF FURANDICARBOXYLIC ACID (FDCA) VIA A MULTISTEP BIOCATALYTIC OXIDATION REACTION OF 5-HYDROXYMETHYLFURFURAL (HMF)

CROSS-REFERENCE TO RELATED APPLICATIONS

This application is a § 371 national phase of International Application No. PCT/EP2016/063757, filed on Jun. 15, 2016, which claims the benefit of United Kingdom Patent Application No. 1510460.7, filed on Jun. 15, 2015, United Kingdom Patent Application No. 1606898.3, filed on Apr. 20, 2016, and United Kingdom Patent Application No. 1606901.5, filed on Apr. 20, 2016, which applications are incorporated by reference herein.

The present invention relates to new processes for the formation of furandicarboxylic acid (FDCA), in particular 2,5-furandicarboxylic acid (2,5-FDCA), and mono- and diester derivatives thereof, copolymers that comprise furandicarboxylic acid monomers and derivatives thereof, processes for the formation of the copolymers and uses for the copolymers.

Due to their versatility, polymers, such as plastics, have found wide ranging applications in modern society, and can be found in products ranging from carbonated drinks bottles to mobile phones and surgical equipment. PET (polyethylene terephthalate) is one of the most dominant plastics on the market. The annual worldwide production of PET is approximately 53.3 million tonnes, which makes up 18% of global polymer production. However, as PET is highly stable, it is resistant to biodegradation which poses a significant environmental threat. PBAT (polybutylene adipate co-terephthalate) is known to be flexible, tough and most importantly biodegradable. PBAT can be blended with other biodegradable polymers and can potentially be used as substitutes for industry standard plastics, such as PET.

Terephthalic acid (TPA) is a precursor used in the production of PET and PBAT. TPA is manufactured by the oxidation of para-xylene, which is derived from petrochemicals. As oil reserves represent a finite source of petrochemicals, there is considerable interest in the development of bio-based plastics derived from biomass, particularly plastics that are biodegradable.

It is known that 5-hydroxymethylfurfural (HMF) can be derived from cellulose via dehydration of glucose and fructose.

Obtaining 2,5-furandicarboxylic acid from 5-hydroxymethylfurfural requires a six-electron oxidation for which numerous metal catalysts and nanoparticles have been employed, such as Au—$TiO_2$, Au—C modified with Pd, Au-hydrotalicite, Pt—C, Au/$TiO_2$, and Pt/$ZrO_2$. However, these reactions require high pressure and/or temperature and additives that decrease the sustainability of the process considerably.

It has been found by the present inventors that 5-hydroxymethylfurfural can be transformed into 2,5-furandicarboxylic acid in a one-pot multistep biocatalytic reaction using an oxidant, such as oxygen from the air.

Thus, the first aspect of the invention relates to a process for the formation of 2,5-furandicarboxylic acid (2,5-FDCA) from 5-hydroxymethylfurfural (HMF), said process comprising the steps of (i) providing 5-hydroxymethylfurfural; and
(ii) adding xanthine oxidoreductase (XOR) and/or galactose oxidase variant $M_{3-5}$ (GOase $M_{3-5}$).

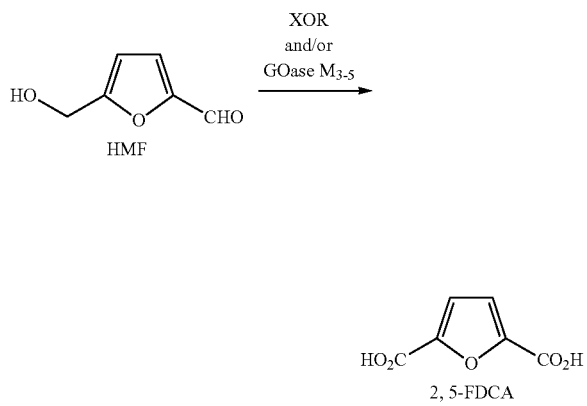

As indicated above, biocatalysts useful in the formation of 2,5-furandicarboxylic acid are galactose oxidase variant $M_{3-5}$ (GOase $M_{3-5}$) and a xanthine oxidoreductase (XOR).

The process therefore encompasses the use of xanthine oxidoreductase (XOR) and/or galactose oxidase variant $M_{3-5}$ (GOase $M_{3-5}$), preferably xanthine oxidoreductase (XOR) and galactose oxidase variant $M_{3-5}$ (GOase $M_{3-5}$).

The xanthine oxidoreductase can be selected from the group consisting of *E. coli* XDH, *Rhodococcus capsulatus* xanthine dehydrogenase (XDH) single variant E232V, and double mutant XDH E232 V/R310, and periplasmic aldehyde oxidase (PaoABC).

In a preferred feature, the xanthine oxidoreductase is periplasmic aldehyde oxidase (PaoABC), which for the purpose of the present invention if preferably obtained from *E. coli*. PaoABC is a 135 kDa heterotrimeric enzyme with a large (78.1 kDa) molybdenum cofactor (Moco)-containing PaoC subunit, a medium (33.9 kDa) FAD-containing PaoB subunit, and a small (21.0 kDa) [2Fe-2S]-containing PaoA subunit.

Scheme A- Conversion of HMF into 2, 5-FDCA using GOase M$_{3-5}$ and XOR.

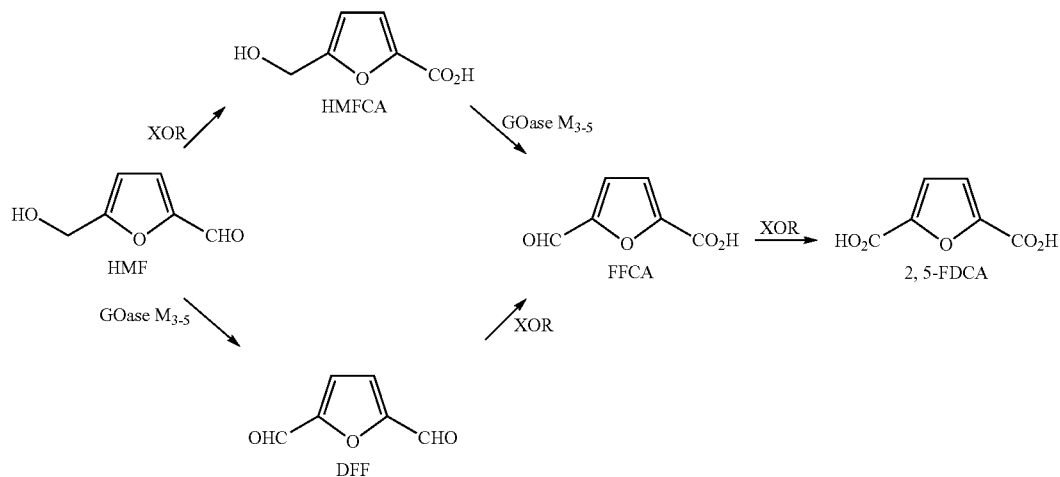

As set out in Scheme A above, 2,5-furandicarboxylic acid (2,5-FDCA) can be produced from 5-hydroxymethylfurfural (HMF) via two different intermediates; diformyl furan (DFF) and formylfurancarboxylic acid (FFCA).

In particular, galactose oxidase variant M$_{3-5}$ can be used to convert 5-hydroxymethylfurfural (HMF) into diformyl furan (DFF). Xanthine oxidoreductase (XOR) can then be used to transform diformyl furan into 2,5-furandicarboxylic acid (2,5-FDCA) via formylfurancarboxylic acid (FFCA).

Alternatively, 2,5-furandicarboxylic acid (2,5-FDCA) can be produced from 5-hydroxymethylfurfural (HMF) via two different intermediates; hydroxymethyl furancarboxylic acid (HMFCA) and formylfurancarboxylic acid (FFCA). In particular, 5-hydroxymethylfurfural (HMF) can be converted into hydroxymethyl furancarboxylic acid (HMFCA) using xanthine oxidoreductase (XOR). The formylfurancarboxylic acid (FFCA) may be then formed from hydroxymethyl furancarboxylic acid (HMFCA) using galactose oxidase variant M$_{3-5}$ (GOase M$_{3-5}$). The present invention encompasses both of these routes to 2,5-furandicarboxylic acid (2,5-FDCA).

The oxidation reaction set out in Scheme A and using galactose oxidase variant M$_{3-5}$ and xanthine oxidoreductase (XOR) are carried out in the presence of an oxidant. Preferably the oxidant includes, but is not limited to, air. Alternative or additional oxidants include oxygen (O$_2$) and DCPIP (2,6-dichloro-4-[(4-hydroxyphenyl)imino]cyclohexa-2,5-dien-1-one).

The molybdenum-dependent xanthine oxidoreductase (XOR) enzymes, commercially available E. coli XDH, Rhodococcus capsulatus xanthine dehydrogenase (XDH) single variant E232V and double mutant XDH E232 V/R310, and periplasmic aldehyde oxidase can be used to oxidise substrates 5-hydroxymethylfurfural (HMF), diformyl furan (DFF) and formylfurancarboxylic acid (FFCA) with oxygen from the air as the oxidant. An exogenous electron acceptor, such as DCPIP (2,6-dichloro-4-[(4-hydroxyphenyl)imino]cyclohexa-2,5-dien-1-one) can be used increase the rate of oxidation. Periplasmic aldehyde oxidase can oxidise 5-hydroxymethylfurfural, diformyl furan and formylfurancarboxylic acid, and is therefore the preferred biocatalyst for the aldehyde oxidation step.

The first aspect of the present application therefore further relates to a process for the formation of 2,5-furandicarboxylic acid (2,5-FDCA) comprising the steps of (i) converting 5-hydroxymethylfurfural (HMF) into formylfurancarboxylic acid (FFCA); and (ii) converting formylfurancarboxylic acid into 2,5-furandicarboxylic acid (2,5-FDCA), wherein steps (i) and (ii) are carried out in the presence of xanthine oxidoreductase (XOR) and galactose oxidase variant M$_{3-5}$ (GOase M$_{3-5}$).

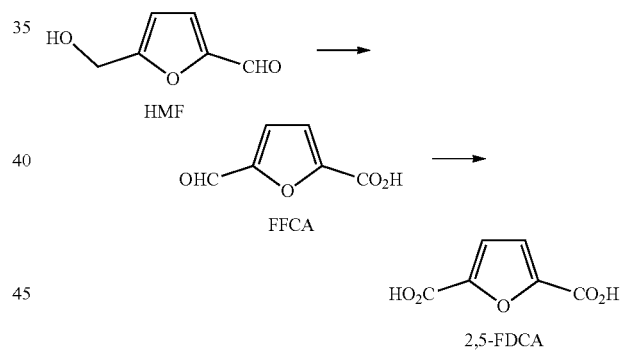

The xanthine oxidoreductase (XOR) and galactose oxidase variant M$_{3-5}$ (GOase M$_{3-5}$) enzymes can be added simultaneously or sequentially.

The first aspect of the present application further relates to a process for the production of 2,5-furandicarboxylic acid (2,5-FDCA) comprising the steps of (i) converting 5-hydroxymethylfurfural (HMF) into diformyl furan (DFF);

(ii) converting diformyl furan (DFF) into formylfurancarboxylic acid (FFCA); and (iii) converting formylfurancarboxylic acid (FFCA) into 2,5-furandicarboxylic acid (2,5-FDCA)

wherein steps (i), (ii) and (iii) are carried out in the presence of xanthine oxidoreductase (XOR) and/or galactose oxidase variant M$_{3-5}$ (GOase M$_{3-5}$).

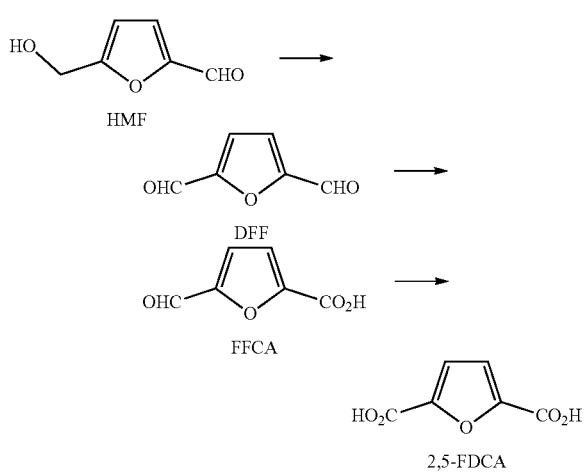

The xanthine oxidoreductase (XOR) and galactose oxidase variant $M_{3-5}$ (GOase $M_{3-5}$) enzymes can be added simultaneously or sequentially.

In a preferred feature of the first aspect, the galactose oxidase variant $M_{3-5}$ (GOase $M_{3-5}$) is added to the 5-hydroxymethylfurfural (HMF) to produce diformyl furan (DFF), followed by the addition of xanthine oxidoreductase (XOR) to produce 2,5-furandicarboxylic acid (2,5-FDCA) via formylfurancarboxylic acid (FFCA).

Thus, in a further feature of the first aspect of the invention the process comprises the steps of
(i) providing 5-hydroxymethylfurfural;
(ii) adding galactose oxidase variant $M_{3-5}$ (GOase $M_{3-5}$) to convert 5-hydroxymethylfurfural to diformyl furan (DFF);
(iii) adding xanthine oxidoreductase (XOR), preferably periplasmic aldehyde oxidase (PaoABC), to convert the diformyl furan to 2,5-furandicarboxylic acid (2,5-FDCA) via formylfurancarboxylic acid (FFCA)

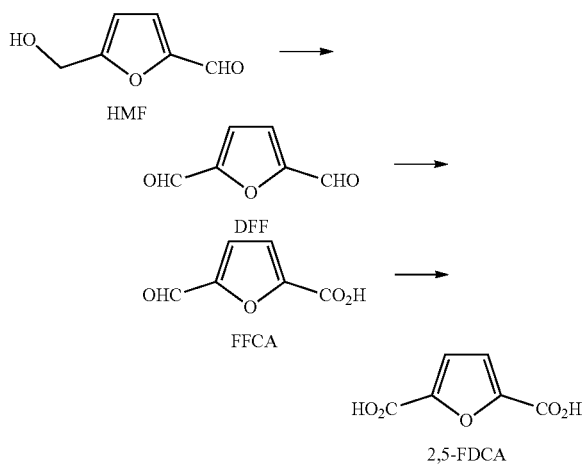

It is preferable that at least about 50%, such as at least about 70%, preferably at least about 80%, more preferably at least about 90%, and most preferably about 100% of 5-hydroxymethylfurfural (HMF) is converted into diformyl furan (DFF) in step (ii) before xanthine oxidoreductase (XOR), preferably periplasmic aldehyde oxidase (PaoABC), is added in step (iii). The amount of 5-hydroxymethylfurfural and diformyl furan present in the process can be determined by reverse-phase high pressure liquid chromatography (RP-HPLC).

The formation of 2,5-furandicarboxylic acid (2,5-FDCA) from 5-hydroxymethylfurfural (HMF) via diformyl furan (DFF) and formylfurancarboxylic acid is favoured by using a sequential, stepwise process in which the galactose oxidase variant $M_{3-5}$ (GOase $M_{3-5}$) catalysed conversion of 5-hydroxymethylfurfural (HMF) to diformyl furan (DFF) is allowed to run to completion prior to addition of the xanthine oxidoreductase (XOR), preferably periplasmic aldehyde oxidase enzyme (PaoABC). This stepwise reaction can furnish 2,5-furandicarboxylic acid (2,5-FDCA) as the only oxidation product, cleanly and with 100% conversion.

Oxidases, such as galactose oxidase variant $M_{3-5}$ (GOase $M_{3-5}$) and xanthine oxidoreductase (XOR), preferably periplasmic aldehyde oxidase (PaoABC), produce $H_2O_2$ as a by-product. It is therefore advantageous to remove the $H_2O_2$ from the reaction using catalase. Catalase protects the enzymes from oxidative damage. A further advantage of incorporating catalase in the reaction is that it converts $H_2O_2$ into $O_2$ thus providing a source of $O_2$ that may be used as the oxidant in the reaction. The catalase may be provided in a mass ratio of from about 1:100 to about 1:1, such as from 1:75 to about 1:20, for instance from about 1:50 to about 1:30 with respect to the 5-hydroxymethylfurfural (HMF). Additional catalase can be added to the reaction as required.

Thus, each of the processes of the present invention additionally comprise the addition of catalase in combination with the galactose oxidase variant $M_{3-5}$ (GOase $M_{3-5}$) and/or xanthine oxidoreductase (XOR), preferably periplasmic aldehyde oxidase (PaoABC). The catalase can be added simultaneously, sequentially or separately to the oxidase enzymes.

It is advantageous to use sufficient buffer capacity to control the pH of the reaction and to drive the reaction to completion. For instance, the pH for the conversion of diformyl furan (DFF) to 2,5-furandicarboxylic acid (2,5-FDCA) using periplasmic aldehyde oxidase (PaoABC) at substrate concentrations of about 100 nM can drop, i.e. to less than 5, which is below the optimum pH of between 6 to 8. Any suitable buffer can be used in the reaction. Particularly useful buffers are phosphate buffers, such as a potassium phosphate buffer.

Thus, each of the processes of the present invention is preferably carried out in a buffered reaction mixture with a pH of 6 to 8. Preferably the reaction mixture is buffered with a phosphate buffer, more preferably potassium phosphate buffer. The pH may be determined by any known means. It is preferred that the pH is determined using a pH meter and a probe.

In the first aspect of the invention, the 5-hydroxymethylfurfural may be provided in a solution in step (i), preferably an aqueous solution. Preferably, 5-hydroxymethylfurfural may be provided in a solution at a concentration of from about 1 mM to about 1,000 mM, such as from about 10 mM to about 750 mM, for instance from about 50 mM to about 500 mM.

Each of the biocatalytic processes of the present invention can be conducted at any suitable temperature. Those skilled in the art will understand that a suitable temperature for such enzymatic processes may be from 0° C. to about 60° C., such as from about 20° C. to about 50° C., for instance from about 30° C. to about 40° C. It is particularly preferred that the processes of the present invention are carried out at about 37° C. The temperature may be maintained by any suitable means, for instance using a shaking incubator. This has the advantage of agitating the reaction whilst maintaining the suitable temperature.

2,5-Furandicarboxylic acid (2,5-FDCA) can be isolated by a range of means, for instance by heat treatment of the reaction solution to precipitate the protein, followed by centrifugation, acidification and filtration.

In view of the above, 2,5-furandicarboxylic acid (2,5-FDCA) may be formed from 5-hydroxymethylfurfural (HMF), preferably using the above biocatalysts.

For the purpose of this invention, the 5-hydroxymethylfurfural (HMF) may be formed from glucose and fructose. The glucose and fructose is preferably obtained from lignocelluloses. Such transformations are well known to those skilled in the art.

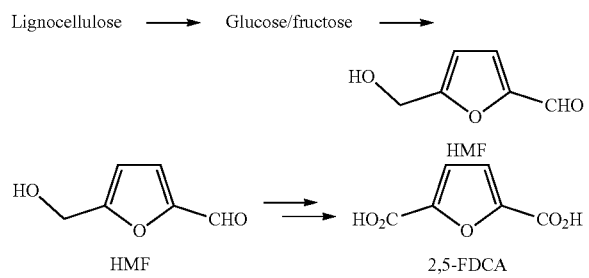

The present invention therefore provides a novel biocatalytic route to 2,5-furandicarboxylic acid (2,5-FDCA) from renewable feedstocks, such as lignocellulose, highlighting the opportunity for bioconversion of lignocellulose into aromatic products using biotechnology.

Since lignocellulose is an abundant, inexpensive and sustainable resource, it may be possible to combine this technology with existing industrial processes in order to generate value-added products from lignocellulose streams.

For example, formylfurancarboxylic acid (FFCA) may be formed from 5-hydroxymethylfurfural (HMF) using galactose oxidase variant $M_{3-5}$ (GOase $M_{3-5}$) and xanthine oxidoreductase (XOR), such as periplasmic aldehyde oxidase (PaoABC), via hydroxymethyl furancarboxylic acid (HMFCA) or diformyl furan (DFF), as described above. The 5-hydroxymethylfurfural (HMF) can be formed from glucose and/or fructose, which may in turn be derived from lignocellulose.

The present invention therefore encompasses the production of formylfurancarboxylic acid (FFCA) by conversion of 5-hydroxymethylfurfural (HMF) to hydroxymethyl furancarboxylic acid (HMFCA)

The biocatalyst of the present invention can be produced in a purified or partially purified form or as a component of a cell lysate. Alternatively, the production of 2,5-furandicarboxylic acid (2,5-FDCA) can be catalysed by using a suitable naturally occurring or modified bacterium which includes the required biocatalysts.

In a second aspect of the invention, there is provided a process for the formation of 2,5-furandicarboxylic acid (2,5-FDCA) from 5-hydroxymethylfurfural (HMF), said process comprising the steps of
  (i) providing 5-hydroxymethylfurfural; and
  (ii) adding galactose oxidase variant $M_{3-5}$ (GOase $M_{3-5}$), xanthine oxidoreductase (XOR), preferably periplasmic aldehyde oxidase (PaoABC), and horseradish peroxidase (HRP) to the 5-hydroxymethylfurfural.

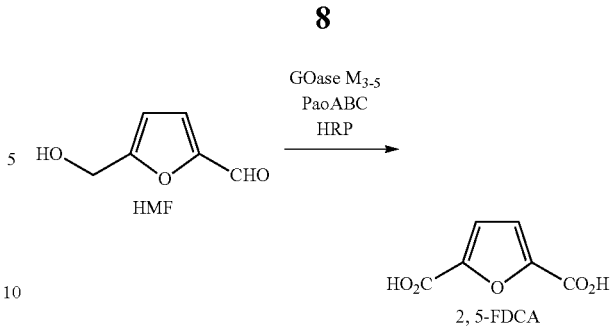

The horseradish peroxidase may be added in step (ii) in an amount of from about 1 to about 400 mol %, such as from about 5 to about 100 mol %, preferably from about 10 to about 50 mol %, based on the amount of 5-hydroxymethylfurfural provided in step (i).

Alternatively, there is provided a process for the formation of 2,5-furandicarboxylic acid (2,5-FDCA) from 5-hydroxymethylfurfural (HMF), said process comprising the steps of
  (i) providing 5-hydroxymethylfurfural; and
  (ii) adding galactose oxidase variant $M_{3-5}$ (GOase $M_{3-5}$), xanthine oxidoreductase (XOR), preferably periplasmic aldehyde oxidase (PaoABC), and a metal complex to the 5-hydroxymethylfurfural.

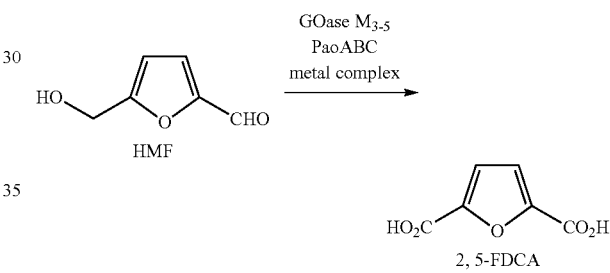

Preferred metal complexes include those comprising a transition metal. Of the transition metals, vanadium, manganese, iron and cobalt are preferred. The metal may be in any oxidation state. The oxidation states (I), (II), (III), (IV), and (V) are preferred. Any complex of the metal may be used. The term "complex" includes salts and macrocycles within its definition. Suitable salts include acetate, alkoxide, oxide, sulphate, and halide. Acac, $OEt_3$, oxide, sulphate, and phthalocyanine complexes are preferred, with oxide and sulphate complexes particularly preferred. Exemplary metal complexes include V(II)acac, V(V)$OEt_3$, V(V)oxide, Vanadyl acac, VO(IV)sulphate, Mn(III)acac, Mn(II)sulphate, Fe(II)phthalocyanine, Fe(III)acac, Fe(III)EDTA, Fe(III)oxide, Co(II,III)oxide, hematin, and hemin, of which V(V)oxide and VO(IV)sulphate are preferred. VO(IV)sulphate is particularly preferred. Those skilled in the art will appreciate that acac is acetylacetone.

The metal complexes may be added in step (ii) in an amount of from about 1 to about 400 mol %, such as from about 5 to about 100 mol %, preferably from about 10 to about 50 mol %, based on the amount of 5-hydroxymethylfurfural provided in step (i).

It will be understood that each of the processes of the second aspect of the invention is a one-pot process whereby the 5-hydroxymethylfurfural is converted into 2,5-furandicarboxylic acid by successive reactions in a single reactor and without separating or purifying any intermediate compounds.

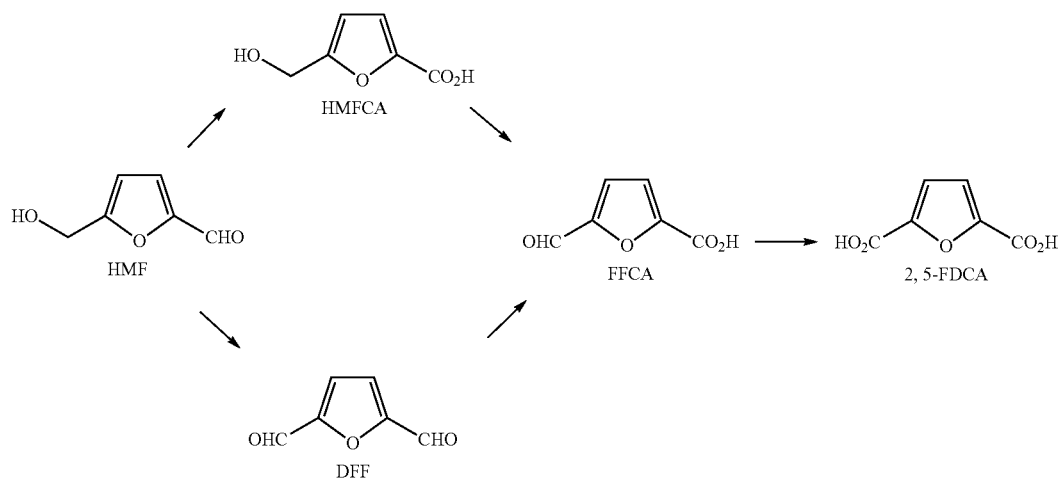

Thus, for example, the 2,5-furandicarboxylic acid can be produced via hydroxymethyl furancarboxylic acid (HMFCA) diformyl furan (DFF) and/or formylfurancarboxylic acid (FFCA) as illustrated above.

In step (ii) of the processes of the second aspect of the invention, the enzymes galactose oxidase variant $M_{3-5}$ (GOase $M_{3-5}$), xanthine oxidoreductase (XOR), preferably periplasmic aldehyde oxidase (PaoABC), and either horseradish peroxidase (HRP) or metal complex are added to the unreacted 5-hydroxymethylfurfural.

The term "unreacted 5-hydroxymethylfurfural" refers to the 5-hydroxymethylfurfural provided in step (i) and means that at least about 90%, such as at least about 95%, preferably at least about 99%, most preferably about 100% of 5-hydroxymethylfurfural is present, based upon the amount of HMF provided in step (i). The amount of 5-hydroxymethylfurfural present in the process can be determined by RP-HPLC. The skilled person will understand that galactose oxidase variant $M_{3-5}$, xanthine oxidoreductase (XOR), preferably periplasmic aldehyde oxidase, and either horseradish peroxidase or metal complex may be added in step (ii) simultaneously and/or sequentially and in any order. This includes adding one or more of, such as two or more of, for example all three of, galactose oxidase variant $M_{3-5}$, xanthine oxidoreductase (XOR), preferably periplasmic aldehyde oxidase, and either horseradish peroxidase or metal complex, as a mixture or separately, and then adding the remaining galactose oxidase variant $M_{3-5}$, xanthine oxidoreductase (XOR), preferably periplasmic aldehyde oxidase, and/or either horseradish peroxidase or metal complex.

It is preferred that catalase is provided in step (i) and/or step (ii) of the processes of the second aspect of the invention. The catalase may be provided in a mass ratio of from about 1:100 to about 1:1, such as from 1:75 to about 1:20, for instance from about 1:50 to about 1:30 with respect to the 5-hydroxymethylfurfural. Additional catalase can be added to the reaction as required.

As discussed in relation to the first aspect of the invention, buffer may be provided as part of each of the processes of the second aspect of the invention, to maintain a pH of from about 6 to about 8 in the process. Preferably, the buffer is added in step (ii). Any suitable buffer can be used in the reaction. Particularly useful buffers are phosphate buffers, such as a potassium phosphate buffer.

Thus, each of the processes of the present invention is preferably carried out in a buffered reaction mixture with a pH of 6 to 8. Preferably the reaction mixture is buffered with a phosphate buffer, more preferably potassium phosphate buffer. The pH may be determined by any known means. It is preferred that the pH is determined using a pH meter and a probe.

In the second aspect of the invention, the 5-hydroxymethylfurfural may be provided in a solution in step (i), preferably an aqueous solution. Preferably, 5-hydroxymethylfurfural may be provided in a solution at a concentration of from about 1 mM to about 1,000 mM, such as from about 10 mM to about 750 mM, for instance from about 50 mM to about 500 mM.

Each of the processes of the second aspect of the invention can be conducted at any suitable temperature. Suitable temperatures for the process may be from 0° C. to about 60° C., such as from about 20° C. to about 50° C., for instance from about 30° C. to about 40° C. It is particularly preferred that step (ii) is carried out at about 37° C. The temperature may be maintained by any suitable means, for instance using a shaking incubator.

2,5-Furandicarboxylic acid (2,5-FDCA) can be isolated by a range of means, for instance by heat treatment of the reaction solution to precipitate the protein, followed by centrifugation, acidification and filtration.

As discussed for the first aspect of the invention, the 5-hydroxymethylfurfural (HMF) may be prepared from glucose and/or fructose. The glucose and fructose may be formed from lignocelluloses.

The biocatalyst of the present invention can be produced in a purified or partially purified form or as a component of a cell lysate. Alternatively, the production of 2,5-furandicarboxylic acid (2,5-FDCA) can be catalysed by using a suitable naturally occurring or modified bacterium which includes the required biocatalysts.

The third aspect of the invention relates to a process for the formation of 2,5-furandicarboxylic acid as set out in the processes of the first and second aspects of the invention, where the xanthine oxidoreductase (XOR) is replaced with aldehyde dehydrogenase (ALD), nicotinamide oxidase (NOX) and either nicotinamide adenine dinucleotide phosphate (NADP$^+$) or nicotinamide adenine dinucleotide (NAD$^+$). All preferred features of the first and second aspects relate to the processes of the third aspect of the invention.

The third aspect of the invention therefore provides a process for the formation of 2,5-furandicarboxylic acid (2,5-FDCA) from 5-hydroxymethylfurfural (HMF), said process comprising the steps of
(i) providing 5-hydroxymethylfurfural; and
(ii) adding galactose oxidase variant $M_{3-5}$ (GOase $M_{3-5}$), aldehyde dehydrogenase (ALD), nicotinamide oxidase (NOX) and either nicotinamide adenine dinucleotide phosphate ($NADP^+$) or nicotinamide adenine dinucleotide ($NAD^+$).

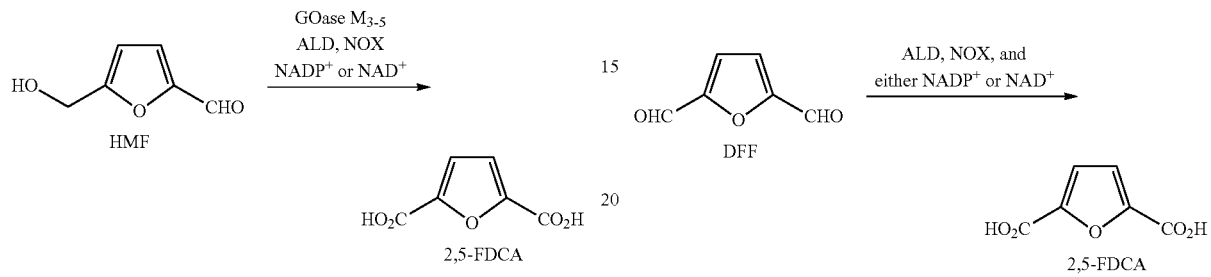

The third aspect of the invention further provides a process for the formation of hydroxymethyl furancarboxylic acid (HMFCA) from 5-hydroxymethylfurfural (HMF) comprising the steps of
(i) providing 5-hydroxymethylfurfural; and
(ii) adding aldehyde dehydrogenase (ALD), nicotinamide oxidase (NOX) and either nicotinamide adenine dinucleotide phosphate ($NADP^+$) or nicotinamide adenine dinucleotide ($NAD^+$).

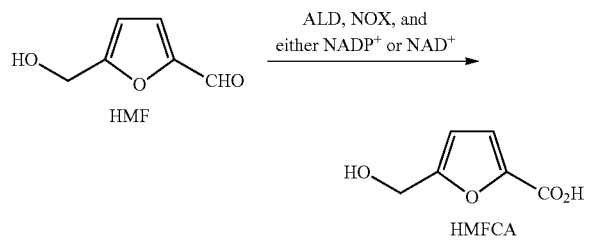

It will be understood that the process is a one-pot process whereby the 5-hydroxymethylfurfural (HMF) is converted into hydroxymethyl furancarboxylic acid (HMFCA) in a single reactor and without separating or purifying any intermediate compounds.

In step (ii), the aldehyde dehydrogenase (ALD), nicotinamide oxidase (NOX) and either nicotinamide adenine dinucleotide phosphate ($NADP^+$) or nicotinamide adenine dinucleotide ($NAD^+$) are added to the unreacted 5-hydroxymethylfurfural.

The term "unreacted 5-hydroxymethylfurfural" refers to the 5-hydroxymethylfurfural provided in step (i) and means that at least about 90%, such as at least about 95%, preferably at least about 99%, most preferably about 100% of 5-hydroxymethylfurfural is present, based upon the amount of 5-hydroxymethylfurfural provided in step (i).

In step (ii), ALD, NOX and either $NADP^+$ or $NAD^+$ are added to the unreacted HMF. The skilled person will understand that ALD, NOX and either $NADP^+$ or $NAD^+$ may be added in step (ii) simultaneously and/or sequentially and in any order. This includes adding one or more of, such as two or more of, for example all three of, NOX, ALD and either $NADP^+$ or $NAD^+$, as a mixture or separately, and then adding the remaining NOX, ALD and either $NADP^+$ or $NAD^+$.

The third aspect of the invention further provides a process for the formation of 2,5-furandicarboxylic acid (2,5-FDCA) from diformyl furan (DFF) comprising the steps of
(i) providing diformyl furan; and
(ii) adding aldehyde dehydrogenase (ALD), nicotinamide oxidase (NOX) and either nicotinamide adenine dinucleotide phosphate ($NADP^+$) or nicotinamide adenine dinucleotide ($NAD^+$).

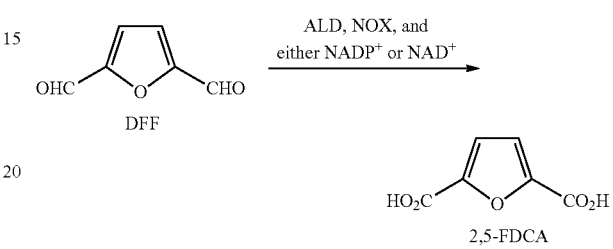

It will be understood that the process is a one-pot process whereby the diformyl furan (DFF) is converted into 2,5-furandicarboxylic acid (2,5-FDCA) in a single reactor and without separating or purifying any intermediate compounds. In step (ii), the aldehyde dehydrogenase (ALD), nicotinamide oxidase (NOX) and either nicotinamide adenine dinucleotide phosphate ($NADP^+$) or nicotinamide adenine dinucleotide ($NAD^+$) are added to the unreacted 5-hydroxymethylfurfural.

The term "unreacted diformyl furan (DFF)" refers to the diformyl furan (DFF) provided in step (i) and means that at least about 90%, such as at least about 95%, preferably at least about 99%, most preferably about 100% of 5-hydroxymethylfurfural is present, based upon the amount of diformyl furan (DFF) provided in step (i).

In step (ii), ALD, NOX and either $NADP^+$ or $NAD^+$ are added to the unreacted HMF. The skilled person will understand that ALD, NOX and either $NADP^+$ or $NAD^+$ may be added in step (ii) simultaneously and/or sequentially and in any order. This includes adding one or more of, such as two or more of, for example all three of, NOX, ALD and either $NADP^+$ or $NAD^+$, as a mixture or separately, and then adding the remaining NOX, ALD and either $NADP^+$ or $NAD^+$.

In a feature of the third aspect of the invention the process comprises the steps of
(i) providing 5-hydroxymethylfurfural;
(ii) adding galactose oxidase variant $M_{3-5}$ (GOase $M_{3-5}$) to convert the 5-hydroxymethylfurfural to diformyl furan (DFF); then
(iii) adding aldehyde dehydrogenase (ALD), nicotinamide oxidase (NOX) and either nicotinamide adenine dinucleotide phosphate ($NADP^+$) or nicotinamide adenine dinucleotide ($NAD^+$) to the diformyl furan in step (ii) to convert the diformyl furan to 2,5-furandicarboxylic acid via formylfurancarboxylic acid (FFCA).

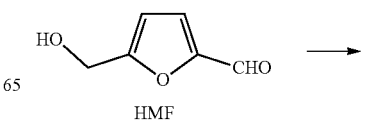

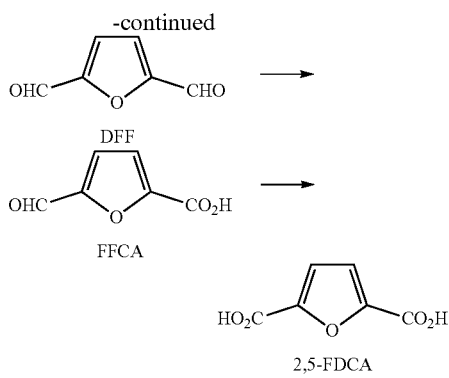

It will be understood that the process is a one-pot process whereby the 5-hydroxymethylfurfural (HMF) is converted into 2,5-furandicarboxylic acid (2,5-FDCA) in a single reactor and without separating or purifying any intermediate compounds.

It is preferable that at least about 50%, such as at least about 70%, preferably at least about 80%, more preferably at least about 90%, and most preferably about 100% of 5-hydroxymethylfurfural (HMF) is converted into diformyl furan (DFF) in step (ii) before aldehyde dehydrogenase (ALD), nicotinamide oxidase (NOX) and either nicotinamide adenine dinucleotide phosphate ($NADP^+$) or nicotinamide adenine dinucleotide ($NAD^+$) is added in step (iii). The amount of 5-hydroxymethylfurfural and diformyl furan present in the process can be determined by reverse-phase high pressure liquid chromatography (RP-HPLC).

In a further feature of the third aspect of the invention there is provided a process for the formation of 2,5-furandicarboxylic acid (2,5-FDCA) from 5-hydroxymethylfurfural (HMF), said process comprising the steps of
(i) providing 5-hydroxymethylfurfural; and
(ii) adding galactose oxidase variant $M_{3-5}$ (GOase $M_{3-5}$), horseradish peroxidase (HRP), aldehyde dehydrogenase (ALD), nicotinamide oxidase (NOX) and either nicotinamide adenine dinucleotide phosphate ($NADP^+$) or nicotinamide adenine dinucleotide ($NAD^+$).

It will be understood that the process is a one-pot process whereby the 5-hydroxymethylfurfural (HMF) is converted into 2,5-furandicarboxylic acid (2,5-FDCA) in a single reactor and without separating or purifying any intermediate compounds.

In step (ii), the aldehyde dehydrogenase (ALD), nicotinamide oxidase (NOX) and either nicotinamide adenine dinucleotide phosphate ($NADP^+$) or nicotinamide adenine dinucleotide ($NAD^+$) are added to the unreacted 5-hydroxymethylfurfural.

The term "unreacted 5-hydroxymethylfurfural" refers to the 5-hydroxymethylfurfural provided in step (i) and means that at least about 90%, such as at least about 95%, preferably at least about 99%, most preferably about 100% of 5-hydroxymethylfurfural is present, based upon the amount of 5-hydroxymethylfurfural provided in step (i). In step (ii), ALD, NOX and either $NADP^+$ or $NAD^+$ are added to the unreacted HMF. The skilled person will understand that ALD, NOX and either $NADP^+$ or $NAD^+$ may be added in step (ii) simultaneously and/or sequentially and in any order. This includes adding one or more of, such as two or more of, for example all three of, NOX, ALD and either $NADP^+$ or $NAD^+$, as a mixture or separately, and then adding the remaining NOX, ALD and either $NADP^+$ or $NAD^+$.

The horseradish peroxidase is as defined in the second aspect of the invention and all preferred features of the second aspect of the invention relate to this process.

In another feature of the third aspect, there is provided a process for the formation of 2,5-furandicarboxylic acid (2,5-FDCA) from 5-hydroxymethylfurfural (HMF), said process comprising the steps of
(i) providing 5-hydroxymethylfurfural; and
(ii) adding galactose oxidase variant $M_{3-5}$ (GOase $M_{3-5}$), a metal complex, aldehyde dehydrogenase (ALD), nicotinamide oxidase (NOX) and either nicotinamide adenine dinucleotide phosphate ($NADP^+$) or nicotinamide adenine dinucleotide ($NAD^+$).

It will be understood that the process is a one-pot process whereby the 5-hydroxymethylfurfural (HMF) is converted into 2,5-furandicarboxylic acid (2,5-FDCA) in a single reactor and without separating or purifying any intermediate compounds.

In step (ii), the aldehyde dehydrogenase (ALD), nicotinamide oxidase (NOX) and either nicotinamide adenine dinucleotide phosphate ($NADP^+$) or nicotinamide adenine dinucleotide ($NAD^+$) are added to the unreacted 5-hydroxymethylfurfural.

The term "unreacted 5-hydroxymethylfurfural" refers to the 5-hydroxymethylfurfural provided in step (i) and means that at least about 90%, such as at least about 95%, preferably at least about 99%, most preferably about 100% of 5-hydroxymethylfurfural is present, based upon the amount of 5-hydroxymethylfurfural provided in step (i). In step (ii), ALD, NOX and either $NADP^+$ or $NAD^+$ are added to the unreacted HMF. The skilled person will understand that ALD, NOX and either $NADP^+$ or $NAD^+$ may be added in step (ii) simultaneously and/or sequentially and in any order. This includes adding one or more of, such as two or more of, for example all three of, NOX, ALD and either $NADP^+$ or $NAD^+$, as a mixture or separately, and then adding the remaining NOX, ALD and either $NADP^+$ or $NAD^+$.

The metal complex is as defined in the second aspect of the invention and all preferred features of the second aspect of the invention relate to the process of the third aspect of the invention.

When $NADP^+$ is present in the reaction, it is preferred that the nicotinamide oxidase (NOX) is nicotinamide oxidase 1 (NOX-1). When $NAD^+$ is present in the reaction, it is preferred that the NOX is nicotinamide oxidase 9 (NOX-9).

Nicotinamide oxidase is preferably provided in step (ii) in an amount of from about 50 weight % to about 180 weight %, such as from about 60 to about 150 weight %, preferably from about 65 weight % to about 140 weight %, based upon the amount of aldehyde dehydrogenase.

$NADP^+$ or $NAD^+$ may be added in step (ii) in an amount of from about 5 mol % to about 50 mol %, such as from about 10 mol % to about 30 mol %, preferably about 20 mol %, based upon the amount of 5-hydroxymethylfurfural provided in step (i).

It is preferred that catalase is provided in step (i) and/or step (ii). The catalase may be provided in a mass ratio of from about 1:100 to about 1:1, such as from 1:75 to about 1:20, for instance from about 1:50 to about 1:30 with respect to the HMF. Additional catalase can be added to the reaction as required.

Thus, each of the processes of the third aspect of the present invention additionally comprise the addition of catalase in combination with the galactose oxidase variant $M_{3-5}$ (GOase $M_{3-5}$) and/or aldehyde dehydrogenase (ALD), nicotinamide oxidase (NOX) and either nicotinamide adenine dinucleotide phosphate ($NADP^+$) or nicotinamide adenine dinucleotide (NAD+). The catalase can be added simultaneously, sequentially or separately to the oxidase enzymes.

It is advantageous to use sufficient buffer capacity to control the pH of the reaction and to drive the reaction to completion. Preferably the optimum pH of the reaction is from pH 6 to pH 8. Any suitable buffer can be used in the reaction. Particularly useful buffers are phosphate buffers, such as a potassium phosphate buffer.

Thus, each of the processes of the present invention is preferably carried out in a buffered reaction mixture with a pH of 6 to 8. Preferably the reaction mixture is buffered with a phosphate buffer, more preferably potassium phosphate buffer. The pH may be determined by any known means. It is preferred that the pH is determined using a pH meter and a probe.

The processes of the third aspect of the invention can be conducted at any suitable temperature. Suitable temperatures for the process may be from 0° C. to about 60° C., such as from about 20° C. to about 50° C., for instance from about 30° C. to about 40° C. It is particularly preferred that step (ii) is carried out at about 37° C. The temperature may be maintained by any suitable means, for instance using a shaking incubator. 2,5-Furandicarboxylic acid (2,5-FDCA) can be isolated by a range of means, for instance by heat treatment of the reaction solution to precipitate the protein, followed by centrifugation, acidification and filtration.

The 5-hydroxymethylfurfural in the process of the third aspect of the invention, and the features thereof, can be obtained from glucose and/or fructose. The glucose and/or fructose can be obtained from lignocellulose.

The biocatalyst of the present invention can be produced in a purified or partially purified form or as a component of a cell lysate. Alternatively, the production of 2,5-furandicarboxylic acid (2,5-FDCA) can be catalysed by using a suitable naturally occurring or modified bacterium which includes the required biocatalysts.

The fourth aspect of the invention relates to a process for the formation of 2,5-furandicarboxylic acid as set out in the processes of the first aspect of the invention, where the xanthine oxidoreductase (XOR) and galactose oxidase variant $M_{3-5}$ (GOase $M_{3-5}$) are replaced with ketoreductase (KRED) and either nicotinamide adenine dinucleotide phosphate (NADP+) or nicotinamide adenine dinucleotide (NAD+). All preferred features of the first aspect relate to the processes of the fourth aspect of the invention.

In a feature of the fourth aspect of the invention there is provided a process for the formation of 2,5-furandicarboxylic acid (2,5-FDCA) from 5-hydroxymethylfurfural (HMF), said process comprising the steps of
(i) providing 5-hydroxymethylfurfural; and
(ii) adding ketoreductase (KRED), and either nicotinamide adenine dinucleotide phosphate (NADP+) or nicotinamide adenine dinucleotide (NAD+).

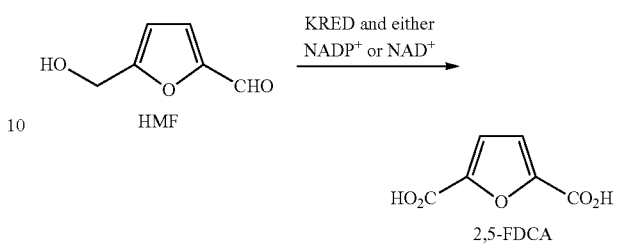

In another feature of the fourth aspect of the invention there is provided a process for the formation of formylfurancarboxylic acid (FFCA) from 5-hydroxymethylfurfural (HMF), said process comprising the steps of
(i) providing 5-hydroxymethylfurfural; and
(ii) adding ketoreductase (KRED), and either nicotinamide adenine dinucleotide phosphate (NADP+) or nicotinamide adenine dinucleotide (NAD+).

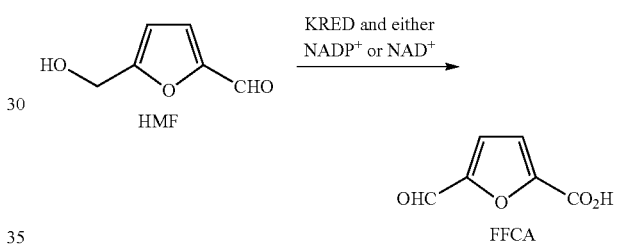

It is preferred that the processes of the fourth aspect of the invention comprise adding nicotinamide oxidase (NOX) in step (ii).

It will be understood that the process is a one-pot process whereby the 5-hydroxymethylfurfural (HMF) is converted into 2,5-furandicarboxylic acid (2,5-FDCA) in a single reactor and without separating or purifying any intermediate compounds.

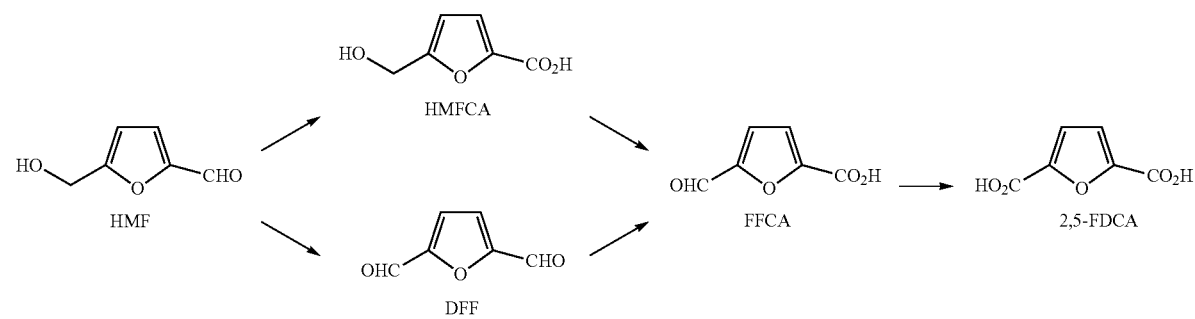

Thus, for example, the 2,5-furandicarboxylic acid can be produced via hydroxymethyl furancarboxylic acid (HMFCA) diformyl furan (DFF) and/or formylfurancarboxylic acid (FFCA) as illustrated above.

In step (ii), the ketoreductase (KRED) and either nicotinamide adenine dinucleotide phosphate (NADP+) or nicotinamide adenine dinucleotide (NAD+) (and when present the nicotinamide oxidase (NOX)) are added to the unreacted 5-hydroxymethylfurfural. It is preferred that the nicotinamide adenine dinucleotide phosphate (NADP$^+$) is used.

The term "unreacted 5-hydroxymethylfurfural" refers to the 5-hydroxymethylfurfural provided in step (i) and means that at least about 90%, such as at least about 95%, preferably at least about 99%, most preferably about 100% of 5-hydroxymethylfurfural is present, based upon the amount of 5-hydroxymethylfurfural provided in step (i). In step (ii), KRED and either NADP$^+$ or NAD$^+$ (and when present the NOX) are added to the unreacted HMF. The skilled person will understand that KRED and either NADP$^+$ or NAD$^+$ (and when present the NOX) may be added in step (ii) simultaneously and/or sequentially and in any order. This includes adding one or more of KRED and either NADP$^+$ or NAD$^+$ (and when present the NOX), as a mixture or separately, and then adding the remaining KRED and either NADP$^+$ or NAD$^+$ (and when present the NOX).

When NADP$^+$ is present in the reaction, it is preferred that the nicotinamide oxidase (NOX) is nicotinamide oxidase 1 (NOX-1). When NAD$^+$ is present in the reaction, it is preferred that the NOX is nicotinamide oxidase 9 (NOX-9).

In the fourth aspect of the invention, the 5-hydroxymethylfurfural may be provided in a solution in step (i), preferably an aqueous solution. Preferably, 5-hydroxymethylfurfural may be provided in a solution at a concentration of from about 1 mM to about 1,000 mM, such as from about 10 mM to about 750 mM, for instance from about 50 mM to about 500 mM.

When the 5-hydroxymethylfurfural is provided in a solution in step (i), the ketoreductase (KRED) may be added to the solution in step (ii) in an amount of from about 1 mg/mL to about 500 mg/mL, such as from about 5 mg/mL to about 200 mg/mL, for example from about 10 mg/mL to about 100 mg/mL, preferably from about 15 mg/mL to about 50 mg/mL.

NADP$^+$ or NAD$^+$ may be added in step (ii) in an amount of from about 5 mol % to about 50 mol %, such as from about 10 mol % to about 30 mol %, preferably about 20 mol %, based upon the amount of 5-hydroxymethylfurfural provided in step (i).

Nicotinamide oxidase is preferably provided in step (ii) in an amount of from about 50 weight % to about 180 weight %, such as from about 60 to about 150 weight %, preferably from about 65 weight % to about 140 weight %, based upon the amount of ketoreductase.

It is preferred that catalase is provided in step (i) and/or step (ii) of the process of the fourth aspect of the invention. The catalase may be provided in a mass ratio of from about 1:100 to about 1:1, such as from 1:75 to about 1:20, for instance from about 1:50 to about 1:30 with respect to the 5-hydroxymethylfurfural. Additional catalase can be added to the reaction as required.

As discussed in relation to the first aspect of the invention, buffer may be provided as part of the process of the fourth aspect of the invention, to maintain a pH of from about 6 to about 8 in the process. Preferably, the buffer is added in step (ii). Any suitable buffer can be used in the reaction. Particularly useful buffers are phosphate buffers, such as a potassium phosphate buffer.

Thus, each of the processes of the present invention is preferably carried out in a buffered reaction mixture with a pH of 6 to 8. Preferably the reaction mixture is buffered with a phosphate buffer, more preferably potassium phosphate buffer. The pH may be determined by any known means. It is preferred that the pH is determined using a pH meter and a probe.

The processes of the fourth aspect of the invention can be conducted at any suitable temperature. Suitable temperatures for the process may be from 0° C. to about 60° C., such as from about 20° C. to about 50° C., for instance from about 30° C. to about 40° C. It is particularly preferred that step (ii) is carried out at about 37° C. The temperature may be maintained by any suitable means, for instance using a shaking incubator.

2,5-Furandicarboxylic acid (2,5-FDCA) can be isolated by a range of means, for instance by heat treatment of the reaction solution to precipitate the protein, followed by centrifugation, acidification and filtration.

As discussed for the first aspect of the invention, the 5-hydroxymethylfurfural (HMF) may be prepared from glucose and/or fructose. The glucose and fructose may be formed from lignocelluloses.

The biocatalyst of the present invention can be produced in a purified or partially purified form or as a component of a cell lysate. Alternatively, the production of 2,5-furandicarboxylic acid (2,5-FDCA) can be catalysed by using a suitable naturally occurring or modified bacterium which includes the required biocatalysts.

In a fifth aspect of the invention there is provided a process for the formation of 2,5-furandicarboxylic acid (2,5-FDCA) from diformyl furan (DFF) comprising the steps of
(i) providing diformyl furan; and
(ii) adding periplasmic aldehyde oxidase (PaoABC), catalase and H$_2$O$_2$.

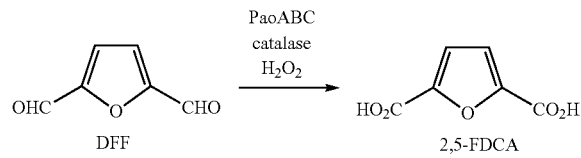

H$_2$O$_2$ may be added in one portion or, preferably, portion-wise. Suitable portion-wise addition of H$_2$O$_2$ includes adding 2, 3, 4, 5, 6, 7, 8, 9, or 10 (or more) portions of H$_2$O$_2$ during the formation of 2,5-furandicarboxylic acid from diformyl furan. The addition of each portion of H$_2$O$_2$ may be separated by a time interval of from about 5 to 60 minutes, such as from 10 to 30 minutes, preferably about 15 minutes.

The catalase may be provided in a mass ratio of from about 1:100 to about 1:1, such as from 1:75 to about 1:20, for instance from about 1:50 to about 1:30 with respect to the diformyl furan. Additional catalase can be added to the reaction as required. The catalase can be added simultaneously, sequentially or separately to the oxidase enzyme.

It is advantageous to use sufficient buffer capacity to control the pH of the reaction and to drive the reaction to completion. Preferably the optimum pH of the reaction is from pH 6 to pH 8. Any suitable buffer can be used in the reaction. Particularly useful buffers are phosphate buffers, such as a potassium phosphate buffer.

Thus, each of the processes of the present invention is preferably carried out in a buffered reaction mixture with a pH of 6 to 8. Preferably the reaction mixture is buffered with a phosphate buffer, more preferably potassium phosphate buffer. The pH may be determined by any known means. It is preferred that the pH is determined using a pH meter and a probe.

The processes of the fifth aspect of the invention can be conducted at any suitable temperature. Suitable temperatures for the process may be from 0° C. to about 60° C., such as from about 20° C. to about 50° C., for instance from about 30° C. to about 40° C. It is particularly preferred that step (ii) is carried out at about 37° C. The temperature may be maintained by any suitable means, for instance using a shaking incubator.

Diformyl furan may be provided in a solution in step (i), preferably an aqueous solution. Preferably, diformyl furan may be provided in a solution at a concentration of from about 1 mM to about 1,000 mM, such as from about 10 mM to about 750 mM, for instance from about 50 mM to about 500 mM.

2,5-Furandicarboxylic acid (2,5-FDCA) can be isolated by a range of means, for instance by heat treatment of the reaction solution to precipitate the protein, followed by centrifugation, acidification and filtration.

The biocatalyst of the present invention can be produced in a purified or partially purified form or as a component of a cell lysate. Alternatively, the production of 2,5-furandicarboxylic acid (2,5-FDCA) can be catalysed by using a suitable naturally occurring or modified bacterium which includes the required biocatalysts.

In a sixth aspect of the invention there is provided a process for the formation of 2,5-furandicarboxylic acid (2,5-FDCA) from diformyl furan (DFF) comprising the steps of
(i) providing diformyl furan; and
(ii) adding immobilised periplasmic aldehyde oxidase (PaoABC), and optionally immobilised catalase.

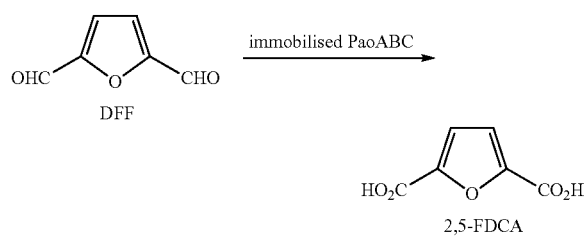

As used herein, the term "immobilised" periplasmic aldehyde oxidase (PaoABC) and "immobilised" catalase refers to periplasmic aldehyde oxidase or catalase that is attached to, or entrapped in, an inert, insoluble material. Materials suitable for immobilising enzymes, such as PaoABC and catalase, are known in the art and include epoxide-based resins, such as Eupergit CM; hydrogels, such as those comprising polyvinyl imidazole (PVI), polyethylene imine (PEI), and/or polyethylene glycol (PEG) stabilisers; enzyme affinity columns, such as those used in immobilised metal ion affinity chromatography (IMAC); and as cross-linked enzyme aggregates (CLEA).

Immobilised catalase, such as CLEA catalase, may be provided in a mass ratio of from about 1:100 to about 1:1, such as from 1:75 to about 1:20, for instance from about 1:50 to about 1:30 based upon the amount of catalase with respect to the DFF. Additional immobilised catalase can be added to the reaction as required.

Diformyl furan may be provided in a solution in step (i), preferably an aqueous solution. Preferably, diformyl furan may be provided in a solution at a concentration of from about 1 mM to about 1,000 mM, such as from about 10 mM to about 750 mM, for instance from about 50 mM to about 500 mM.

It is advantageous to use sufficient buffer capacity to control the pH of the reaction and to drive the reaction to completion. Preferably the optimum pH of the reaction is from pH 6 to pH 8. Any suitable buffer can be used in the reaction. Particularly useful buffers are phosphate buffers, such as a potassium phosphate buffer.

Thus, each of the processes of the present invention is preferably carried out in a buffered reaction mixture with a pH of 6 to 8. Preferably the reaction mixture is buffered with a phosphate buffer, more preferably potassium phosphate buffer. The pH may be determined by any known means. It is preferred that the pH is determined using a pH meter and a probe.

The processes of the sixth aspect of the invention can be conducted at any suitable temperature. Suitable temperatures for the process may be from 0° C. to about 60° C., such as from about 20° C. to about 50° C., for instance from about 30° C. to about 40° C. It is particularly preferred that step (ii) is carried out at about 37° C. The temperature may be maintained by any suitable means, for instance using a shaking incubator.

2,5-Furandicarboxylic acid (2,5-FDCA) can be isolated by a range of means, for instance by heat treatment of the reaction solution to precipitate the protein, followed by centrifugation, acidification and filtration.

The DFF may be prepared from HMF, which may be formed from glucose and/or fructose. The glucose and fructose may be formed from lignocelluloses.

It will be appreciated that the features of the sixth aspect of the invention apply equally to the first, second and fifth aspects of the invention. Therefore, the PaoABC and catalase in the processes described in the first, second and fifth aspects of the invention may be immobilised periplasmic aldehyde oxidase and/or immobilised catalase.

The biocatalyst of the present invention can be produced in a purified or partially purified form or as a component of a cell lysate. Alternatively, the production of 2,5-furandicarboxylic acid (2,5-FDCA) can be catalysed by using a suitable naturally occurring or modified bacterium which includes the required biocatalysts.

In a seventh aspect of the invention there is provided a process for the formation of a mono- or diester of 2,5-furandicarboxylic acid from 2,5-furandicarboxylic acid, comprising the step of
(i) providing 2,5-furandicarboxylic acid; and
(ii) adding an alcohol and a catalyst
wherein the 2,5-furandicarboxylic acid is obtained by a process as defined in any one of the first to sixth aspects of the invention.

Any suitable alcohol can be used, with methanol and ethanol preferred. Ethanol is particularly preferred. Therefore, the seventh aspect of the relates to a process is for the formation of a mono- or diester of 2,5-furandicarboxylic acid selected from the group consisting of

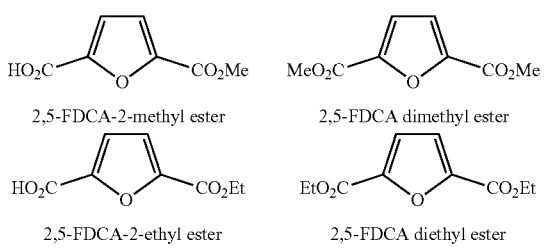

and a combination thereof,
comprising the steps of (i) providing 2,5-furandicarboxylic acid; and
(ii) adding methanol or ethanol and a catalyst to the 2,5-furandicarboxylic acid wherein the 2,5-furandicarboxylic acid is obtained by a process as defined in any one of the first to sixth aspects of the invention.

Any suitable catalyst may be used. Preferred catalysts are organic acids or inorganic acids, such as mineral acids. Typical organic acids include acetic acid, trifluoroacetic acid or formic acid; typical inorganic acids include hydrochloric acid and sulfuric acid. Inorganic acids are preferred, with sulphuric acid being particular preferred.

In an eighth aspect of the invention, there is provided a process for the formation of a copolymer comprising the copolyester of 2,5-furandicarboxylic acid (2,5-FDCA) or a mono- or diester of 2,5-furandicarboxylic acid.

Thus, the eighth aspect provides a process for the formation of a copolymer comprising the polymerisation product of
(a) at least one 2,5-furandicarboxylic acid (2,5-FDCA) or a mono- or diester of 2,5-furandicarboxylic acid;
(b) at least one diol; and
(c) optionally, at least one aliphatic dicarboxylic acid or a mono- or diester derivative thereof, wherein the process comprises reacting together components (a), (b) and, optionally, (c), and wherein the 2,5-furandicarboxylic acid is obtained by a process as defined in first to sixth aspects of the invention, and/or wherein the mono- or diester of 2,5-furandicarboxylic acid is obtained by a process as defined in the seventh aspect of the invention.

In a further feature of the eighth aspect of the invention there is provided a process for the formation of a copolymer comprising the polymerisation product of
(a) at least one mono- or diester of 2,5-furandicarboxylic acid;
(b) at least one diol; and
(c) at least one aliphatic dicarboxylic acid or a mono- or diester derivative thereof, wherein the process comprises reacting together components (a), (b) and (c), wherein the aliphatic dicarboxylic acid or a mono- or diester derivative thereof is selected from the group consisting of adipic acid, adipic acid monomethyl ester, adipic acid dimethyl ester, adipic acid monoethyl ester, adipic acid diethyl ester, succinic acid, succinic acid monomethyl ester, succinic acid dimethyl ester, succinic acid monoethyl ester, succinic acid diethyl ester, and a combination thereof.

In another feature of the eighth aspect of the invention there is provided a process for the formation of a copolymer comprising the polymerisation product of
(a) at least one mono- or diester of 2,5-furandicarboxylic acid;
(b) at least one diol; and
(c) at least one aliphatic dicarboxylic acid or a mono- or diester derivative thereof, wherein the process comprises reacting together components (a), (b) and (c), and wherein the mono- or diester of 2,5-furandicarboxylic acid is selected from the group consisting of

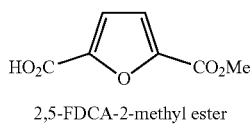

2,5-FDCA-2-methyl ester

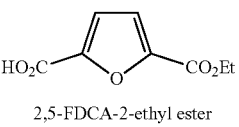

2,5-FDCA-2-ethyl ester

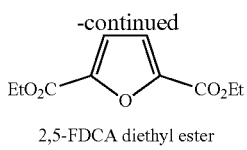

2,5-FDCA diethyl ester and a combination thereof.

In another feature of the eighth aspect of the invention there is provided a process for the formation of a copolymer that comprises the polymerisation product of
(a) at least one 2,5-furandicarboxylic acid (2,5-FDCA) or a mono- or diester of 2,5-furandicarboxylic acid;
(b) at least one diol; and
(c) at least one aliphatic dicarboxylic acid or a mono- or diester derivative thereof wherein the 2,5-furandicarboxylic acid is obtained by a process as defined in first to sixth aspects of the invention, and/or wherein the mono- or diester of 2,5-furandicarboxylic acid is obtained by a process as defined in the seventh aspect of the invention.

In another feature of the eighth aspect of the invention there is provided a process for the formation of a copolymer that consists essentially of
(a) at least one 2,5-furandicarboxylic acid (2,5-FDCA) or a mono- or diester of 2,5-furandicarboxylic acid;
(b) at least one diol; and
(c) at least one aliphatic dicarboxylic acid or a mono- or diester derivative thereof wherein the 2,5-furandicarboxylic acid is obtained by a process as defined in first to sixth aspects of the invention, and/or wherein the mono- or diester of 2,5-furandicarboxylic acid is obtained by a process as defined in the seventh aspect of the invention.

Such copolymers may exhibit properties that are similar to PBAT, such as being flexible, tough and biodegradable, and can be used either as a replacement for PBAT or in combination with PBAT.

The 2,5-furandicarboxylic acid (2,5-FDCA) or a mono- or diester of 2,5-furandicarboxylic acid, diol and aliphatic dicarboxylic acid or a mono- or diester derivative thereof can be referred to as monomers. The term "monomer" is one of the art. For the avoidance of any doubt, monomers are molecules that can be bonded to other molecules to form a copolymer.

The term "copolymer" is one of the art. It refers to a polymer comprising two or more different monomer units that are polymerised in a process called copolymerisation. Since a copolymer comprises at least two different monomer units, copolymers can be classified based on how the monomer units are arranged to form a polymer chain. Those classifications include "alternating copolymers" (in which the monomers units repeat with an regular alternating pattern), "periodic copolymers" (in which the monomers units are arranged with a repeating sequence), "statistical copolymers" (in which the sequence of monomer units follows a statistical rule), "random copolymers" (in which the monomer units are attached in a random order), and "block copolymers" (in which two or more homopolymer subunits are linked).

The copolymers of the invention may be a block copolymer, alternating copolymer, periodic copolymer, statistical copolymer or random copolymer. A preferred feature is that the copolymer is a random copolymer.

The term "consists essentially of" in this context means that copolymer of the invention is substantially free from any other monomer. That is, the copolymer of the invention comprises greater than about 90%, such as greater than about 95%, preferably greater than about 98%, and most preferably greater than about 99% of the listed monomers.

The term "at least one" is synonymous with "one or more", i.e. one, two, three, four, five, six, or more.

2,5-furandicarboxylic acids (2,5-FDCA) and mono- or diester of 2,5-furandicarboxylic acids that are of particular interest are 2,5-FDCA, 2,5-FDCA-2-methyl ester, 2,5-FDCA dimethyl ester, 2,5-FDCA-2-ethyl ester, 2,5-FDCA diethyl ester and combinations thereof, with 2,5-FDCA diethyl ester being particularly preferred. The 2,5-furandicarboxylic acid (2,5-FDCA) is provided according to the processes of the first to sixth aspects of the invention. The mono- or diester of 2,5-furandicarboxylic acids are provided according to the process of the seventh aspect of the invention.

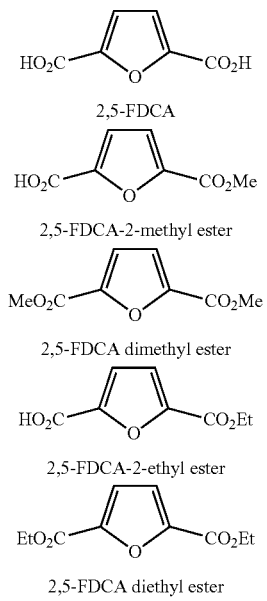

The term "diol" refers to a compound of formula

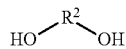

wherein $R^2$ is a straight or, where possible, branched or cyclic $C_2$ to $C_{10}$ saturated alkylene, preferably a $C_2$ to $C_6$ saturated alkylene, and more preferably $C_2$ to $C_4$ saturated alkylene, or a mixture thereof.

The term "alkylene" refers to an alkyl diradical, including straight-chain, and, where possible, branched-chain and cyclic groups. Where the alkylene group refers to a range, such as $C_2$ to $C_{12}$, it is to be understood that it includes each member of the range, i.e. $C_2$, $C_3$, $C_4$, $C_5$, $C_6$, $C_7$, $C_8$, $C_9$, $C_{10}$, $C_{11}$, and $C_{12}$.

The skilled person will understand that for a diol to be branched or cyclic then at least three carbon units are required. Non-limiting examples of branched diols useful in the invention are 1,2-propanediol, 1,2-butanediol, 2,2-dimethyl-1,3-propanediol. Non-limiting examples of cyclic diols useful in the invention are 1,2-cyclopentanediol, 1,2-cyclobutanediol, and 1,2-cyclopentanediol. The diols may also be branched, cyclic diols, e.g. 3-methyl-1,2-cyclopropanediol.

In a particular feature, the alkylene group present in the diol is unbranched.

In a preferred feature, the diol is 1,2-ethanediol, 1,4-butanediol, or combinations thereof, with 1,4-butanediol being particularly preferred. Copolymers formed from 1,4-butanediol or 1,2-ethanediol may exhibit properties that are similar to PBAT, as discussed above.

The term "aliphatic dicarboxylic acid or a mono- or diester derivative thereof" refers to a compound of formula

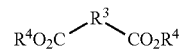

wherein $R^3$ is a straight or, where possible, branched or cyclic, $C_1$ saturated or $C_2$ to $C_{10}$ saturated or unsaturated alkylene, preferably $C_2$ to $C_6$ saturated or unsaturated alkylene, and more preferably $C_2$ to $C_4$ saturated or unsaturated alkylene, or combinations thereof, and wherein each $R^4$ independently represents H or a straight, or where possible branched or cyclic, $C_1$ to $C_6$ alkyl group, such as a $C_1$ to $C_4$ alkyl group, preferably H or a $C_1$ or $C_2$ alkyl group. It is preferable that the two $R^4$ groups are the same.

The term "alkyl" refers to a saturated aliphatic radical, including straight-chain, and, where possible, branched-chain and cyclic groups. Where the alkyl group refers to a range, such as $C_1$ to $C_6$, it is to be understood that it includes each member of the range, i.e. $C_1$, $C_2$, $C_3$, $C_4$, $C_5$, and/or $C_6$.

The alkylene group is as defined above. In particular, where the alkylene group contains 1 to 10 carbon atoms, it is to be understood that it includes each member of the range, i.e. the alkylene group can be a $C_1$, $C_2$, $C_3$, $C_4$, $C_5$, $C_6$, $C_7$, $C_8$, $C_9$ and/or $C_{10}$ alkylene. The alkyl group is as defined above.

The term "halide" or "halogen" are used interchangeably and, as used herein mean a fluorine ion, a chlorine ion, a bromine ion, an iodine ion and the like, An alkoxy group is preferably a "$C_{1-20}$ alkoxy group", more preferably a "$C_{1-15}$ alkoxy group", more preferably a "$C_{1-12}$ alkoxy group", more preferably a "$C_{1-10}$ alkoxy group", even more preferably a "$C_{1-8}$ alkoxy group", even more preferably a "$C_{1-6}$ alkoxy group" and is an oxy group that is bonded to the previously defined $C_{1-20}$ alkyl, $C_{1-16}$ alkyl, $C_{1-12}$ alkyl, $C_{1-10}$ alkyl, $C_{1-8}$ alkyl, or $C_{1-6}$ alkyl group respectively.

Sulphate is the dianion of $SO_4$

Acetate is $OC(O)R^x$, where $R^x$ is hydrogen, or optionally substituted alkyl, alkenyl, heteroalkyl, aryl, or heteroaryl.

Alkenyl and alkynyl groups are preferably "$C_{2-20}$alkenyl" and "$C_{2-20}$alkynyl", more preferably "$C_{2-15}$alkenyl" and "$C_{2-15}$alkynyl", even more preferably "$C_{2-12}$alkenyl" and "$C_{2-12}$alkynyl", even more preferably "$C_{2-10}$alkenyl" and "$C_{2-10}$alkynyl", even more preferably "$C_{2-8}$alkenyl" and "$C_{2-8}$alkynyl", most preferably "$C_{2-6}$alkenyl" and "$C_{2-6}$alkynyl" groups, respectively.

A heteroalkyl group is an alkyl group as described above, which additionally contains one or more heteroatoms. Heteroatoms are preferably selected from O, S, N, P and Si. A heteroaliphatic group is an aliphatic group as described above, which additionally contains one or more heteroatoms.

An aryl group is a monocyclic or polycyclic ring system having from 5 to 20 carbon atoms. An aryl group is preferably a "$C_{6-12}$ aryl group" and is an aryl group constituted by 6, 7, 8, 9, 10, 11 or 12 carbon atoms and includes condensed ring groups such as monocyclic ring group, or bicyclic ring group and the like.

A heteroaryl group is an aryl group having, in addition to carbon atoms, from one to four ring heteroatoms which are preferably selected from O, S, N, P and Si.

In a particular feature, the alkylene group present in the aliphatic dicarboxylic acid or a mono- or diester derivative thereof is unbranched.

Aliphatic dicarboxylic acids or mono- or diester derivatives thereof that are of particular interest are adipic acid (hexanedioic acid), adipic acid monomethyl ester, adipic acid dimethyl ester, adipic acid monoethyl ester, adipic acid diethyl ester, succinic acid (butanedioic acid), succinic acid monomethyl ester, succinic acid dimethyl ester, succinic acid monoethyl ester, succinic acid diethyl ester, or combinations thereof, with adipic acid diethyl ester being particularly preferred. Copolymers formed from adipic acid or a mono or diester derivative thereof may exhibit properties that are similar to PBAT, as discussed above.

All combinations of 2,5-furandicarboxylic acid or a mono- or diester of 2,5-furandicarboxylic acid, the diol, and the aliphatic dicarboxylic acid or a mono- or diester derivative thereof, are contemplated in the present invention.

The skilled person would understand that additional monomers may be incorporated into the copolymers of the invention produced by the process of the eighth aspect of the invention. Therefore, the process of the eighth aspect of the invention may also be for the formation of a copolymer comprising the polymerisation product of components (a), (b) and optionally (c) and, in addition, a heteroaromatic diacid (or a mono- or diester derivative thereof), aromatic diacid (or a mono- or diester derivative thereof), heteroaromatic diol and/or aromatic diol. Particular heteroaromatic and aromatic diacids that would be suitable for incorporation in the copolymers include pyridinedicarboxylic acids, such as 2,4-pyridinedicarboxylic acid (2,4-PDCA) and/or 2,5-pyridinedicarboxylic acid (2,5-PDCA), and terephthalic acid (or mono- or diester derivatives thereof).

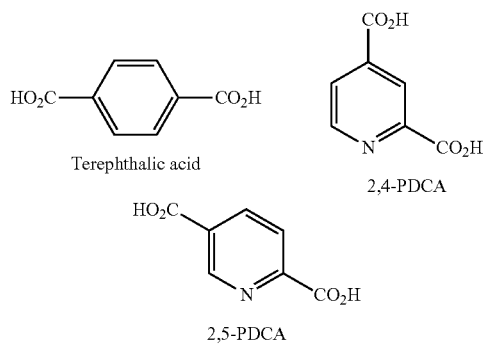

In a particular feature, there is provided a process for the formation of a copolymer comprising the polymerisation product of
(a) 2,5-furandicarboxylic acid (2,5-FDCA), 2,5-FDCA-2-methyl ester, 2,5-FDCA dimethyl ester, 2,5-FDCA-2-ethyl ester, 2,5-FDCA diethyl ester or combinations thereof;
(b) 1,2-ethanediol, 1,4-butanediol, or combinations thereof; and,
(c) adipic acid, adipic acid monomethyl ester, adipic acid dimethyl ester, adipic acid monoethyl ester, adipic acid diethyl ester, succinic acid, succinic acid monomethyl ester, succinic acid dimethyl ester, succinic acid monoethyl ester, succinic acid diethyl ester, or combinations thereof wherein the 2,5-furandicarboxylic acid is obtained by a process as defined in first to sixth aspects of the invention, and/or wherein the mono- or diester of 2,5-furandicarboxylic acid is obtained by a process as defined in the seventh aspect of the invention.

It may be advantageous to use diester derivatives of 2,5-furandicarboxylic acid and/or the aliphatic dicarboxylic acid to form the copolymers of the invention. It may be particularly advantageous to use the same diester derivative of the 2,5-furandicarboxylic acid and the aliphatic dicarboxylic acid, i.e. 2,5-furandicarboxylic acid diethyl ester and adipic acid diethyl ester.

In a preferred feature of the eighth aspect of the invention, the process is for the formation of a copolymer that is the polymerisation product of
(A) 2,5-furandicarboxylic acid (2,5-FDCA) dimethyl ester or diethyl ester;
(B) 1,4-butanediol; and
(C) adipic acid dimethyl ester or diethyl ester,
and in particular of
(A) 2,5-furandicarboxylic acid diethyl ester;
(B) 1,4-butanediol; and
(C) adipic acid dimethyl ester or diethyl ester.

wherein the 2,5-furandicarboxylic acid is obtained by a process as defined in first to sixth aspects of the invention, and/or wherein the mono- or diester of 2,5-furandicarboxylic acid is obtained by a process as defined in the seventh aspect of the invention.

In a preferred feature of the eighth aspect of the invention, the process is for the formation of a copolymer that is the polymerisation product of
(A) 2,5-furandicarboxylic acid (2,5-FDCA) or a mono- or diester of 2,5-furandicarboxylic acid; and
(B) 1,2-ethanediol, 1,4-butanediol, or a combination thereof.

wherein the 2,5-furandicarboxylic acid is obtained by a process as defined in first to sixth aspects of the invention, and/or wherein the mono- or diester of 2,5-furandicarboxylic acid is obtained by a process as defined in the seventh aspect of the invention.

A copolymer of the invention may be formed from about 1 to about 99 mol %, such as from about 10 to about 70 mol %, preferably from about 25 mol % to about 35 mol %, of 2,5-furandicarboxylic acid or a mono- or diester of 2,5-furandicarboxylic acid. A copolymer of the invention may be formed from about 1 to about 99 mol %, such as from about 20 to about 70 mol %, preferably from about 45 mol % to about 55 mol %, of diol. A copolymer of the invention may be formed from about 1 to about 98 mol %, such as from about 10 to about 70 mol %, preferably from about 25 mol % to about 35 mol %, of aliphatic dicarboxylic acid a mono- or diester derivative thereof. The above mol % values are based upon the total amount of 2,5-furandicarboxylic acid or a mono- or diester of 2,5-furandicarboxylic acid, diol, and aliphatic dicarboxylic acid or mono- or diester derivative thereof. When the copolymer consists essentially of 2,5-furandicarboxylic acid or a mono- or diester of 2,5-furandicarboxylic acid, diol, and aliphatic dicarboxylic acids or mono- or diester derivatives thereof, it will be understood that the amount of diol will be about 50 mol % and the combined amount of 2,5-furandicarboxylic acid or a mono- or diester of 2,5-furandicarboxylic acid and aliphatic dicarboxylic acids or mono- or diester derivatives thereof will also be about 50 mol %.

As used herein the term "about" applies to all values, numeric or otherwise, whether or not explicitly indicated. Those values generally encompass or refer to a range of values that one skilled in the art would consider equivalent to the recited values (i.e. having the same function or result). Where the term "about" is used in relation to a numerical value, it can represent (in increasing order of preference) a 10%, 5%, 2% or 1% deviation from that value.

It will be understood by those skilled in the art that an excess of one of the monomers will typically result in polymer chains that terminate with that particular monomer.

The copolymers may be prepared by reacting together at least one 2,5-furandicarboxylic acid or a mono- or diester of 2,5-furandicarboxylic acid with at least one diol and at least one aliphatic dicarboxylic acid or a mono- or diester derivative thereof simultaneously or concomitantly under standard conditions to form a copolymer. Such conditions include conditions suitable to perform, for instance, condensation reactions or transesterification reactions. The reaction type is of course dependent upon the terminal groups of the monomer starting materials. Preferably, the polymers are prepared by melt polymerisation or solvent-based condensation reactions.

Those skilled in the art will understand the methods and conditions that may be used to react together the monomers to form a copolymer as a block copolymer, alternating copolymer, periodic copolymer, statistical copolymer or random copolymer. It is preferred that the process is for the formation of a random copolymer.

It is understood that the molar ratios of monomers used in the process may reflect the molar ratios of monomers as present in the resulting copolymer. This notwithstanding, it has been found to be advantageous to use an excess of at least one diol, in particular when a mono- or diester derivative of at least one 2,5-furandicarboxylic acid and/or a mono- or diester of 2,5-furandicarboxylic acid or at least one aliphatic dicarboxylic acid is used. Without wishing to be bound by theory, this may advantageously help to ensure that the terminal groups of the copolymers comprise an alcohol. A suitable excess of at least one diol may be greater than about 5 mol %, such as greater than about 10 mol %, for instance greater than about 20 mol %, and preferably about 25 mol %, based upon the total amount of 2,5-furandicarboxylic acid or a mono- or diester of 2,5-furandicarboxylic acid and aliphatic dicarboxylic acid or mono- or diester derivative thereof in the reaction. Additional diol may be added during the process of the invention.

The formation of a copolymer in the process of the eighth aspect of the invention may be carried out in the presence of a catalyst. Typical catalysts useful in the eighth aspect of the invention may contain a metal, such as a transition metal, or an organometallic catalyst, and a Lewis acid, with aluminium, tin, antimony, titanium, and their alkoxides being particularly preferred. Titanium(IV) tert-butoxide and titanium(IV) isopropoxide are exemplary catalysts.

The process for the formation of a copolymer may be carried out in the presence of a suitable solvent, for example water or an organic solvent such as ethyl acetate, toluene, tetrahydrofuran, diethyl ether, dioxane, dimethylformamide, dimethylsulfoxide, an alcohol (such as methanol or ethanol), or mixtures thereof (including biphasic solvent systems, such as a mixture of water and an organic solvent). It is preferred that the process of the invention is carried out "neat", that is, no solvent is added to the reaction. The skilled person will understand that reacting together certain monomers (such as reacting together monomers comprising an ester group, i.e. an ethyl ester, with monomers comprising an alcohol group, in a transesterification reaction or condensation reaction) may form "solvent" (i.e. water or an alcohol, such as methanol or ethanol) as a result of the reaction. It is to be understood that the formation of a solvent during the reaction is not to be considered as solvent being added to the reaction. Such reactions are also considered to be carried out "neat". It may however be advantageous to use ethyl acetate as a solvent when 2,5-furandicarboxylic acid and/or an aliphatic dicarboxylic acid is used in the process.

The process for the formation of a copolymer may be performed at any suitable reaction temperature, for instance at room temperature or an elevated temperature. A preferred feature of the invention is that the reaction is carried out at one or more elevated temperatures. That is, the reaction is heated to a first reaction temperature at which the reaction remains for a first length of time. After this time, the reaction temperature is changed (i.e. raised or lowered) to a second reaction temperature at which the reaction remains for a second length of time. The process of changing the reaction temperature may be subsequently repeated. Suitable temperatures include temperatures from about 60° C. to about 250° C., such as from about 90° C. to about 220° C., i.e. from about 110° C. to about 180° C. Suitable times at which the reaction is held at a temperature are from about 1 hour to about 24 hours, such as from about 2 hours to about 19 hours, i.e. from about 3 hours or about 4 hours to about 17 hours.

The process for the formation of a copolymer in the eighth aspect of the invention may be performed at any suitable reaction pressure, for instance at atmospheric (or ambient) pressure or at an increased or reduced pressure. The terms "increased pressure" and "reduced pressure" are ones of the art and includes all pressure that are, respectively, above or below atmospheric (or ambient) pressure. In a preferred feature of the invention, the reaction pressure is changed (i.e. increased or decreased) during the process of the eighth aspect of the invention.

The change in reaction pressure may coincide with a change in the reaction temperature, as discussed above. Those skilled in the art will understand that a change in pressure and/or temperature does not take immediately effect within a reaction. Therefore, when the change in reaction pressure coincides with a change in the reaction temperature, the changes are made at about the same time or over the same or similar time period.

It is preferred that the reaction pressure is reduced over the course of the process of the invention. In particular, the process may be maintained at atmospheric pressure for a first time period, and then lowered to a reduced pressure for a second time period. The process of changing the reaction pressure may be subsequently repeated. Suitable reduced pressures include pressures from about 1 mbar to about 500 mbar such as from about 10 mbar to about 300 mbar i.e. from about 25 mbar to about 200 mbar.

In a particularly feature of the process for the formation of a copolymers of the invention, the process is performed at 110° C. for 4 hours at atmospheric pressure, then at 180° C. for 17 hours at 200 mbar, and then at 180° C. for 3 hours at 25 mbar.

The polymerisation reaction may be mixed, i.e. stirred, to ensure that a homogeneous reaction mixture is formed. Mixing the reaction may ensure, for instance, that a homogeneous, random polymer is formed. As is known, the formation of a polymer may result in an increase in the viscosity of a reaction mixture. Those skilled in the art will appreciate that a suitable mixing device should be employed.

A copolymer that is obtained by the process may be purified or separated from the reaction mixture by standard techniques, for instance by precipitation and filtration, evaporation, chromatography, and/or evaporation of solvents.

In general, the process of the eighth aspect of the invention may be operated as a batch process or operated as a continuous process or flow process, and may be conducted on any scale.

The processes disclosed herein may have the advantage that the copolymers of the invention, or precursors thereof, may be produced in a high yield, in a high purity, in less time, in a more convenient form (i.e. easier to handle), at a low cost, and from renewable sources. The processes may be considered "green" or "clean" and therefore have environmental benefits for both the processes and the copolymers of the invention.

In a ninth aspect of the invention, there is provided a copolymer formed by a process as defined in the eighth aspect of the invention.

A copolymer of the ninth aspect of the invention is as illustrated in Formula I

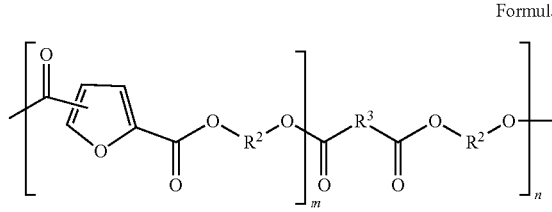

Formula I wherein $R^2$ and $R^3$ are as defined above, and m and n are integers greater than zero.

Particularly when carried out on an industrial scale, m may be from about 1 to about 400, such as from about 3 to about 350, for instance from about 5 to about 300, for example from about 7 to about 250, i.e. from about 10 to about 200, and n may be from about 1 to about 400, such as from about 3 to about 350, for instance from about 5 to about 300, for example from about 7 to about 250, i.e. from about 10 to about 200.

It is preferred that $R^2$ is a $C_2$ to $C_4$ alkylene, and $R^3$ is a $C_4$ to $C_6$ alkylene.

It will be apparent to those skilled in the art that the nomenclature used in, for instance, Formula I does not denote the type of copolymer, i.e. a block copolymer, alternating copolymer, periodic copolymer, statistical copolymer or random copolymer. The copolymer of Formula I may be any copolymer type. However, it is preferred that it is a random copolymer.

A copolymer of the ninth aspect of the invention may also be as illustrated in Formula IA

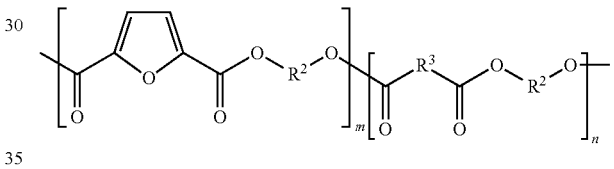

Formula IA wherein $R^2$, $R^3$, m and n are as defined above.

A copolymer of the ninth aspect of the invention may also be as illustrated in Formula II

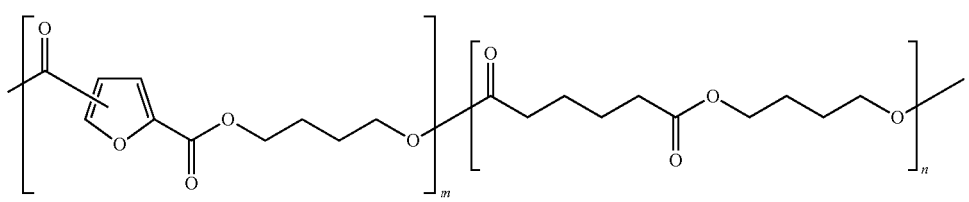

Formula II wherein m and n are as defined above.

A copolymer of the ninth aspect of the invention may also be as illustrated in Formula IIA

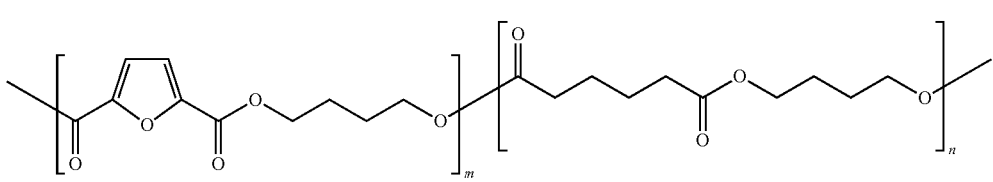

Formula IIA wherein m and n are as defined above.

A copolymer of the invention may have a molecular weight of from about 1,000 to about 100,000 gmol$^{-1}$, for example from about 2,000 to about 60,000 gmol$^{-1}$, such as from about 3,000 to about 50,000 gmol$^{-1}$, preferably from about 4,000 to about 30,000 gmol$^{-1}$, and most preferably from about 5,000 to about 20,000 gmol$^{-1}$. Such copolymers have particularly useful properties. The molecular weight of the copolymers was measured by Gel Permeation Chromatography (GPC) against a polystyrene standard set as per Example 16.

A copolymer of the invention may have at least one decomposition temperature within a range of from about 300° C. to about 450° C., and preferably from about 350° C. to about 400° C. Without wishing to be bound by theory, the decomposition temperature may relate to the decomposition of the copolymer backbone. Simultaneous Thermal Analysis (STA) was used to determine the decomposition temperature of copolymer samples under an inert ($N_2$) atmosphere as defined in Example 15.

A copolymer of the invention may have a first glass transition temperature ($T_{g1}$) within a range of from about −50° C. to about 0° C., and preferably from about −40° C. to about −20° C. The copolymer may have a second glass transition temperature ($T_{g2}$) within a range of from about 20° C. to about 60° C., and preferably from about 30° C. to about 50° C.

A copolymer of the invention may have a melting point ($T_m$) within a range of from about 60° C. to about 120° C., and preferably from about 80° C. to about 100° C.

Differential Scanning calorimetry (DSC) was used to determine the glass transition temperature (Tg) and the melting point ($T_m$) as defined in Example 15.

A copolymer of the invention may have a tensile strength in the range from about 1 MPa to about 50 MPa, such as from about 2 MPa to about 30 MPa, i.e. from about 3 MPa to about 15 MPa.

A copolymer of the invention may be stretched or elongated. The percentage elongation of the copolymer at its breaking point can range from about 1% to about 500%, such as from about 2% to about 300%, for example from about 3% to about 100% as based upon the original length of the copolymer.

A copolymer of the invention may have a Young's modulus in the range from about 10 MPa to about 500 MPa, such as from about 30 MPa to about 300 MPa, for example from about 50 MPa to about 150 MPa, i.e. from about 80 MPa to about 110 MPa.

Tensile strength, elongation and Young's modulus of the copolymers of the invention were measured as defined in Example 17.

Methods for testing the properties of copolymers, such as decomposition temperature, glass transition temperature, melting point, tensile strength etc. will be known to those skilled in the art.

A copolymer of the invention may be biodegradable and/or compostable. They may take less time to break down and be easier to recycle than current commercial polymers, such as PET and PBAT. Degradation may take place via a number of pathways including by hydrolysis and/or oxidation. Microorganisms, such as bacteria, yeasts, fungi, and also enzymatic processes also lead to biodegradation. For instance, enzymatic degradation of aliphatic polyesters including polyesters based upon succinic acid and aliphatic diols are known (see Tokiwa; Suzuki *Nature* 1977, 270, 76 to 78).

It has been found that 2,5-furandicarboxylic acid represents a viable aromatic alternative to the use of terephthalic acid in polymers, such as PET and PBAT. Thus, copolymers comprising 2,5-furandicarboxylic acid may be useful as replacements for PET or PBAT, and minimise the environmental and economic impact of current commercial polymers.

In a tenth aspect of the invention, there is provided a polymer blend comprising a copolymer of the invention. A polymer blend may be defined as a macroscopically homogeneous mixture of two or more different species of polymer. For instance, the polymer blends may be binary, ternary, quaternary or higher polymer blends.

The copolymers of the invention may be blended with, for instance, polylactic acid (PLA), starch, cellulose acetate, polyhydroxybutyrate (PHB), isotactic polypropylene (PP), poly(butylene succinate), poly-ε-caprolactone, poly(ethylene glycol), poly(ethylene oxide), and polymethyl methacrylate (PMMA). It is preferred that the copolymers of the invention are blended with PLA, starch and/or cellulose acetate.

A copolymer of the invention or polymer blends comprising the copolymer may take any physical form, for instance pellets, powders, sheets, fibres, or granules. It may be particularly advantageous for the copolymers or polymer blends to be pellets or granules to help processability or handling.

In an eleventh aspect of the invention there is provided an article comprising a copolymer of the invention or a polymer blend as described above. The term "article" is synonymous with an item or product. Such articles include articles currently made from plastics and in particular those made using materials comprising or consisting of PET and PBAT.

The copolymers of the invention may be used to form an article.

All preferred features of the first to the eleventh aspects of the invention relate to all other aspects of the invention mutatis mutandis.

GOase M$_{3-5}$, PaoABC and horseradish peroxidase (HRP) were added at the start of the reaction.

Figure 13:
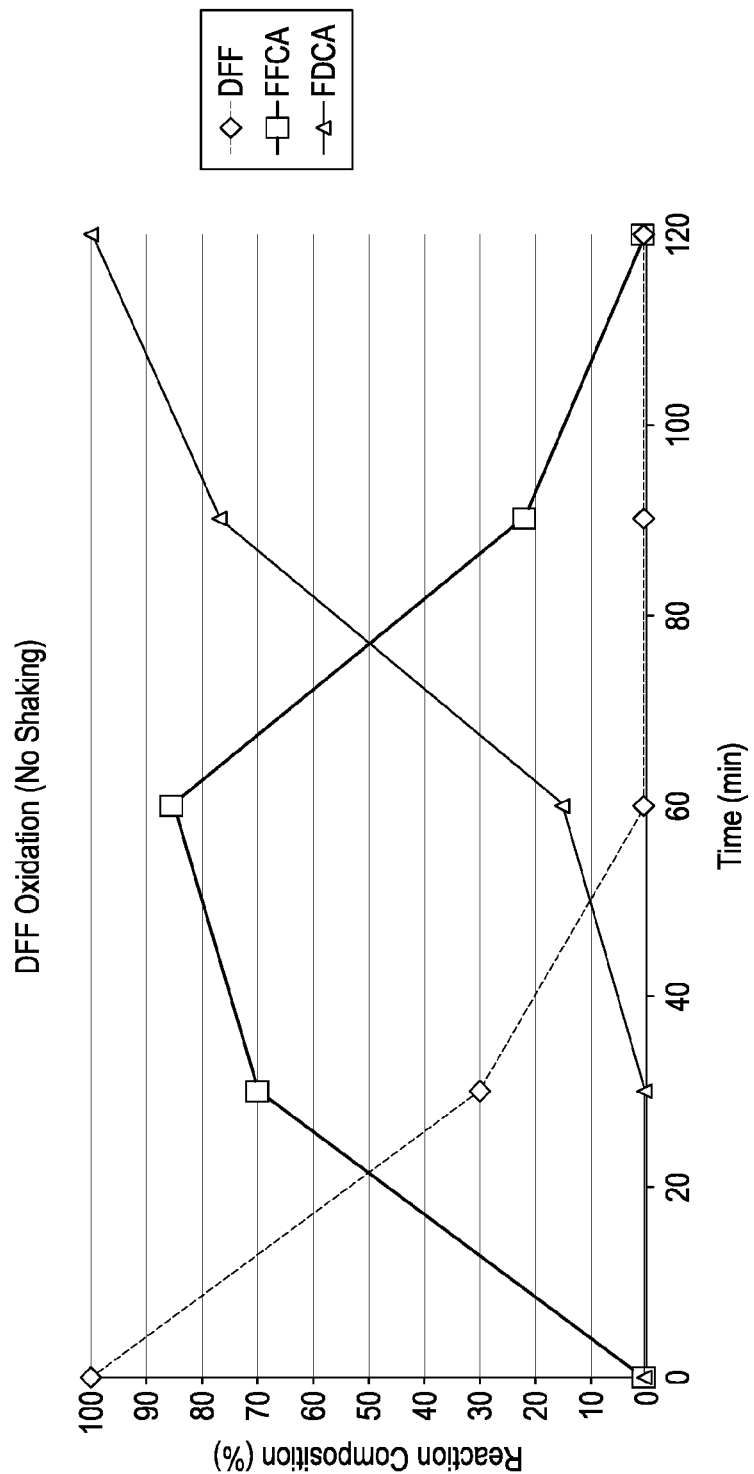

FIG. 13 shows the relative amount of DFF, FFCA and 2,5-FDCA as a function of time during the process described in Example 5. DFF was consumed in about 60 minutes with complete conversion of DFF to 2,5-FDCA taking about 120 minutes.

Figure 14:
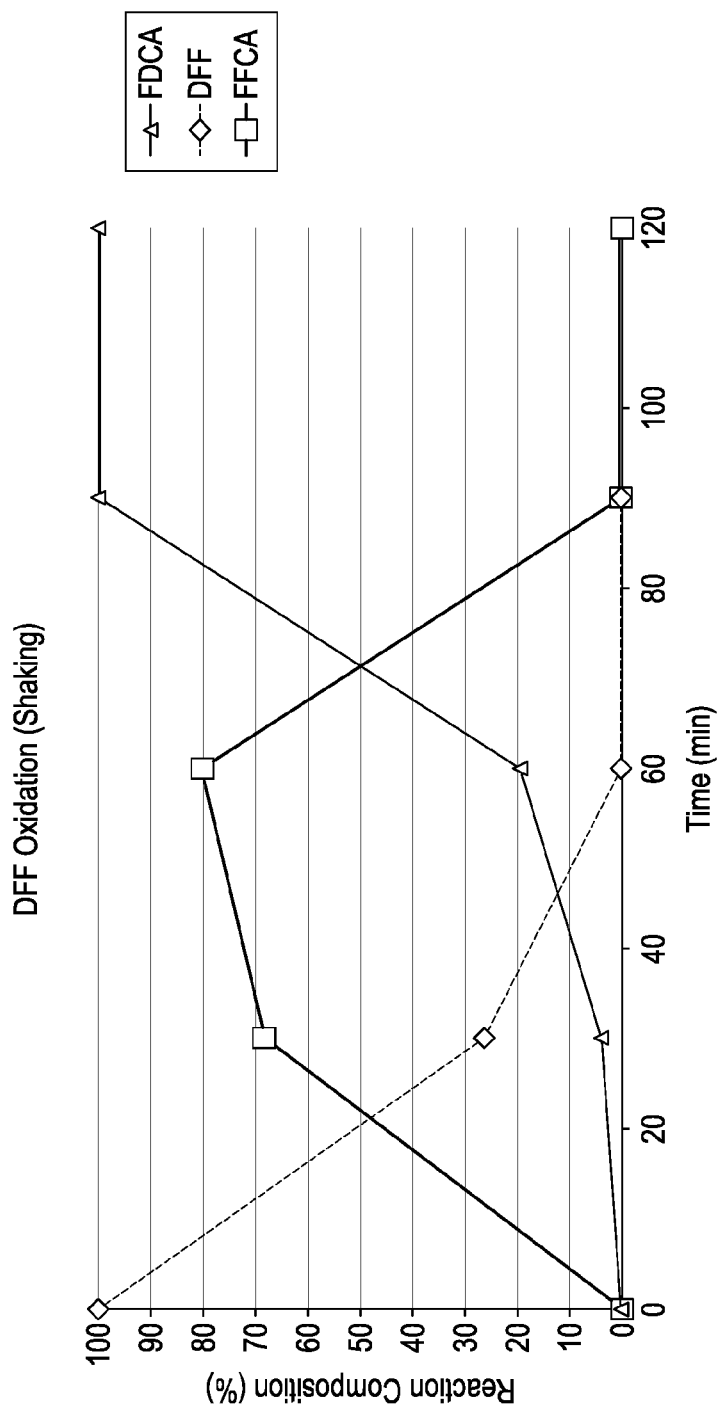

FIG. 14 shows the relative amount of DFF, FFCA and 2,5-FDCA as a function of time during the process described in Example 6. DFF was consumed in about 60 minutes with complete conversion of DFF to 2,5-FDCA taking about 90 minutes.

Figure 15:
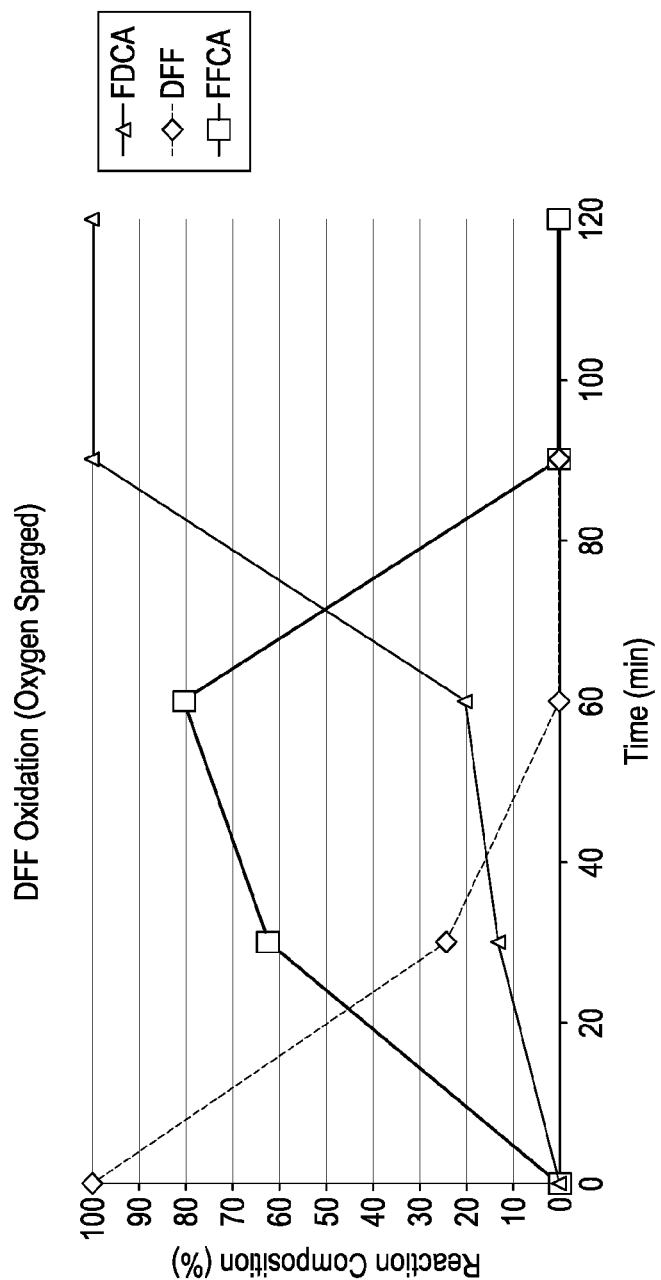

FIG. 15 shows the relative amount of DFF, FFCA and 2,5-FDCA as a function of time during the process described in Example 7. DFF was consumed in about 60 minutes with complete conversion of DFF to 2,5-FDCA taking about 90 minutes.

Figure 16:
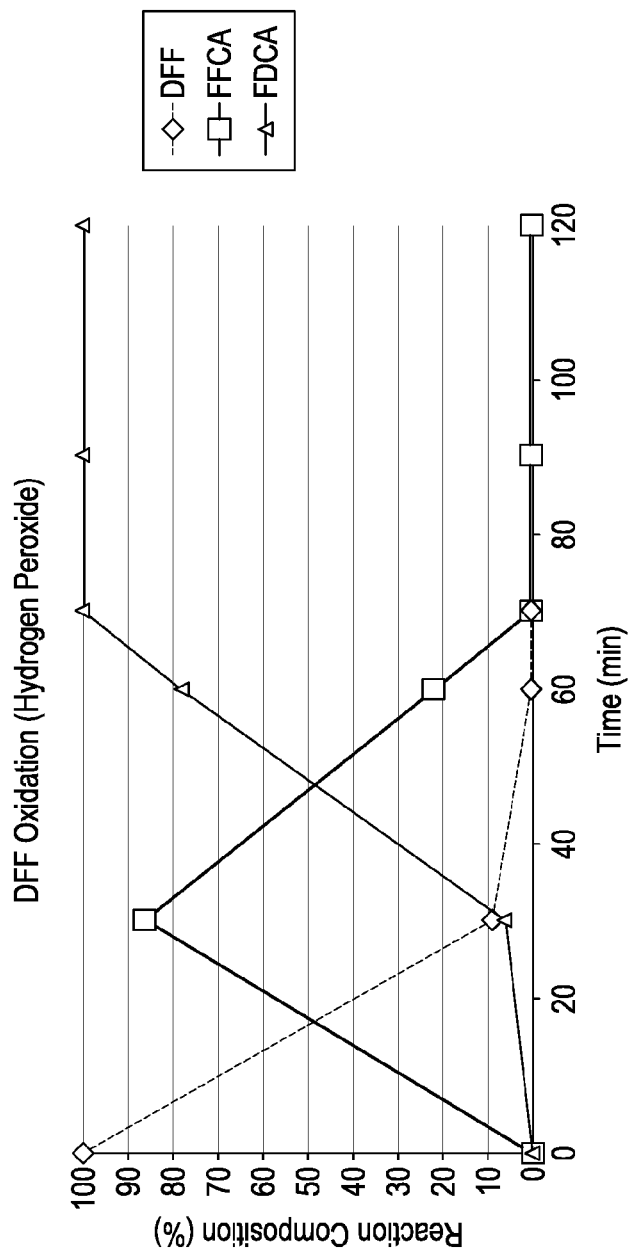

FIG. 16 shows the relative amount of DFF, FFCA and 2,5-FDCA as a function of time during the process described in Example 8 in which $H_2O_2$ was added to the reaction periodically. DFF was consumed in about 60 minutes with complete conversion of DFF to 2,5-FDCA taking about 65 minutes.

Figure 17:
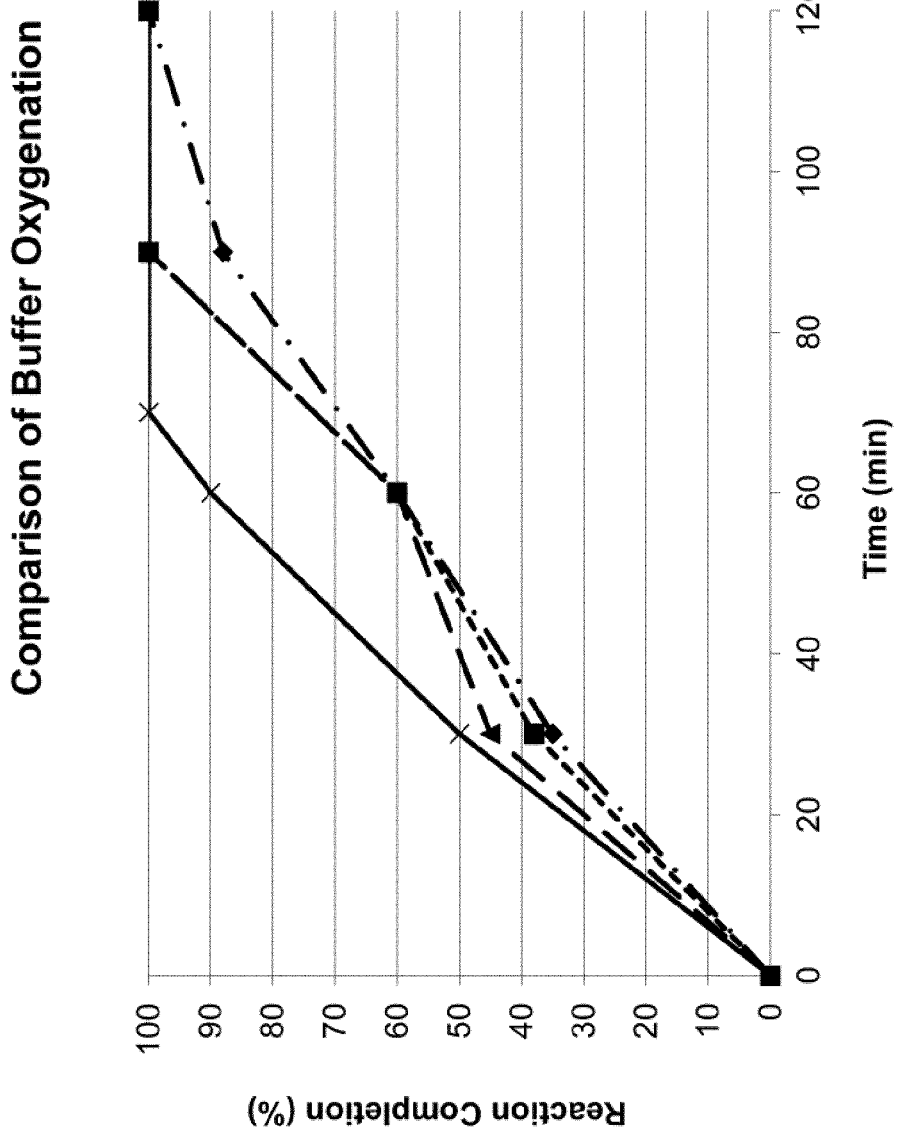

FIG. 17 shows the relative formation of 2,5-FDCA as a function of time during the process described in Examples 5 to 8. Initial shaking of the buffer solution (Example 6), and initial sparging of the reaction mixture with oxygen/air (Example 7), provided complete conversion of DFF to 2,5-FDCA in about 90 minutes, which was faster than the standard process (Example 5). Periodic addition of $H_2O_2$ to the reaction mixture (Example 8) provided complete conversion of DFF to 2,5-FDCA in about 65 minutes.

Figure 18:
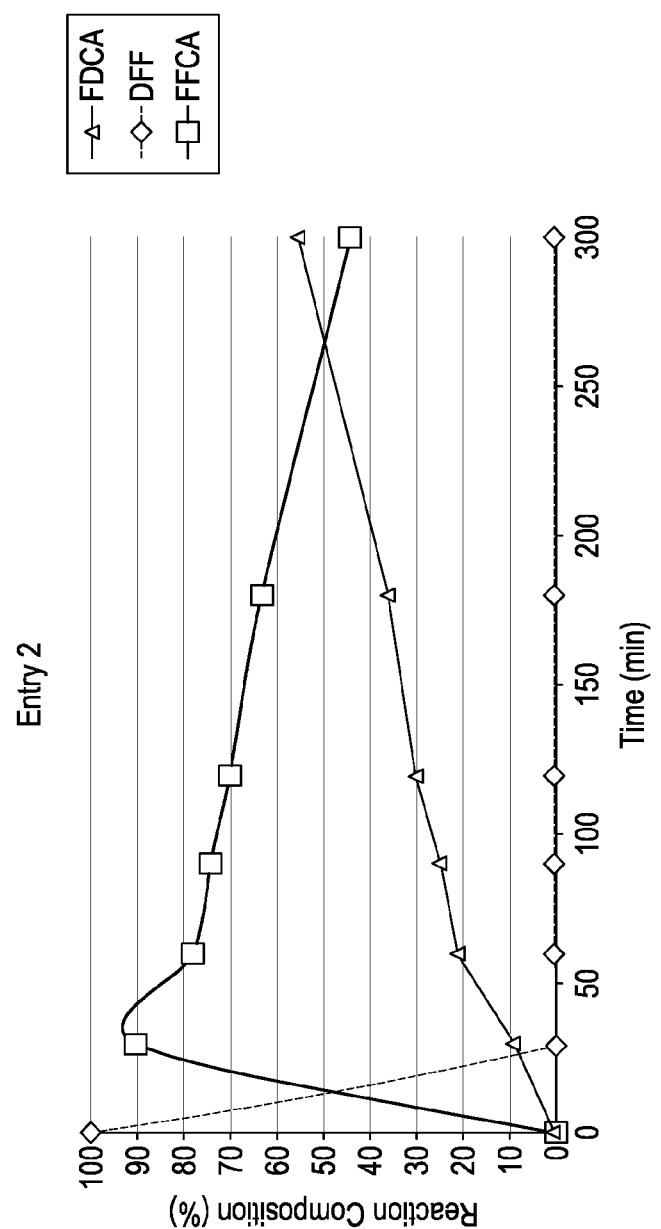

FIG. 18 shows the relative amount of DFF, FFCA and 2,5-FDCA as a function of time during the process described in Table 7, Entry 2, of Example 9, using ALD-003 CFE and 30 mol % NAD$^+$. The graph shows DFF is converted into FFCA rapidly, and 2,5-FDCA is formed in 56% conversion by 300 minutes.

Figure 19:
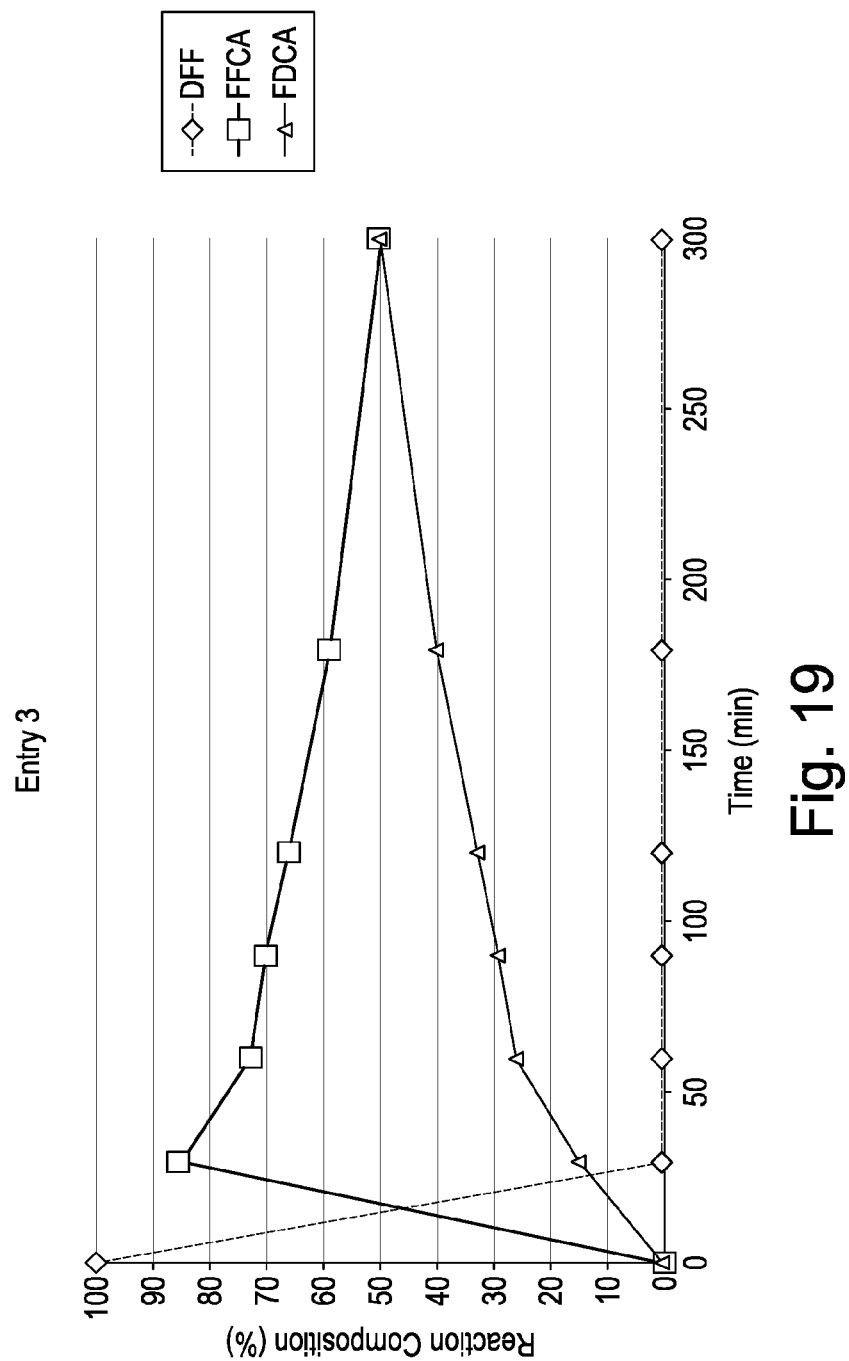

FIG. 19 shows the relative amount of DFF, FFCA and 2,5-FDCA as a function of time during the process described in Table 7, Entry 3, of Example 9, using ALD-003 CFE and 30 mol % NAD$^+$. The graph shows DFF is converted into FFCA rapidly, and 2,5-FDCA is formed in 50% conversion by 300 minutes.

Figure 20:
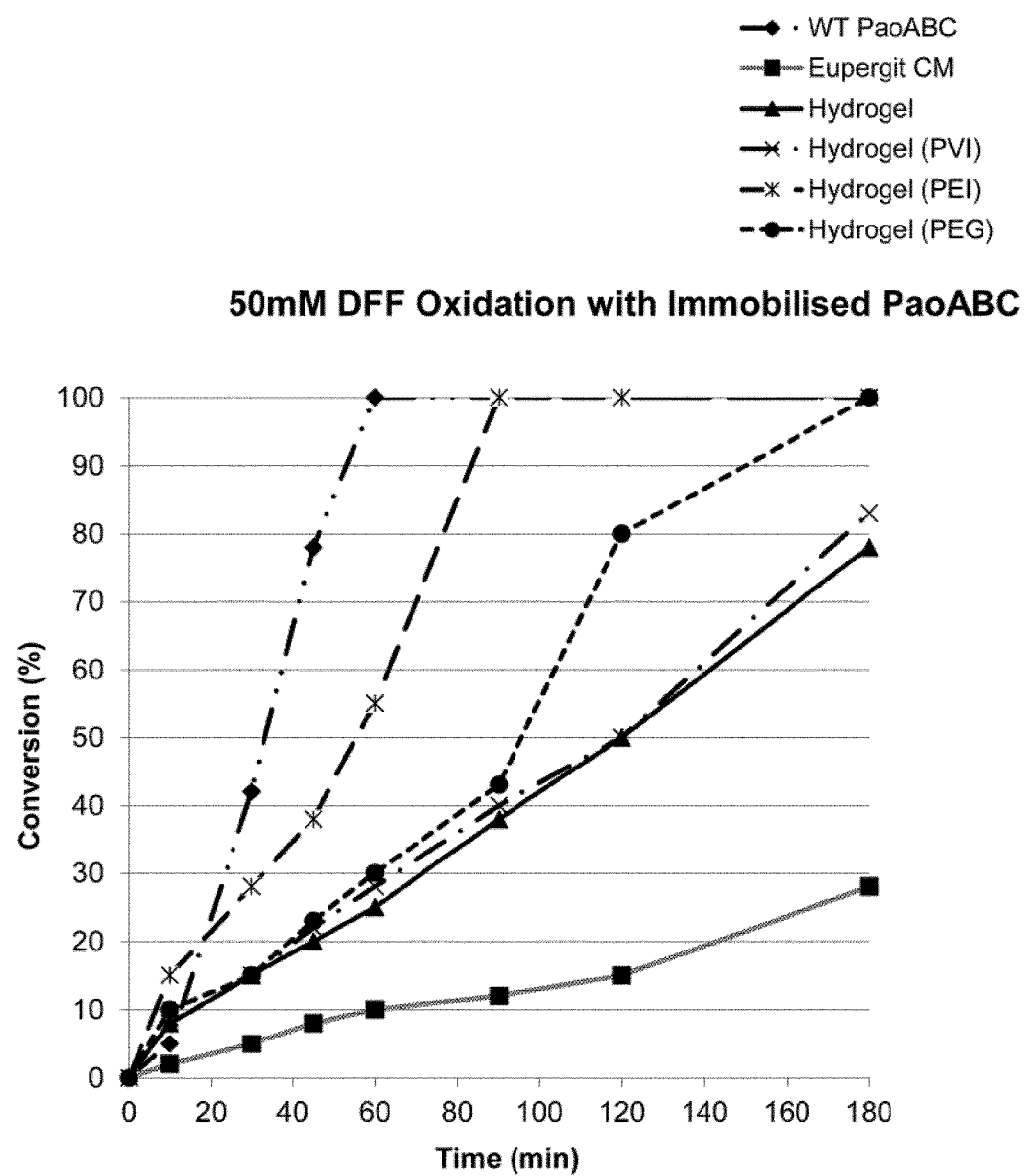

FIG. 20 shows the relative amount of 2,5-FDCA formed from DFF as a function of time using immobilised PaoABC as described in Example 11. Hydrogel-immobilised PaoABC is particularly useful in the formation of 2,5-FDCA from DFF with a rate of formation of 2,5-FDCA approaching that of wild-type (WT) PaoABC (free enzyme).

Figure 21:
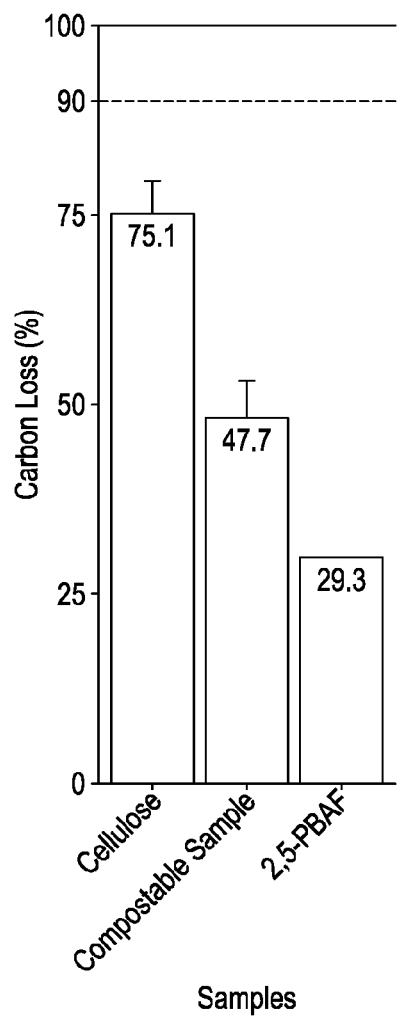

FIG. 21 shows that under the biodegradation test conditions outlined in Example 18, 2,5-PBAF result in a carbon loss of 29.3% after 40 days. The 90% level set for biodegradation in the test accounts for a +/−10% statistical variability of the experimental measurement, which one would expect virtually complete biodegradation in the composting environment of the test.

Figure 22:
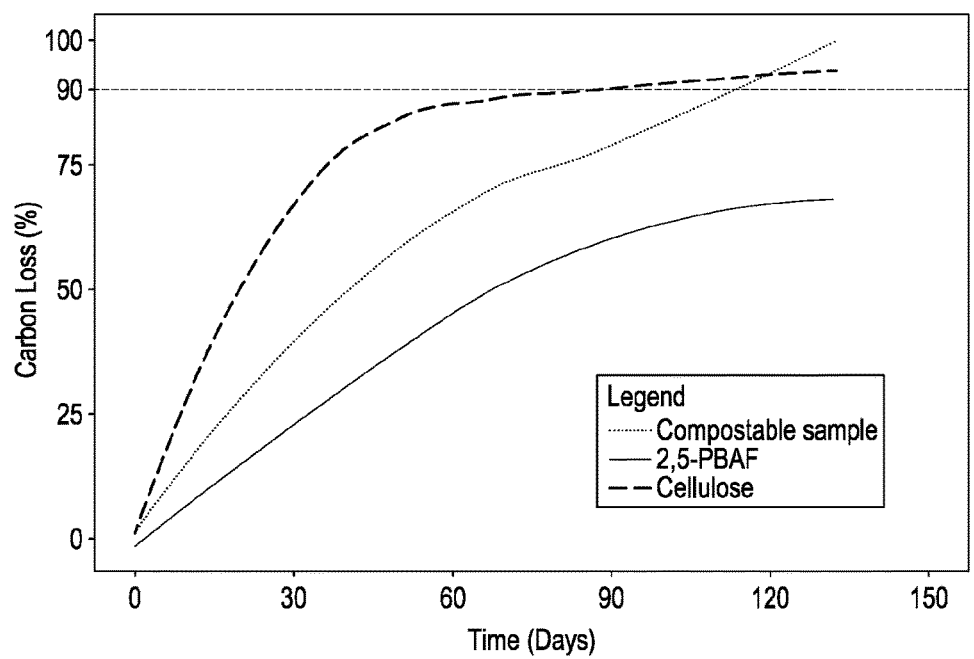

FIG. 22 shows that under the biodegradation test conditions outlined in Example 10, 2,5-PBAF loses carbon at a steady rate for over 60 days. The 90% level is as defined for FIG. 21 above.

Figure 23:
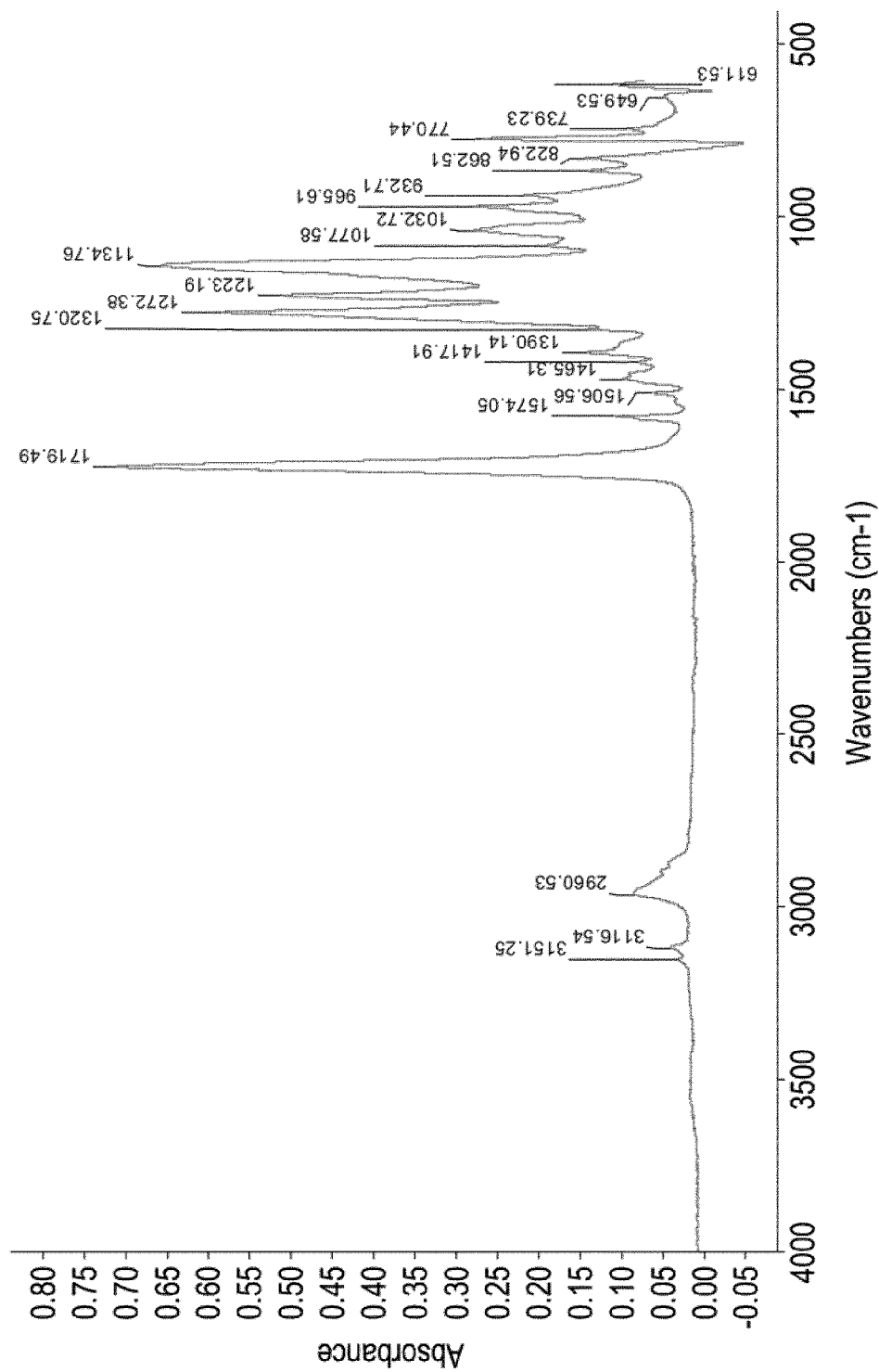

FIG. 23 shows the attenuated total reflectance Fourier transform infrared spectra (ATR-FTIR) of 2,5-polybutyrate adipate furandicarboxylate (2,5-PBAF) using a Thermo Nicolet Nexus FT-IR spectrometer coupled with a Continuum IR microscope.

Figure 24:
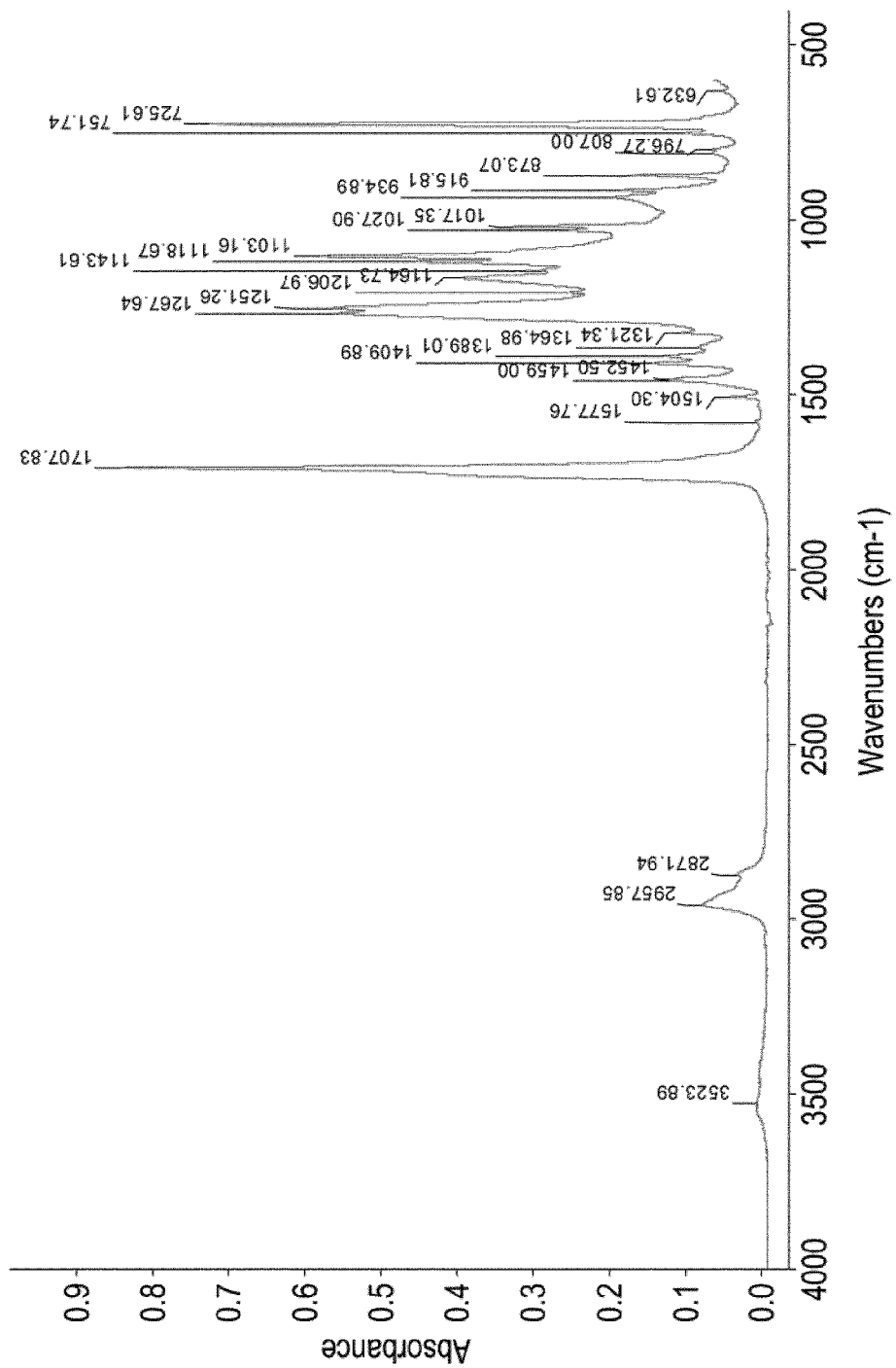

FIG. 24 shows the attenuated total reflectance Fourier transform infrared spectra (ATR-FTIR) of commercial PBAT using a Thermo Nicolet Nexus FT-IR spectrometer coupled with a Continuum IR microscope.

Figure 25:
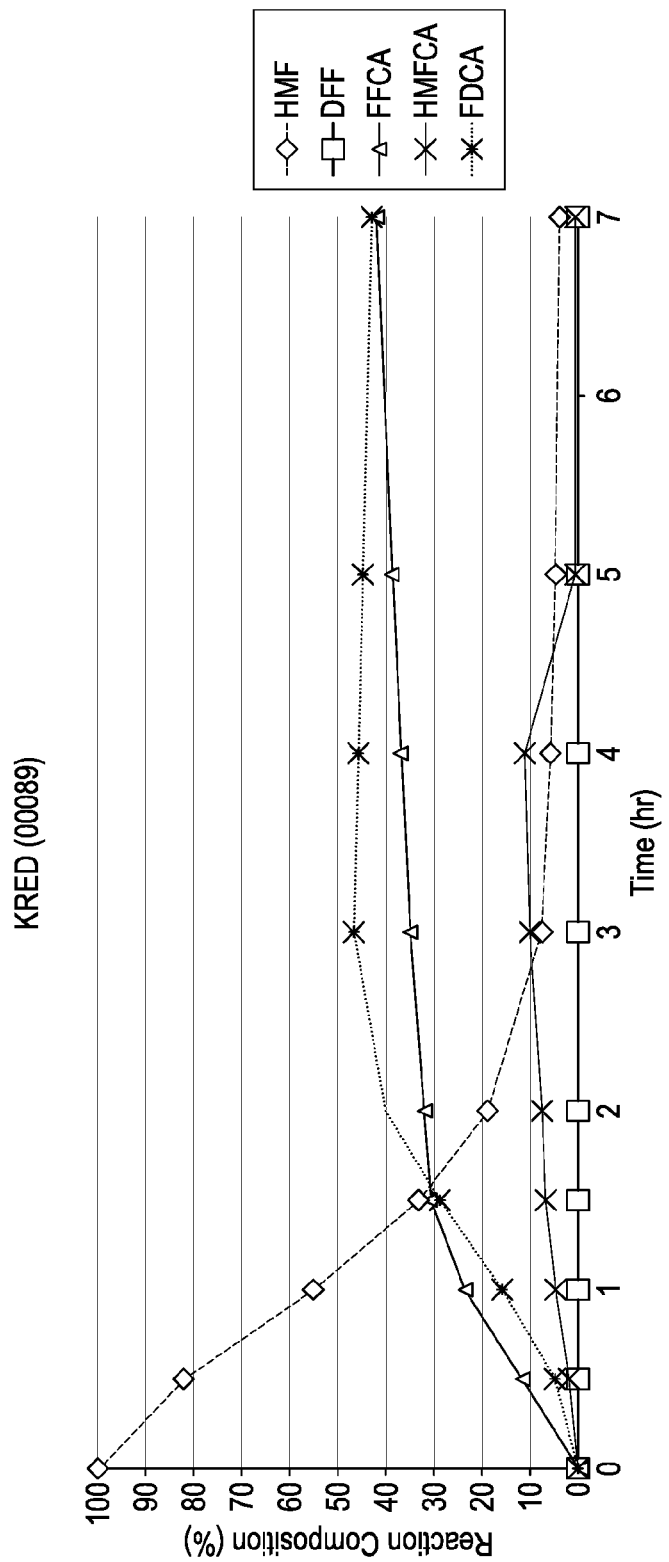

FIG. 25 shows the relative amount of HMF, 2,5-FDCA, HMFCA, DFF, and FFCA as a function of time during the process described in Example 9B. 2,5-FDCA starts to form at the start of the reaction and peaks at just under 50% conversion after three ours. The amount of FFCA increases rapidly over the first 1 to 1.5 hours and then slows. After 7 hours almost all of the HMF has been consumed.

The following examples are merely illustrative examples of the invention described herein, and are not intended to be limiting upon the scope of the invention.

Any listing or discussion of an apparently prior-published document in this specification should not necessarily be taken as an acknowledgement that the document is part of the state of the art or common general knowledge. All references disclosed herein are to be considered to be incorporated herein by reference.

EXAMPLES

Aldehyde dehydrogenase 3 (ALD-003) is a preferred aldehyde dehydrogenase, and is available from Prozomix Limited, Station Court, Haltwhistle, Northumberland, NE49 9HN, UK (catalogue name: Pro-ALDH (003)).

Ketoreductase 20 (KRED-020), KRED-089, KRED-141, KRED-143, KRED-163, and KRED-190 are preferred ketoreductases. KRED-089 is a preferred ketoreductase. These KREDs are available from Prozomix Limited, Station Court, Haltwhistle, Northumberland, NE49 9HN, UK, as an Aldo-Keto Reductase Panel (product name kREDy-to-go (AKR/ADH; kit of 96 enzymes); catalogue no. PRO-AKRP (MTP)).

Example 1

The following is an example of one of ways in which 2,5-furandicarboxylic acids (2,5-FDCA) may be formed from 5-hydroxymethylfurfural (HMF).

Synthesis of 2,5-furandicarboxylic Acid (2,5-FDCA)

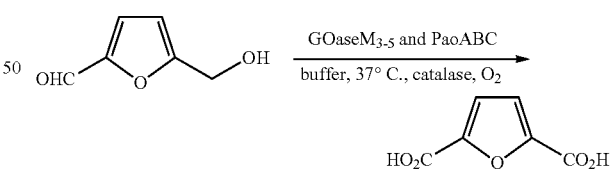

General Experimental Information and Materials

The *E. coli* TP1000 mutant strain used for PaoABC expression is a derivative of MC4100 with a kanamycin cassette inserted in the mobAB gene region. *E. coli* xanthine dehydrogenase and catalase were sourced from Sigma-Aldrich. Starting materials were purchased from Alfa Aesar and Sigma-Aldrich and used as received. HPLC analysis was performed on an Agilent 1200 system equipped with a G1379A degasser, G1312A binary pump, a G1329 autosampler unit, a G1315B diode array detector and a G1316A temperature controlled column compartment. The columns used were Thermofisher Hypurity C18 (5 μm particle size, 4.6 mm diameter×250 mm), Thermofisher ODS Hypersil C18 (5 μm particle size, 4.6 mm diameter×250 mm) and Bio-Rad Aminex HPX-87H, 300 mm×7.8 mm pre-packed column. GC analysis was performed on an Agilent 7890A chromatograph using an Alltech SE-30, 30.0 m×320 μm×0.25 μm column. Conditions are indicated separately for each compound. $^1$H NMR spectra were recorded on a Bruker Avance 400 or 500 without additional internal standard.

Preparation of Biocatalysts

Galactose Oxidase Variant $M_{3-5}$ (GOase $M_{3-5}$)

GOase mutant $M_{3-5}$ (Escalettes; Turner *J. ChemBioChem* 2008, 9, 857-860) was transformed into *E. coli* BL21 Star™ (DE3) cells (Invitrogen) according to manufacturer's specifications. A single colony was picked from an overnight LB plate containing 1 μL of kanamycin of a 30 mg/mL stock solution per mL of agar and used to inoculate 5 mL LB medium supplemented with 5 μL kanamycin and grown overnight at 37° C. and 250 rpm. 500 μL of the overnight culture was used to inoculate 250 mL of an autoinduction medium (8ZY-4LAC) as described by Deacon and McPherson (Deacon; McPherson *J. ChemBioChem*. 2011, 12, 593-601) and supplemented with 250 μL of kanamycin in a 2-L-baffled Erlenmeyer flask. The cells were grown at 26° C. and 250 rpm for 60 hour. Cells were harvested by centrifugation at 6,000 rpm and 40° C. for 20 min and subsequently prepared for protein purification.

Purification of GOase $M_{3-5}$

The cell pellet from a 250-mL-culture was resuspended in 30 mL lysis buffer containing 50 mM piperazine-N,N'-bis (2-ethanesulfonic acid) (PIPES), 25% sucrose (w/v), 1 mg mL$^{-1}$ lysozyme, 5 mM $MnCl_2$ and 1% Triton X-100 (v/v). The suspension was gently shaken at 4° C. for 20 min. Afterwards, cells were mechanically disrupted via ultrasonication (30 sec. on, 30 sec. off; 20 cycles) followed by ultracentrifugation (20,000×g, 30 min, 4° C.). The cleared crude extract was transferred into a flexible tubing (30 kDa cut-off), dialysed into buffer C (50 mM NaPi buffer, 300 mM NaCl, pH 8.0) for 12 hours at 4° C. and subsequently passed through a syringe filter with a 0.22 μm pore size. Protein purification was accomplished with a peristaltic tubing pump (Thermo Scientific) equipped with a 5-mL-Strep-Tag®-II column (GE Healthcare) pre-equilibrated with buffer C. After loading with crude extract, the column was washed with 5 column volumes of buffer C followed by protein elution with 70 mL of buffer D (50 mM NaPi buffer, 300 mM NaCl, 5 mM desthiobiotin, pH 8.0).

For copper-loading, GOase $M_{3-5}$-containing fractions were pooled and subsequently transferred into flexible dialysis tubing (30 kDa cut-off) and dialysed twice for 12 hours into buffer E (50 mM NaPi buffer saturated with $CuSO_4$, pH 7.4) at 4° C. Removal of excess $CuSO_4$ was attained by two cycles of dialysis into buffer E (without $CuSO_4$) for 12 hours at 4° C. and protein samples concentrated to approximately 3 mg/mL using a Sartorius Vivaspin 6 spin column (30 kDa mass cut-off). The protein samples were aliquoted and the aliquots were frozen in liquid nitrogen prior to storage at −80° C.

*E. coli* Perisplasmic Aldehyde Oxidase (PaoABC)

For PaoABC expression (Neumann et al. *FEBS Journal* 2009, 276, 2762-2774), the plasmid pMN100 derived from pTrcHisA (Invitrogen), containing the PaoABC genes with a His6 tag fused to the N-terminus of PaoA, was used. For heterologous expression in *E. coli*, pMN100 was transformed into *E. coli* TP1000 cells, containing a deletion in the mobAB genes responsible for Moco dinucleotide formation. One liter of LB supplemented with 1 mM sodium molybdate and 10 μM isopropyl thio-β-D-galactoside was inoculated with 2 mL of an overnight culture and incubated for 24 hours at 22° C. and 100 rpm. The cells were harvested by centrifugation at 4,000×g for 15 min.

Purification of PaoABC

The cell pellet was resuspended in 8 volumes of 50 mM sodium phosphate, 300 mM NaCl, pH 8.0, 10 mM imidazole and cell lysis was achieved by sonication (MSE Soniprep) with cooling on ice (20 bursts of 20 s on/off at 14 u). After addition of DNase I, the lysate was incubated for 30 min. After centrifugation at 17,000×g for 25 min the supernatant was filtered through 0.45 and 0.2 μM membranes before loading onto $Ni_2$-nitrilotriacetic agarose (HiTrap 1 mL column (GE Healthcare)). The column was washed with 2 column volumes of 10 mM imidazole, 50 mM sodium phosphate, 300 mM NaCl, pH 8.0, followed by a wash with 10 column volumes of the same buffer with 20 mM imidazole. His-tagged PaoABC was eluted with 20 mL of 100 mM imidazole in 50 mM sodium phosphate, 300 mM NaCl, pH 8.0. Fractions containing PaoABC were buffer exchanged into 50 mM Tris, 1 mM EDTA, pH 7.5. The yield of protein was about 13 mg/L of *E. coli* culture.

Xanthine Dehydrogenase Variants E232V and E232VR310 (XDH E232V, XDH E232VR310)

For expression of XDH mutants, the plasmid pSL207 derived from pTrcHisA (Invitrogen), containing the xdh genes with a His6 tag fused to the N-terminus of XDHA, was used. For heterologous expression in *E. coli*, pSL207 was transformed into *E. coli* TP1000 cells, containing a deletion in the mobAB genes responsible for Moco dinucleotide formation. The enzyme was expressed in 500-mL-cultures of TP1000 cells carrying plasmid pSL207 grown at 30° C. in LB medium supplemented with 150 μg/mL ampicillin, 1 mM molybdate, and 0.02 mM isopropyl-D-thiogalactopyranoside until the $OD_{600\ nm}$=1. This culture was then transferred to a bottle containing 8 L of supplemented LB medium and subsequently grown at 30° C. for 18 to 20 hours. Cells were harvested by centrifugation at 5000×g at 4° C. and subsequently prepared for protein purification.

Purification of XDH E232V and XDH E232VR310

The cell pellet was resuspended in eight volumes of 50 mM sodium phosphate, 300 mM NaCl, pH 8.0, and cell lysis was achieved by several passages through a French press. After addition of DNase I, the lysate was incubated for 30 min. After centrifugation at 17,000×g for 25 min, imidazole was added to the supernatant to a final concentration of 10 mM. The supernatant was mixed with 2 mL of $Ni_2$-nitrilotriacetic agarose (Qiagen) per liter of cell growth, and the slurry was equilibrated with gentle stirring at 4° C. for 30 min. The slurry was poured into a column, and the resin was washed with two column volumes of 10 mM imidazole, 50 mM sodium phosphate, 300 mM NaCl, pH 8.0, followed by a wash with ten column volumes of the same buffer with 20 mM imidazole. His-tagged XDH was eluted with 100 mM imidazole in 50 mM sodium phosphate, 300 mM NaCl, pH 8.0. Fractions containing XDH were combined and dialyzed against 50 mM Tris, 1 mM EDTA, 2.5 mM dithiothreitol, pH 7.5. The dialyzed sample was applied to a Q-Sepharose fast protein liquid chromatography column and eluted with a linear gradient of 0-250 mM NaCl. To the pool of fractions containing XDH, 15% ammonium sulphate was added, and the protein was then applied to a phenyl-Sepharose column equilibrated with 50 mM Tris, 1 mM EDTA, 2.5 mM dithiothreitol, 15% ammonium sulphate, pH 7.5. XDH E232V was eluted from the column with a linear gradient of from 15 to 0% ammonium sulphate. During purification, fractions were monitored using SDS-PAGE, whereas enzyme activity was measured spectrophotometrically as described above.

Screening of Xanthine Oxidoreductases for Oxidation of HMF, DFF and FFCA

XORs were screened using potassium phosphate buffer (50 mM, pH 7.6), 3 μL 0.1 M HMF (in MeCN), 30 μL 0.01 M DCPIP (aq.) final volume 300 μL, 36° C. When DCPIP was the oxidant, activity was determined by the colour change from blue to colourless; when $O_2$ was the oxidant, activity was detected using NBT assay (Agarwal; Banerjee Open Biotech J. 2009, 3, 46-49). The results can be found in Table 1.

TABLE 1

Screening of xanthine oxidoreductases

| Enzyme | HMF | DFF | FFCA | Oxidant |
|---|---|---|---|---|
| E. coli XDH[a] | Active | — | — | $O_2$ |
| XDH E232V[b] | Active | Active | Active | DCPIP |
| XDH E232V R310[c] | Active | Active | Active | DCPIP |
| PaoABC[d] | Active | Active | Active | $O_2$ |

[a]E. coli XDH (1.1 mg/mL);
[b]XDH E232V (25.4 mg/mL);
[c]XDH E232V/R310M (23 mg/mL);
[d]PaoABC (13.3 mg/mL);
[e]PaoABC (13.3 mg/mL).

Optimisation of the HMF 2-Step Oxidation Cascade

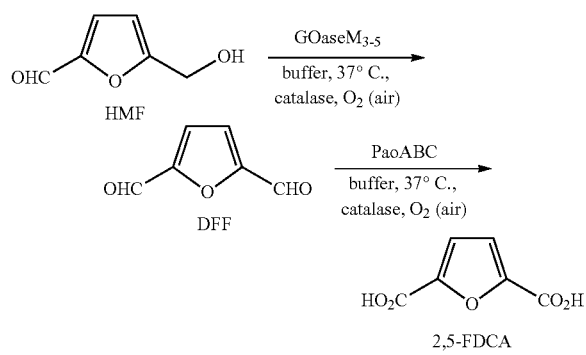

GOase $M_{3-5}$ (3.3 mg/mL; 103 μL), catalase (3.3 mg/mL; 33 μL), HMF (3 μL of a solution defined in Table 2 in MeCN), potassium phosphate buffer (concentration as per Table 2, pH 7.6) were combined and made up to 300 μL. After full conversion of HMF to DFF, PaoABC (13.3 mg/mL; 5 μL) was added. Formation of DFF was monitored via RP-HPLC using a Thermofisher Hypurity C18 column with flow rate 0.6 mL/min using 85% water+0.1% Acetic acid and 15% MeCN. Formation of 2,5-FDCA was monitored via RP-HPLC using a Thermofisher Hypurity C18 column with flow rate 1 mL/min using a 98% 10 mM phosphate buffer (pH 6.5) and 2% MeCN mobile phase. The results can be found in Table 2.

TABLE 2

Optimisation of the HMF multistep oxidation cascade

| Entry | HMF mM | pH | Buffer mM | DFF % | 2,5-FDCA % |
|---|---|---|---|---|---|
| 1[a] | 10 | 7.5 | 50 | — | 97 |
| 2[a] | 20 | 7.5 | 50 | — | 55 |
| 3 | 20 | 7.5 | 50 | >99 | >99 |
| 4 | 30 | 7.5 | 50 | >99 | >99 |
| 5 | 50 | 7.5 | 50 | >99 | 0 |
| 6 | 50 | 7.5 | 100 | >99 | >99 |
| 7 | 70 | 7 | 300 | >99 | >99 (80[c]) |
| 8 | 100 | 7 | 400 | >99 | 0 |
| 9[b] | 100 | 7 | 400 | >99 | >99 |
| 10[b] | 100 | 7 | 400 | 0 | >99 (74[c]) |

[a]One-pot reactions with all enzymes present.
[b]Additional catalase was added with PaoABC.
[c]Reactions on a preparative scale.

Optimisation of Conversion of DFF to 2,5-FDCA

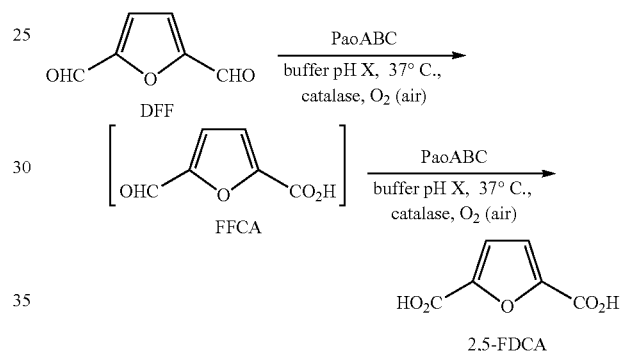

To a solution of potassium phosphate buffer was added DFF (2 M in MeCN; 33 μL), catalase (3.3 mg/mL) and PaoABC (13.3 mg/mL). The final volume was 300 μL. The reaction was vigorously shaken and placed in a shaking incubator at 37° C. Aliquots of the reaction mixture were removed, acidified with 2 M HCl and analysed by RP HPLC using a Thermo Fisher Hypurity C18 column, 98% 10 mM phosphate buffer pH 6.5, 2% MeCN with a flow rate of 1 mL/min. The results can be found in Table 3.

TABLE 3

Optimisation of conversion of DFF to 2,5-FDCA

| Entry | DFF mM | pH[c] | Buffer mM | PaoABC μL | Time hours | 2,5-FFCA % | 2,5-FDCA[b] % |
|---|---|---|---|---|---|---|---|
| 1 | 50 | 6 | 200 | 5 | 2 | 100 | 0 |
| 2 | 50 | 7 | 200 | 5 | 2 | 0 | >99 |
| 3 | 50 | 8 | 200 | 5 | 2 | 0 | >99 |
| 4 | 50 | 9 | 200 | 5 | 2 | 18 | 0 |
| 5 | 80 | 7 | 200 | 5 | 4 | 0 | >99 |
| 6 | 80 | 8 | 200 | 5 | 4 | 0 | 66 |
| 7[a] | 100 | 7 | 200 | 5 | 16 | 40 | 60 |
| 8 | 100 | 7 | 400 | 5 | 8 | 0 | >99 |

[a]pH 4.5 after 16 hours.
[b]Conversion adjusted by analysing a 1:1 standard of the aldehyde:acid by $^1$H NMR and comparing the HPLC trace of the same sample and adjusting the absorbance accordingly.
[c]Initial pH.

Preparative Scale Oxidation of DFF with PaoABC

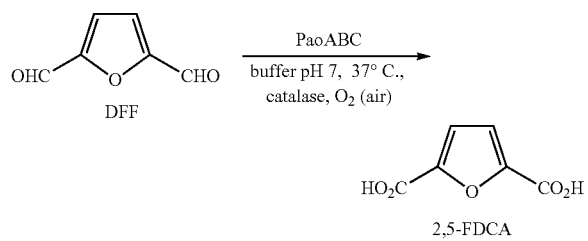

To a solution of phosphate buffer (400 mM; pH 7) was added DFF (37 mg, 0.29 mmol), catalase (3.3 mg/mL; 330 μL), MeCN (150 μL) and PaoABC (13.3 mg/mL; 50 μL). The final volume was 3 mL. The reaction was vigorously shaken and placed in a shaking incubator at 37° C. The pH was maintained at pH 7 by the addition of 1 M NaOH. The reaction was heated to 80° C. for 5 minutes and left cool to ambient temperature. The solution containing denatured protein was centrifuged and the supernatant removed. The supernatant was then cooled to 0° C. and concentrated HCl was added until a precipitate formed. The solution was then centrifuged, the supernatant removed and the resulting pellet washed with 1 M HCl. The pellet was dissolved in acetone and then concentrated in vacuo (×3) to form 2,5-FDCA as a slightly yellow solid (41 mg, 0.26 mmol, 90%). $^1$H NMR (500 MHz, DMSO-d6) δ ppm: 13.63 (b s, 2H), 7.29 (s, 2H); $^{13}$C NMR (125 MHz, DMSO-d6) δ ppm: 159.4, 147.5, 118.86.

Preparative Scale Synthesis of FDCA

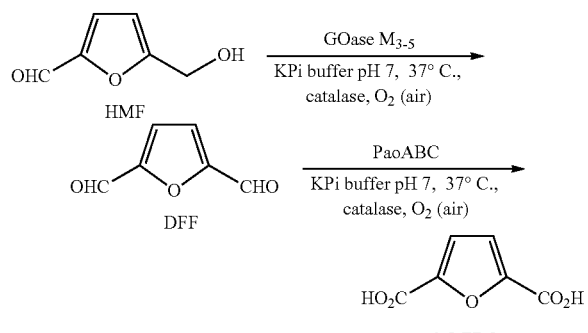

To a solution of potassium phosphate buffer (400 mM; pH 7; 1.09 mL), MeCN (0.03 mL) and catalase (0.33 mL of a 3.3 mg/mL solution) was added HMF (38 mg, 0.3 mmol; final concentration 100 mM). GOase M$_{3-5}$ (1.5 mL of a 3.3 mg/mL solution) was added and the reaction shaken at 37° C. in an incubated shaker for 10 hours. Another portion of catalase (0.33 mL of a 3.3 mg/mL solution) was then added, together with PaoABC (0.05 mL of a 13.2 mg/mL solution). The reaction was left for another 5 hours in the shaking incubator. The pH was carefully monitored and adjusted to pH 7 with 1 M NaOH. The reaction was heated to 80° C. for 5 minutes and left to cool to ambient temperature. The solution containing denatured protein was centrifuged and the supernatant removed. The supernatant was then cooled to 0° C. and concentrated HCl was added until a precipitate formed. The solution was then centrifuged and the supernatant removed and the pellet washed with 1M HCl. The pellet was dissolved in acetone and then concentrated in vacuo (×3) to form 2,5-FDCA as a slight yellow solid (35 mg, 0.22 mmol, 74% yield). $^1$H NMR (500 MHz, DMSO-d6) δ ppm: 13.63 (b s, 2H), 7.29 (s, 2H); $^{13}$C NMR (125 MHz, DMSO-d6) δ ppm: 159.4, 147.5, 118.86.

Example 2

Figure 11:
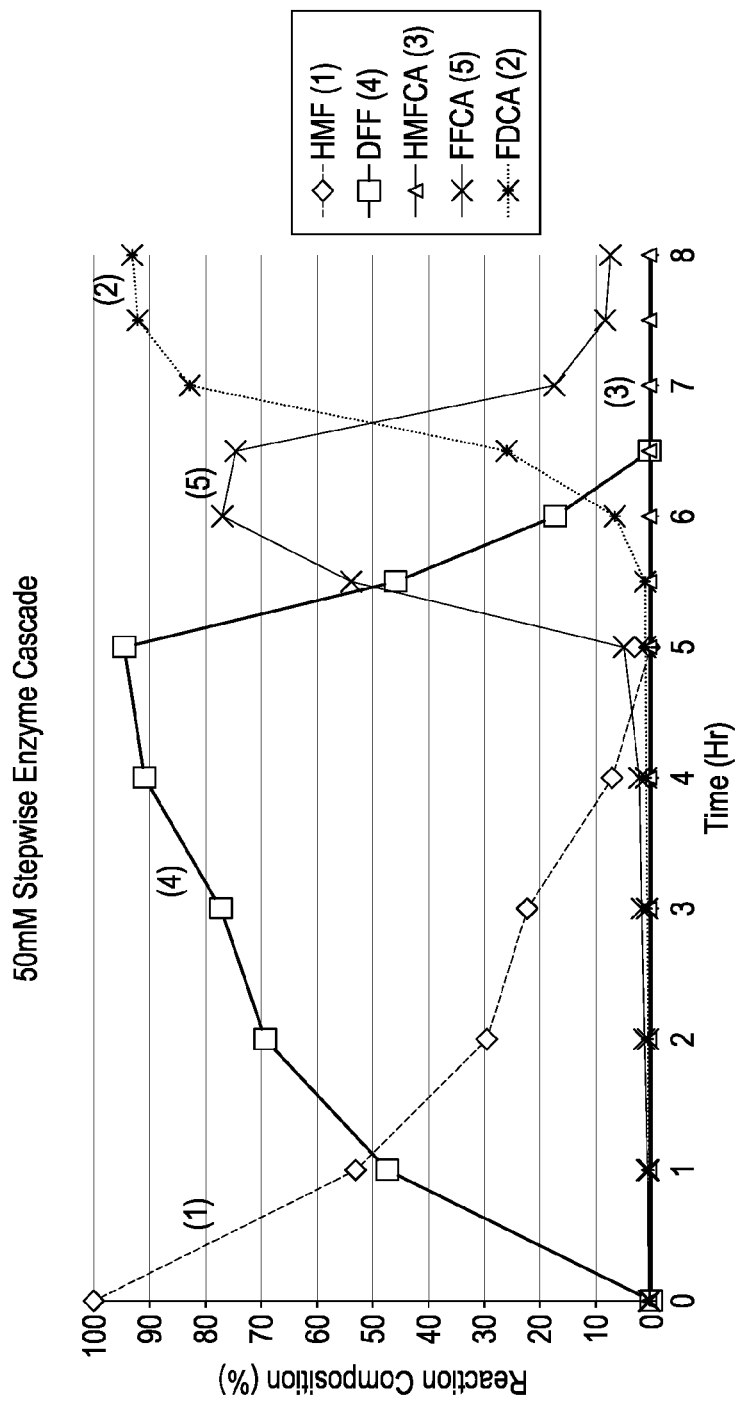
FIG. 11 shows the relative amount of HMF (1), 2,5-FDCA (2), HMFCA (3), DFF (4), and FFCA (5) as a function of time during the process described in Example 2. PaoABC was added after 5 hours.

HMF (1.9 mg, 0.015 mmol, final concentration=50 mM) and catalase (0.033 mL of a 3.3 mg mL$^{-1}$ solution) were added to KPi buffer (400 mM pH 7) (0.109 mL) and MeCN (0.003 mL). GOase M$_{3-5}$ (0.15 mL of a 3.3 mg mL$^{-1}$ solution) was then added and the reaction shaken at 37° C. for 5 hours in a shaking incubator. PaoABC (0.005 mL of a 13.2 mg mL$^{-1}$ solution) was added and the reaction shaken for a further 3 hours in the incubator. The pH was monitored and adjusted to pH 7 with 1 M NaOH. The reaction was heated to 80° C. for 5 minutes and left to cool. The solution containing denatured protein was centrifuged and the supernatant removed and analysed by RP-HPLC (see FIG. 11).

HMF is converted into DFF during the first five hours of the reaction. The addition of PaoABC to the reaction rapidly converts DFF into 2,5-FDCA.

Example 3

Figure 12:
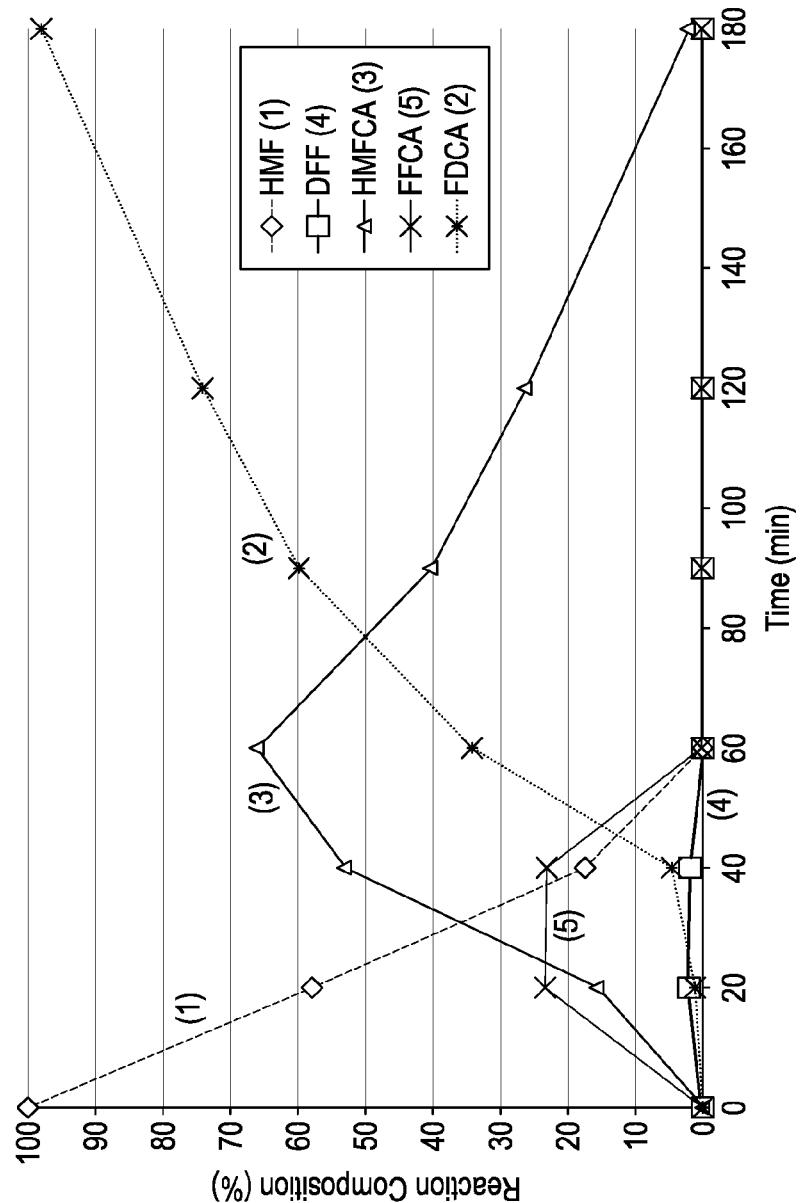
FIG. 12 shows the relative amount of HMF (1), 2,5-FDCA (2), HMFCA (3), DFF (4), and FFCA (5) as a function of time during the process described in Example 3.

HMF (final concentration 50 mM), GOase M$_{3-5}$ (103 μL of 3 mg/mL), PaoABC (1 μL of 28.9 mg/mL), catalase (33 μL of 3.3 mg/mL) and horseradish peroxidase (HRP) (70 μL of 1 mg/mL) were combined in KPi buffer (500 mM) at 37° C. and the pH continuously adjusted with 2M NaOH to give a conversion of 93-100% of 2,5-FDCA. The reaction was heated to 80° C. for 5 minutes and left to cool. The solution containing denatured protein was centrifuged and the supernatant removed and analysed by RP-HPLC (see FIG. 12).

HMF may be converted into 2,5-FDCA via DFF or HMFCA under the reaction conditions. A peak of about 65% HMFCA after 60 minutes may indicate that the conversion of HMFCA into FFCA may be the rate limiting step.

Example 4

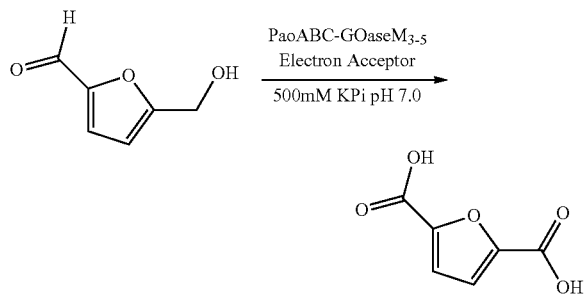

HMF (100 mM) was added to KPi buffer (500 mM pH 7.0). GOase M$_{3-5}$ (103 μl of 3.3 mg/mL), PaoABC (1 μl of 28.9 mg/mL) and a metal complex (see Table 4) were added at 37° C. and the pH was continuously adjusted with NaHCO$_3$ for a period of 16 hours. The reaction was heated to 80° C. for 5 minutes and left to cool. The solution containing denatured protein was centrifuged and the supernatant removed and analysed by RP-HPLC.

TABLE 4

| Entry | Metal complex (mol %[1]) (electron acceptor) | HMF (%[2]) | DFF (%[2]) | HMFCA (%[2]) | FFCA (%[2]) | 2,5-FDCA (%[2]) |
|---|---|---|---|---|---|---|
| 1 | V(II)acac (400%) | 0 | 0 | 90 | 7 | 3 |
| 2 | V(II)acac (100%) | 0 | 0 | 60 | 0 | 33 |
| 3 | V(II)acac (50%) | 0 | 0 | 56 | 0 | 36 |
| 4 | V(II)acac (10%) | 0 | 0 | 6.6 | 86 | 7.3 |
| 5 | Mn(III)acac(50%) | 0 | 0 | 86 | 14 | 0 |
| 6 | Fe(II)phthalocyanine (50%) | 23 | 9 | 7 | 60 | 1 |
| 7 | Fe(III)acac (50%) | 0 | 0 | 56 | 0 | 44 |
| 8 | Fe(III)EDTA (50%) | 0 | 0 | 0 | 0 | 0 |
| 9 | V(V)OEt$_3$ (50%) | 0 | 0 | 13 | 58 | 28 |
| 10 | V(V)OEt$_3$ (10%) | 0 | 0 | 3 | 52 | 45 |
| 11 | V(V)Oxide (50%) | 0 | 0 | 26 | 0 | 73 |
| 12 | Co(II,III)oxide (50%) | 0 | 49 | 3 | 46 | 1 |
| 13 | Fe(III)oxide (50%) | 3.4 | 44.6 | 5.8 | 45 | 0.7 |
| 14 | Vanadyl acac (50%) | 0 | 0 | 77.8 | 0 | 22.2 |
| 15 | VO(IV)sulphate (50%) | 0 | 0 | 22.3 | 0 | 77 |
| 16 | Hematin (50%) | 0 | 43 | 0 | 56 | 0 |
| 17 | Hemin (50%) | 0 | 60 | 0 | 40 | 0 |
| 18 | Mn(II)sulphate (50%) | 0 | 39 | 0 | 61 | 0 |

[1]mol % of metal complex based on the amount of HMF at the start of the reaction.
[2]percentage based upon calibration by NMR of equimolar mixtures.

Example 5—DFF Oxidation—Standard Process (No Shaking)

To 490 μL of 0.2M KPi buffer (pH 7.0) was added DFF (final concentration 100 mM) and 1 mg catalase. 10 μL of a 100 μM PaoABC was then added and the reaction was left in a shaking incubator. 5 μL of the reaction mixture was extracted, diluted with 80 μL of water and quenched with 15 μL 1M HCl. The aliquots were analysed by RP HPLC (see FIG. 13). Complete conversion of DFF to 2,5-FDCA required about 120 minutes.

Example 6—DFF Oxidation—Initial Shaking

To 490 μL of 0.2M KPi buffer (pH 7.0) was added DFF (final concentration 100 mM) and 1 mg catalase. The Eppendorf was vigorously shaken. 10 μL of a 100 μM PaoABC was then added and the reaction was left in a shaking incubator. 5 μL of the reaction mixture was extracted, diluted with 80 μL water and quenched with 15 μL 1M HCl. The aliquots were analysed by RP HPLC (see FIG. 14). Complete conversion of DFF to 2,5-FDCA required about 90 minutes.

Example 7—DFF Oxidation—Oxygen Sparged Buffer

To 490 μL of 0.2M KPi (pH 7.0), sparged with compressed air (HPLC filter) for 5 hours, was added DFF (final concentration 100 mM) and 1 mg catalase. 10 μL of a 100 μM PaoABC was then added and the reaction was left in a shaking incubator. 5 μL of the reaction mixture was extracted, diluted with 80 μL water and quenched with 15 μL 1M HCl. The aliquots were analysed by RP HPLC (see FIG. 15). Complete conversion of DFF to 2,5-FDCA required about 90 minutes.

Example 8—Periodic Hydrogen Peroxide Addition

To 490 μL of 0.2M KPi buffer (pH 7.0) was added DFF (final concentration 100 mM) and 1 mg catalase. 10 μL of a 100 μM PaoABC was then added and the reaction was left in a shaking incubator. 1 μl of a 1% $H_2O_2$ was added every 15 minutes. 5 μL of the reaction mixture was extracted, diluted with 80 μL of water and quenched with 15 μL 1M HCl. The aliquots were analysed by RP HPLC (see FIG. 16). Complete conversion of DFF to 2,5-FDCA required about 65 minutes.

Example 9A

ALD-003 (5 mg), NOX-009 or NOX-001 (5 mg) and $NAD^+$ or $NADP^+$ (20 mol % based upon the amount of ALD-003) was added to 0.5 mL 0.25M KPi (pH 8.5). The pH was adjusted to pH 8.5 with 1M NaOH. 10 mM DFF or HMF was added and the reaction was left in a shaking incubator at 35° C. After a specified time the reaction was quenched with 1M HCl, centrifuged and analysed by RP-HPLC. The results are found in Tables 5, 6, and 7A.

TABLE 5

| Entry | Enzyme | Substrate | Co-Factor | NOX | Conv Product |
|---|---|---|---|---|---|
| 1 | ALD-003 | HMF | NAD+ | NOX-009 | 100% HMFCA |
| 2 | " | HMF | NADP+ | NOX-001 | 100% HMFCA |
| 3 | " | DFF | NAD+ | NOX-009 | 100% FDCA |
| 4 | " | DFF | NADP+ | NOX-001 | 100% FDCA |

Reaction Conditions: 0.5 mL KPi 0.25M pH 8.5, 5 mg CFE, 20 mol % cofactor, 5 mg NOX, 10 mM Substrate, 35° C., reaction time 30 minutes.

TABLE 6

| Entry | Enzyme | [DFF] | Substrate | Nox | Time | FFCA | FDCA |
|---|---|---|---|---|---|---|---|
| 1 | ALD-003 | 50 | DFF | NOX-009 | 3 hr | 20% | 80% |
| 2 | " | 100 | " | NOX-009 | | 80% | 20% |

Reaction Conditions: 0.5 mL KPi 0.25M pH 8.5, 5 mg ALD-003 CFE, 30 μl catalase (3.3 mg/mL) 20 mol % cofactor, 5 mg NOX, 35° C.

TABLE 7A

| Entry | [DFF] | pH | NOX-009 (mg) | CFE (mg) | $NAD^+$ (mol %) | Yield DFF:FFCA:FDCA |
|---|---|---|---|---|---|---|
| 1 | 100 | 8.5 | 5 | 5 | 20% | 0:80:20 |
| 2 | " | " | " | " | 30% | 0:44:56 |
| 3 | " | " | " | " | 40% | 0:50:50 |

Reaction Conditions: 0.5 mL KPi 0.25M pH 8.5, 5 mg ALD-003 CFE, 30 μL catalase (3.3 mg/mL) Xmol % cofactor ($NAD^+$), 5 mg NOX, 35° C., reaction time 3 hr.

Example 9B

HMF (10 mM), KPi Phosphate buffer (1 mL, 100 mM), KRED CFE (15 mg), were combined with $NADP^+$ (30 mM). Aliquots were removed every hour and quenched with 1M HCl, centrifuged and analysed by RP-HPLC. The results from the reaction can be seen in FIG. 25.

Example 9C

Reaction Conditions: HMF (10 mM), KRED (089) (7.5 mg), 0.5 mL KPi Buffer (pH x), and NOX-1 and $NADP^+$ as defined in Table 7B were reacted at 37° C. for 2 hours. A sample was quenched with 1M HCl, centrifuged and analysed by RP-HPLC. The results from the reaction can be seen in Table 7B.

Using 10 mol % of $NADP^+$ (relative to the amount of HMF used) and 5 mg NOX-1 provided the highest conversion of HMF to 2,5-FDCA. Reducing the amount of NADP+ and NOX-1 lead to a lower conversion of HMF to HMFCA.

TABLE 7B

| Entry | pH | NOX-1 (mg) | NADP+ (mol %)[a] | Conversion HMF:DFF:HMFCA:FFCA:2,5-FDCA |
|---|---|---|---|---|
| 1 | 7 | 5 | 50 | 0:0:23:53:23 |
| 2 | 7 | 7.5 | " | 0:0:28:54:17 |
| 3 | 7 | 10 | " | 0:0:33:52:15 |
| 4 | 7 | 5 | 10 | 8:0:12:57:29 |
| 5 | 8 | " | " | 13:0:7.5:49:30 |
| 6 | 9 | " | 10 | 20:0:5:46:30 |

[a]mol % relative to amount of HMF used.

Example 10A—Entrapment of PaoABC in SiO$_2$ Hydrogel

Tetramethyl orthosilicate (TMOS) (0.450 g) was placed in a small vial, cooled in an ice bath, and stirred at about 600 rpm. HCl (108 µL, 2.44 mM) was added, and the solution was stirred for 10 min. The solution was adjusted to pH 5.1 by adding 60 µL of 20 mM sodium phosphate buffer (pH 7.4). In a separate small vial, 1 mg of PaoABC, 540 µL of 10 mM 4-(2-hydroxyethyl)-1-piperazineethanesulfonic acid (HEPES) (sodium salt) buffer solution (pH 7.5), and, when polymer was added, 60 µL of 20 mg/mL aqueous PVI or PEI were mixed. The PaoABC-containing solution was added to the TMOS-containing solution, and the resulting mixture was stirred for 1 min. A vacuum was applied to the stirred mixture until a gel formed. The vacuum was released, and the gel was rinsed with 2 mL of distilled water three times. The gel was then soaked in 2 mL of distilled water overnight at 4° C. The water was removed from the vial, and the gel was allowed to dry at room temperature overnight in a vial. The dried gel was first collected and then ground to a powder with a mortar and pestle. 750 mg of hydrogel was produced with 1 mg of PaoABC, as determined by Bradford assay of the supernatant.

Example 10B—Entrapment of PaoABC in Ni-Sepharose 30 mL binding buffer (400 mM NaCl, 20 mM Imidazole, 50 mM KPi pH 7.0), 3 g of PaoABC CFE and 5 g Ni$^{+2}$ 5 g of resin was stirred for 40 minutes. The slurry was centrifuged at 500 RPM and the supernatant removed. This was repeated twice with washing with binding buffer.

Example 10C—Entrapment of PaoABC in Eupergit EC

35 µl of PaoABC was dissolved in 1 mL 1M KPi buffer with a pH as specified in Table 8. The concentration of PaoABC before immobilisation was recorded. 10 mg of Eupergit EC was added and the mixture was left in a shaking incubator at 150 rpm and 25° C. for 24 hours. The amount of enzyme absorbed onto the resin was determined by UV spectroscopy (428 nm). Blocking buffer (0.2M ethanolamine in 0.1 M KPi pH 7) was added and the mixture was left to shake for 30 minutes. The immobilised enzyme was filtered through a sinter funnel and washed with KPi buffer pH 7 and then KPi buffer pH 7 with 1M NaCl. The immobilised beads were tested for activity.

TABLE 8

| Entry | Immobilisation pH | Enzyme (mg/mL) | Enzyme Immobilized (mg) | Conversion[a] (%)[b] |
|---|---|---|---|---|
| 1 | 6 | 0.85 | 0.7 | 44 |
| 2 | 7 | 1 | 0.97 | 48 |
| 3 | 8 | 0.94 | 0.8 | 60 |

[a]Reaction conditions: 0.1 mg PaoABC (on resin), 2.5 µl benzaldehyde, 500 µl 100 mM KPi pH 7.6, 37° C., 5 Hr
[b]Conversion calculated by RP-HPLC Example 10D—Entrapment of PaoABC in Eupergit CM 70 µL (2 mg) of paoABC was dissolved in 1 mL 1M KPi buffer pH 7. The concentration before immobilisation was recorded. 200 mg of Eupergit EC was added and left in a shaking incubator on 150 rpm at 25° C. for 24 Hr. The amount of enzyme absorbed onto the resin was determined by UV spectroscopy (428 nm). After this time the pH was increased to pH 8.5 to facilitate multipoint attachment to the resin (5 hr). Blocking buffer (3M Glycine pH 8.5) was added and left shake for 5 hours. The immobilised enzyme was filtered through a filter paper and washed with 100 mM KPi Buffer pH 7 and, 100 mM KPi buffer pH 7 with 1M NaCl. The immobilised beads were tested for activity.

| Entry | Resin | Amount | Run | Conversion (%) |
|---|---|---|---|---|
| 1 | Eupergit CM | 50 mg | 1 | 100 |
| 2 | " | " | 2 | 100 |

Reaction conditions: 100 mM KPi phosphate buffer pH 7.0, 100 mM DFF, 5 hr, 37° C.

Example 11—Formation of 2,5-FDCA from DFF Using Immobilised PaoABC

To 300 µL of 0.3M TrisHCl pH 7.0, was added 5 mg of catalase-CLEA (catalase cross-linked enzyme aggregates) and 0.065 mg of immobilized PaoABC (50 mg of hydrogel, 10 mg for Eupergit-immobilised PaoABC, 2.2 µL of soluble PaoABC (29.2 mg/mL)) in a 1.5 mL Eppendorf. The reaction was vigorously shaken and the pH adjusted to pH 7.0. DFF (1.9 mg; 50 mM) was added and the reaction was placed in a shaking incubator at 25° C. 5 µL of the reaction mixture was extracted and diluted with 80 µL of water and 15 µL of 1M HCl before being centrifuged for 5 mins. The aliquots were analysed by reverse phase HPLC.

The hydrogel could be used 14 times with no loss in activity.

Example 12

Synthesis of 2,5-diethyl-2,5-furandicarboxylate

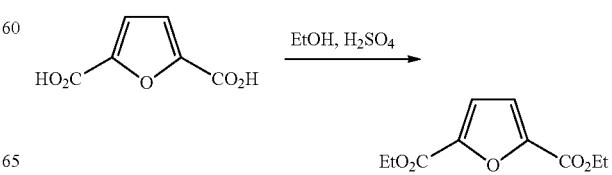

2,5-furandicarboxylic acid (25.18 g; 160 mmol) was added to ethanol (1,800 mL). Aqueous sulfuric acid (1.32 mL) was added. The mixture was heated at reflux (about 78° C.) for 67 hours, during which time water was removed from the reaction by the use of a Dean-Stark apparatus. The reaction progress was monitored using NMR spectroscopy. After the 2,5-diethyl-2,5-furandicarboxylate had been formed in >97% purity by NMR, the reaction mixture was allowed to cool to ambient temperature and was extracted with 2-methyltetrahydrofuran. The combined organic layers were washed with a saturated aqueous brine solution and deionised water, and dried ($MgSO_4$). The organics were filtered and the volatiles were removed in vacuo to afford the title compound (26.77 g; 130 mmol; >98% conversion).

General Methodology for the Formation of Copolymers

A 250 mL flange flask with 5 quick-fit ports was used in connection with a Dean-Stark apparatus. Stirring was achieved via a magnetic stirrer using a large precious metal stirrer bar. The rates of stirring were gradually decreased from the initial 400 rpm down to 200 rpm to avoid issues as a result of the increasing viscosity of the reaction mixture. All reagents were added to the reactor and warmed to 110 to 130° C. as described below to allow total melting and achieve miscibility. A flow of $N_2$ gas was applied for 20 minutes to purge the reagents and reactor of oxygen. The temperature was then increased to the desired point as stated below. After a further four hours of very low $N_2$ flow the gas line was removed, the Dean-Stark drained and a vacuum pump turned on, initially at a low vacuum (~200 mbar) but slowly increased as stated below.

Example 13

Synthesis of 2,5-polybutyrate Adipate Furandicarboxylate (2,5-PBAF)

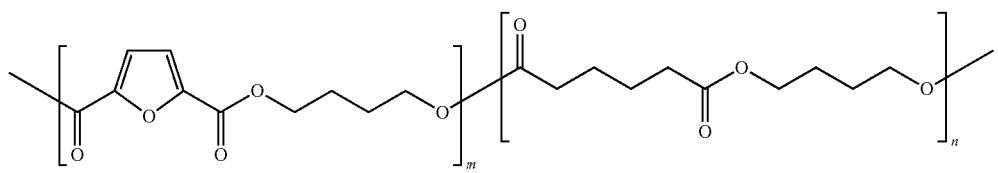

Figure 1:
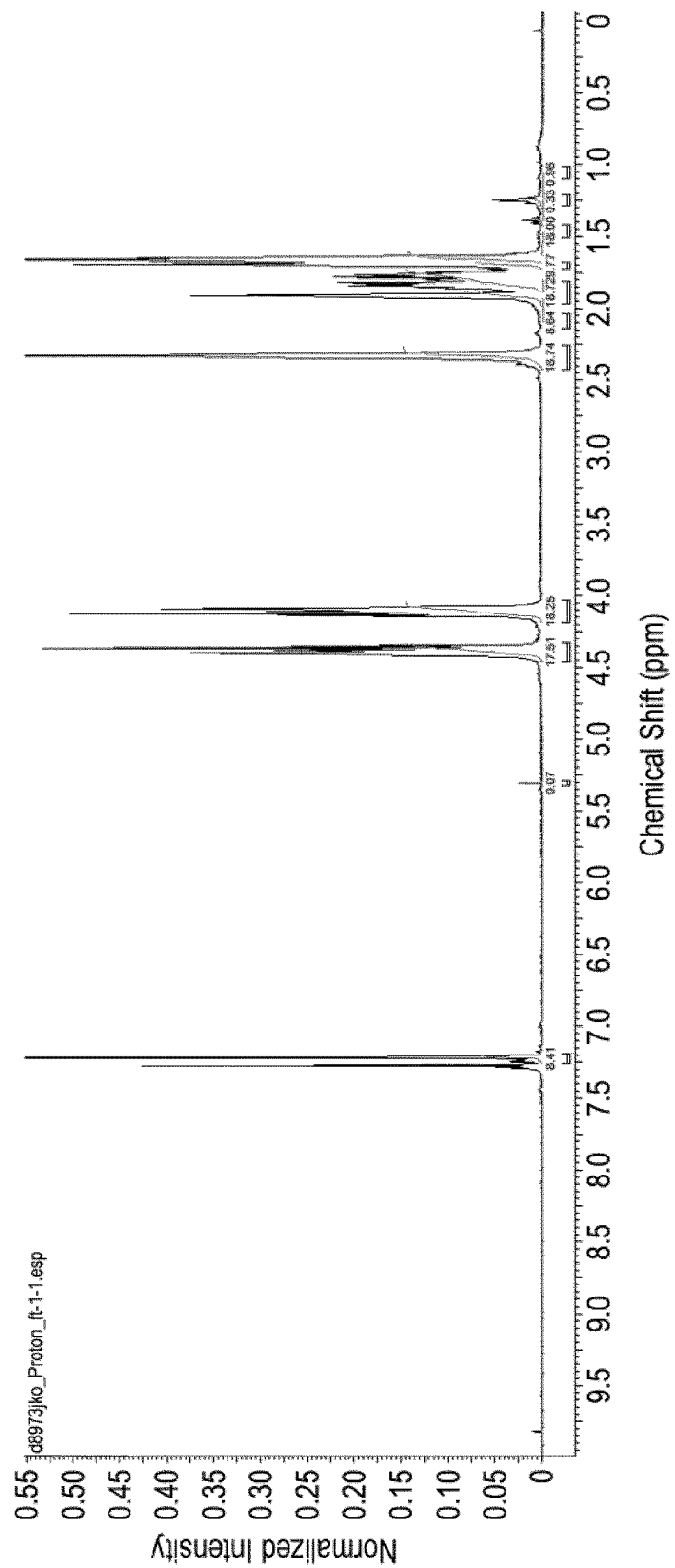
FIG. 1 shows the $^1$H NMR spectra for 2,5-polybutyrate adipate furandicarboxylate (2,5-PBAF), i.e. a copolymer of the invention.

2,5-Diethyl-2,5-furandicarboxylate (21.20 g; 100 mmol), diethyl adipate (20.23 g; 100 mmol), 1,4-butane diol (22.53, 250 mmol) and T titanium(IV) tert-butoxide (0.77 mL; cat.) were combined. The reaction mixture was heated at 110° C. for 4 hours at atmospheric pressure with stirring at 400 rpm, 180° C. for 17 hours at 200 mbar and 350 rpm, and at 180° C. for 3 hours at 25 mbar and 250 rpm. The polymer was formed (37.20 g). The $^1$H NMR spectra for 2,5-PBAF can be found at FIG. 1.

The molar ratio of 2,5-furandicarboxylate:adipate was determined by $^1$H NMR to be 0.90:1. The molecular weight of the 2,5-PBAF was estimated using end-group analysis, wherein the ratio of end groups to those of the bulk polymer were calculated using $^1$H NMR to give the number of constitutional repeating units (CRU), which was estimated to be 20.71. One ideal CRU is 410.43 gmol$^{-1}$. Therefore, the molecular weight of the 2,5-PBAF was estimated to be 8,497.5 gmol$^{-1}$.

Comparative Example 14

Synthesis of Polybutyrate Adipate Terephthalate (PBAT)

Figure 2:
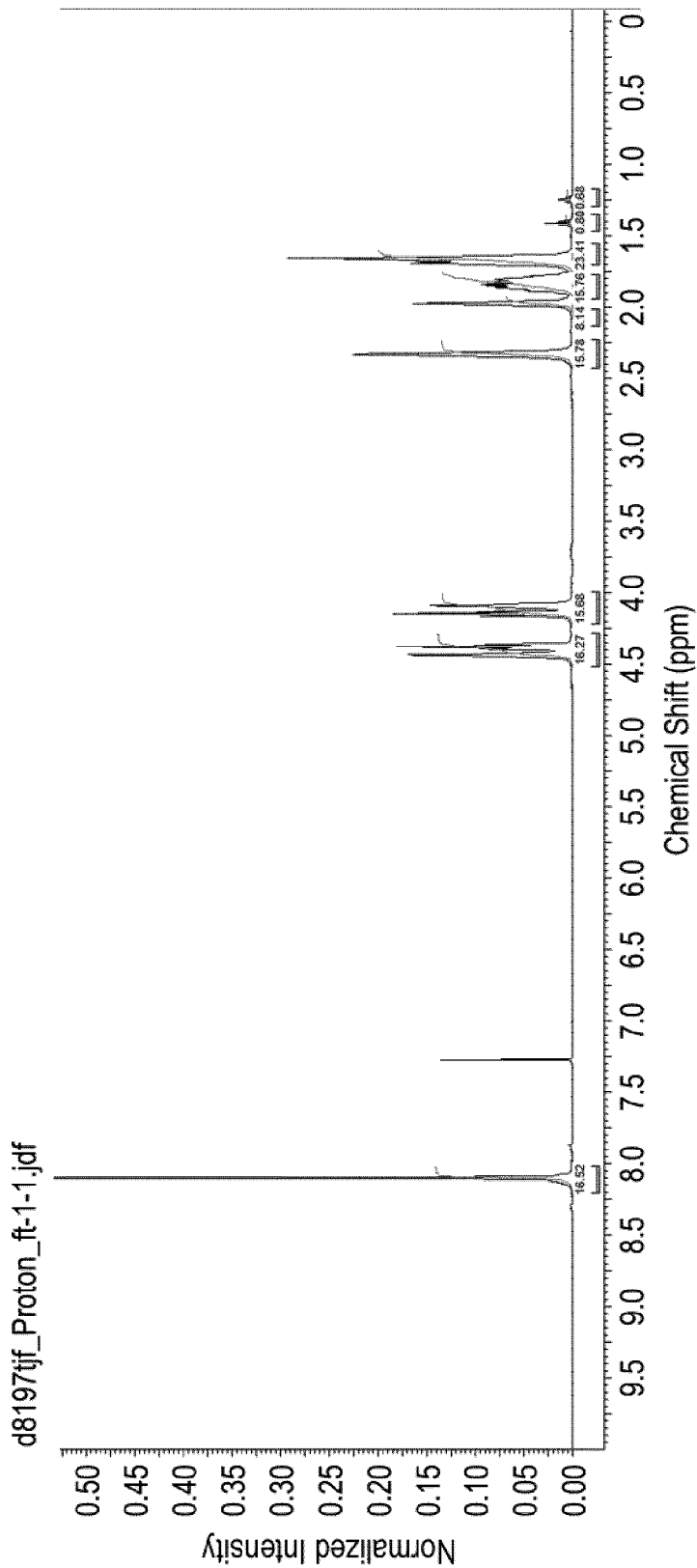
FIG. 2 shows the 1H NMR spectra for polybutyrate adipate terephthalate (PBAT) (Comparative Example 14).

Diethyl terephthalate (22.22 g; 100 mmol), diethyl adipate (20.23 g; 100 mmol), 1,4-butane diol (22.73, 230 mmol) and titanium(IV) tert-butoxide (0.77 mL; cat.) were combined. The reaction mixture was heated at 130° C. for 2 hours at atmospheric pressure with stirring at 400 rpm, 180° C. for 2 hours at atmospheric pressure and 400 rpm, 180° C. for 17 hours at 200 mbar and 350 rpm, and at 180° C. for 3 hours at 25 mbar and 250 rpm. The copolymer was formed (40.51 g). The $^1$H NMR spectra for PBAT can be found at FIG. 2.

The molecular weight of the PBAT was estimated by $^1$H NMR using end-group analysis as described for 2,4-PBAP. The molar ratio of terephthalate:adipate was determined to be 1.047:1. The number of CRUs was estimated to be 16.4. One ideal CRU is 420.45 gmol$^{-1}$. Therefore, the molecular weight of the PBAT was estimated to be 6,893 gmol$^{-1}$.

Figure 3:
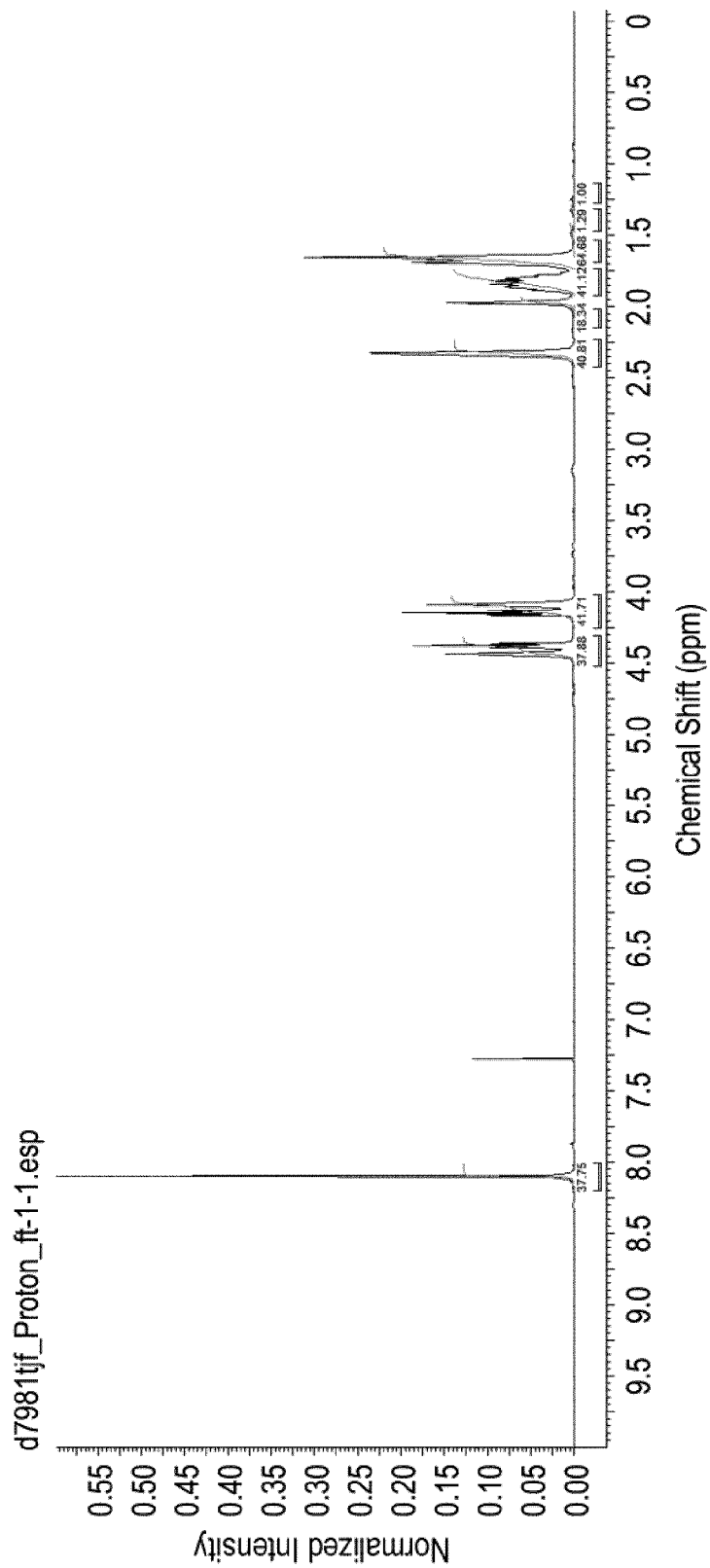
FIG. 3 shows the $^1$H NMR spectra for commercial PBAT.

PBAT is available commercially under a range of trade names. The molecular weight of one particular commercial PBAT was estimated by $^1$H NMR using end-group analysis as described for 2,4-PBAP. The molar ratio of terephthalate: adipate was determined to be 0.93:1. The number of CRUs was estimated to be 25.7. One ideal CRU is 420.45 gmol$^{-1}$. Therefore, the molecular weight of the commercial PBAT was estimated to be 10,809 gmol$^{-1}$. The $^1$H NMR spectra for commercial PBAT can be found at FIG. 3.

Example 15

Thermal Analysis of Polymers Using (STA and DSC)

The thermal stability of cured copolymer was analysed using Simultaneous Thermal Analysis (STA) using a Stanton Redcroft STA 625. Approximately 10-20 mg of copolymer was heated from ambient temperature to 625° C. at a heating rate of 10° C. min$^{-1}$ under nitrogen. The decomposition may be that of the copolymer backbone. The results can be found in Table 9.

TABLE 9

STA analysis of polymers

Figure 4:
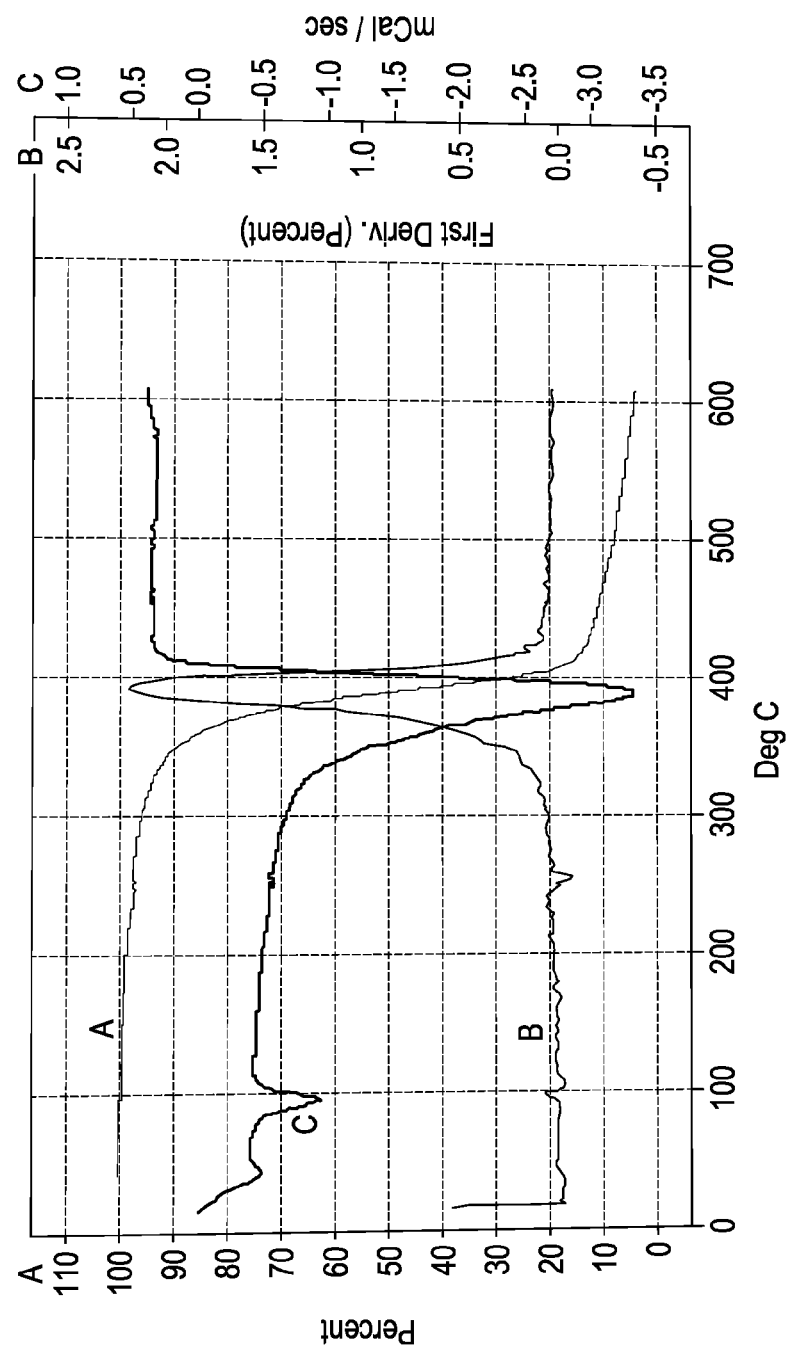
FIG. 4 shows the Simultaneous Thermal Analysis (STA) trace for 2,5-PBAF.
Figure 5:
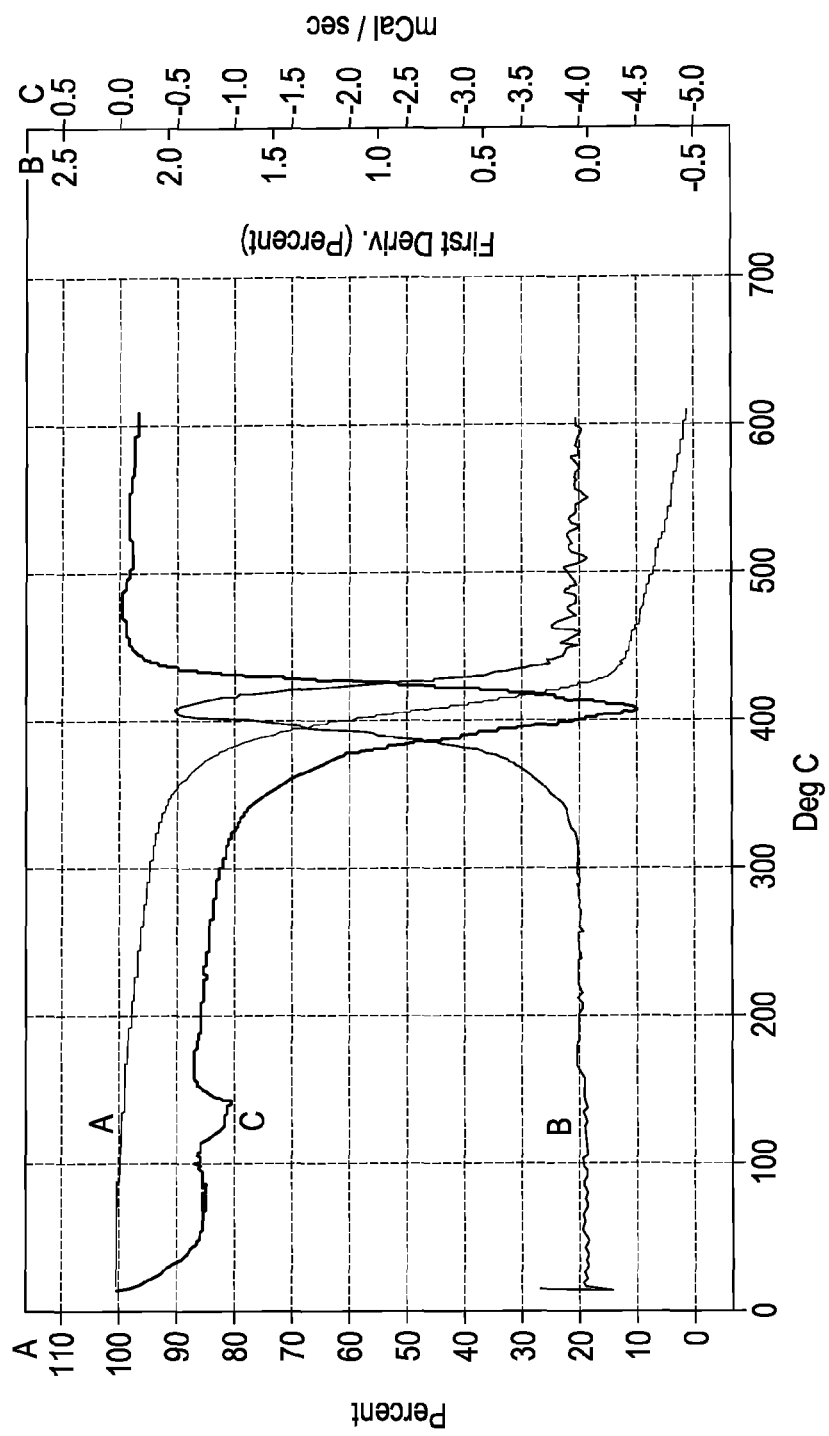
FIG. 5 shows the STA trace for PBAT (Comparative Example 14).
Figure 6:
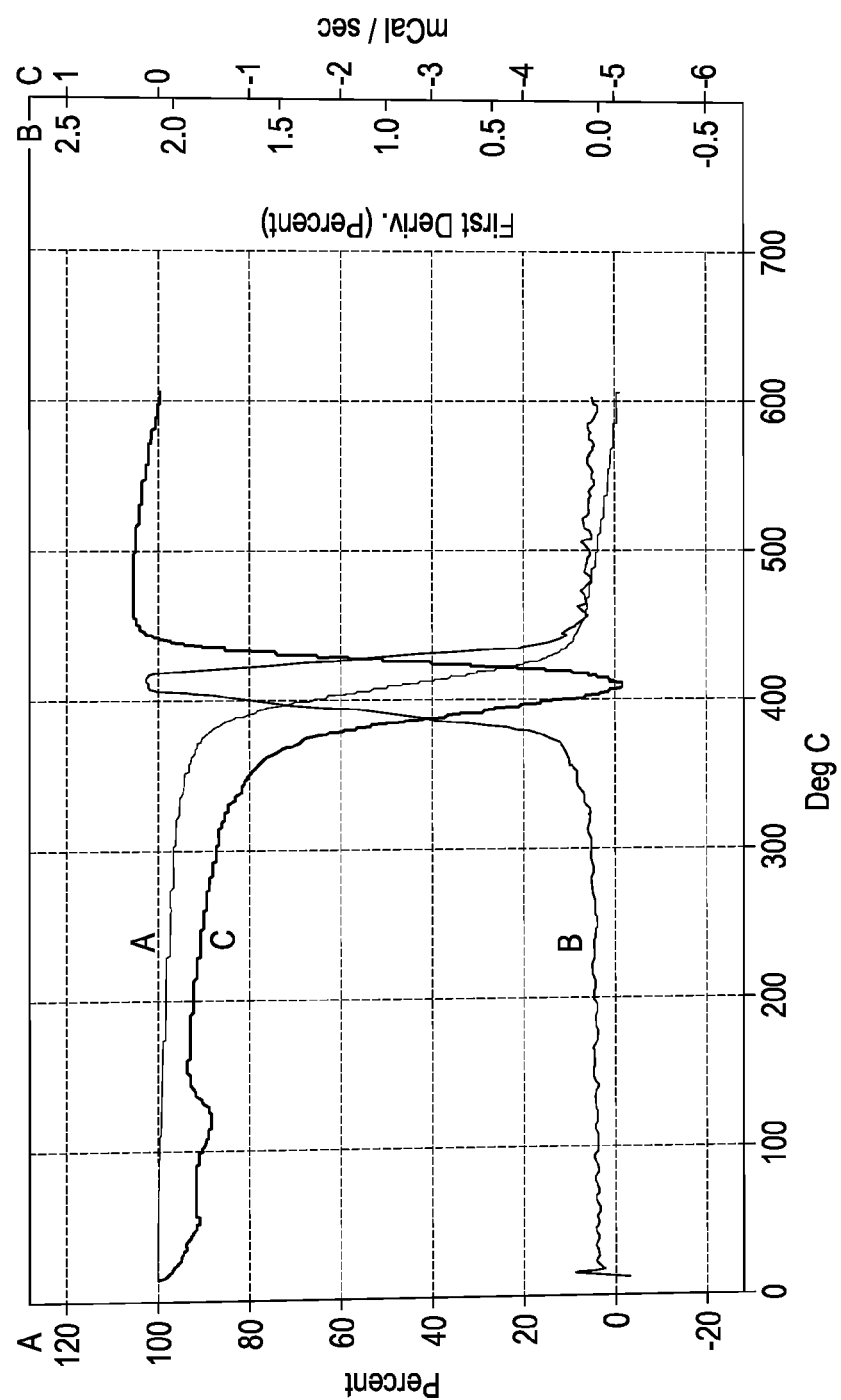
FIG. 6 shows the STA trace for commercial PBAT.

| Copolymer | Temperature of 5 wt % loss ° C. | Temperature of decomp. ° C. | STA trace |
|---|---|---|---|
| 2,5-PBAF | 315.0 | 391.7 | FIG. 4 |
| Comparative Example 14 | 289.5 | 406.0 | FIG. 5 |
| Commercial PBAT | 341.5 | 409.5 | FIG. 6 |

The glass transition temperature ($T_g$) and melting point ($T_m$) of the copolymers were obtained by Differential Scanning calorimetry (DSC) analysis using a TA Instruments Q2000 DSC. Indium was used as the standard to calibrate the temperature and heat capacity. Copolymer samples (7-10 mg) were sealed in Tzero aluminum hermetic DSC pans.

Figure 7:
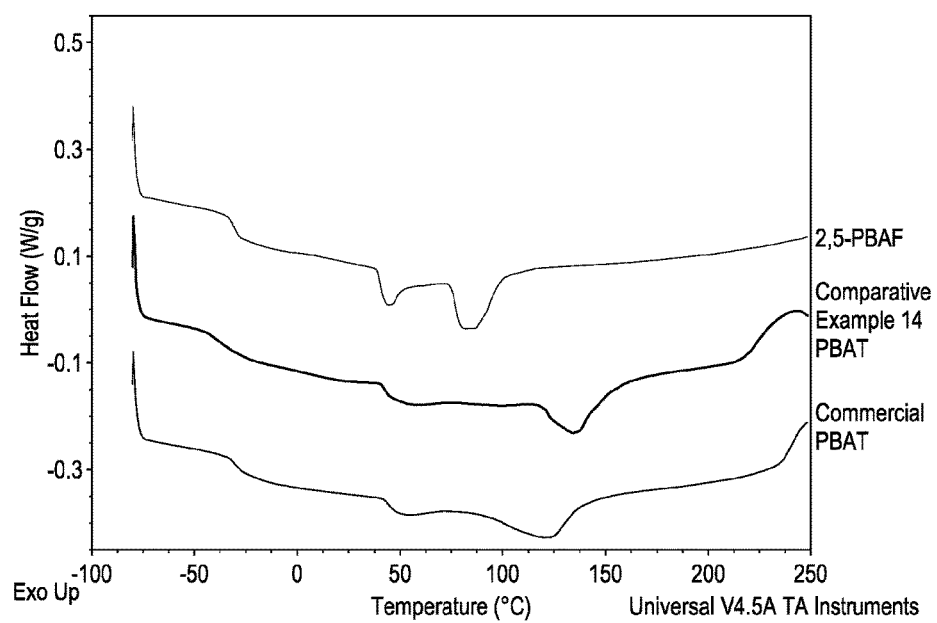
FIG. 7 shows Differential Scanning calorimetry (DSC) traces for 2,5-PBAF, PBAT (Comparative Example 14) and commercial PBAT.

The method was carried out under a constant flow of dry nitrogen of 50 mL/min, at 10° C./min over a temperature range of −80° C. to 250° C. The results can be found in Table 10. The DSC traces can be found at FIG. 7.

TABLE 10

DSC analysis of copolymers

| Copolymer | $T_{g1}$ °C. | $T_{g2}$ °C. | $T_m$ °C. |
|---|---|---|---|
| 2,5-PBAF | −30.4 | 40.5 | 87.2 |
| Comparative Example 14 | −39.5 | 42.4 | 134.6 |
| Commercial PBAT | −30.1 | 45.4 | 122.2 |

Example 16

The molecular weight ($M_n$ and $M_w$) and polydispersity ($Pd_i$) data as generated by GPC can be found in Table 11. GPC was conducted on an Agilent SECurity GPC System 1260 Infinity using THF as the solvent, a polystyrene standard, and a light scattering detector.

TABLE 11

GPC analysis of copolymers

Figure 8:
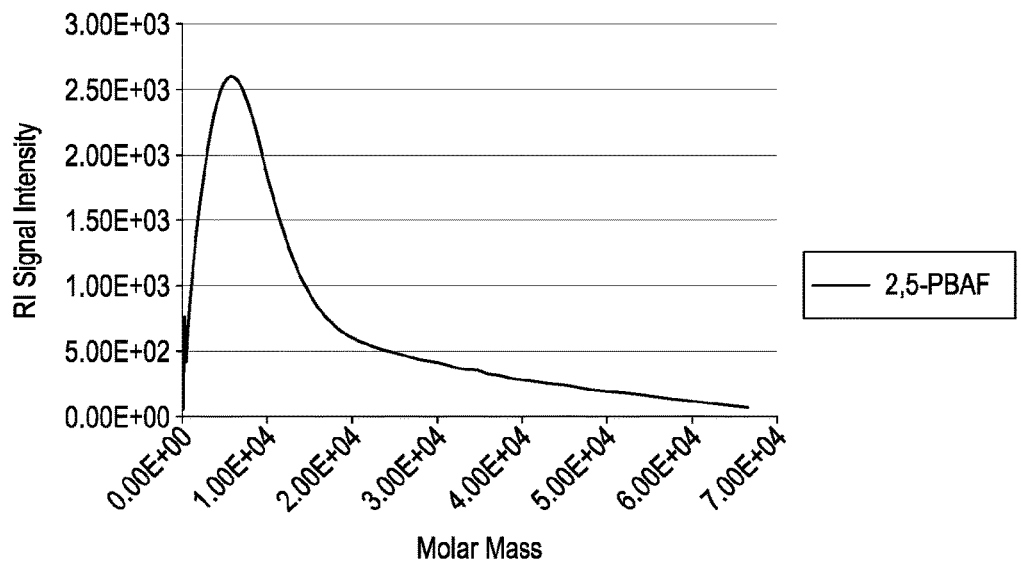
FIG. 8 shows the Gel Permeation Chromatography (GPC) spectra for 2,5-PBAF.
Figure 9:
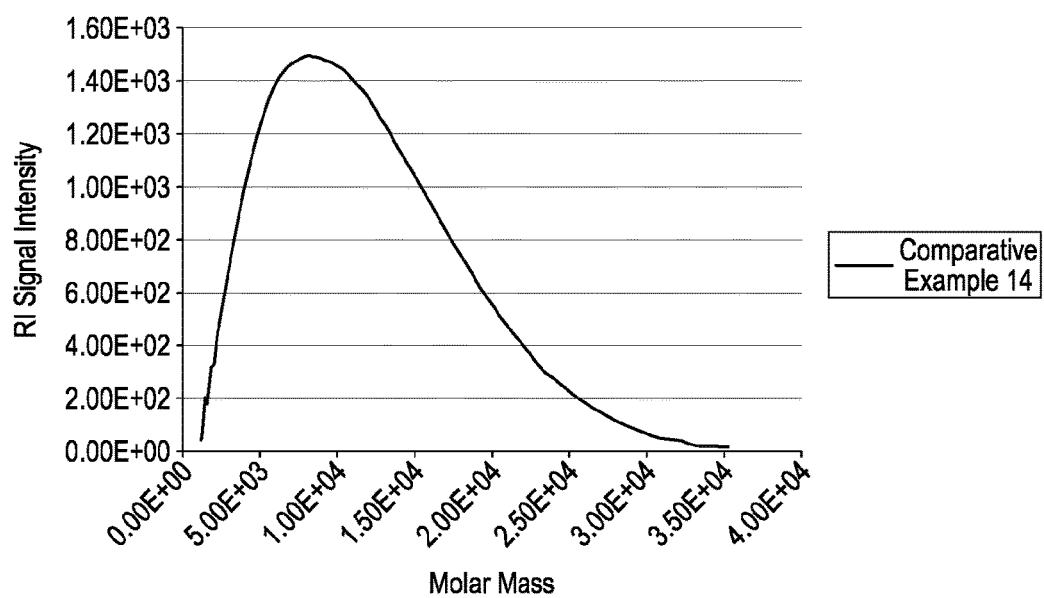
FIG. 9 shows the GPC spectra for PBAT (Comparative Example 14).
Figure 10:
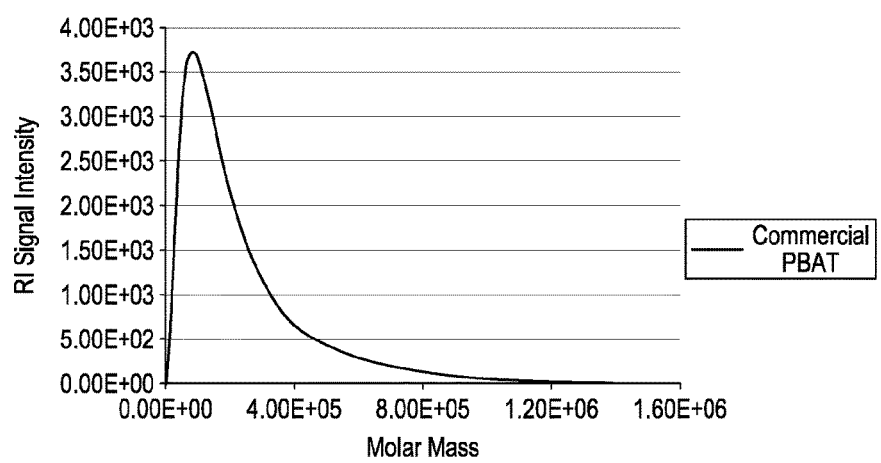
FIG. 10 shows the GPC spectra for commercial PBAT.

| Copolymer | $M_n$ | $M_w$ | $Pd_i$ | GPC chromatogram |
|---|---|---|---|---|
| 2,5-PBAF | 862.5 | 6,121 | 7.097 | FIG. 8 |
| Comparative Example 14 | 5,582 | 8,615 | 1.544 | FIG. 9 |
| Commercial PBAT | 42,190 | 113,100 | 2.680 | FIG. 10 |

Example 17

Tensile Strength Measurement

Mechanical properties including tensile strength, elongation at break and Young's modulus of samples are summarised in Table 12. Film samples were prepared by heating about 8 g of copolymer in a fan-assisted oven at 160° C. for 15 min (180° C. for PBAT). The resulting films were cut into standard dumb-bell shapes (60 mm×10 mm). Film thickness was in the region of 1.5-2.0 mm. Tensile studies were conducted in triplicate using an Instron 3367 universal testing machine fitted with 1000 N capacity load cell. The initial grip separation was set at 35 mm and the crosshead speed was 20 mm/min. The results reported were the average of the three measurements (the elongation at break was obtained automatically from the software). Commercially PBAT is a typical elastomer with elongation over 293%. It has the highest tensile strength over 19.5 MPa and good Young's modulus of 100.8 MPa.

TABLE 12

Tensile strength measurement of copolymers

| Copolymer | Tensile strength MPa | Elongation at break % | Young's Modulus MPa |
|---|---|---|---|
| 2,5-PBAF | 2.2 ± 0.4 | 4.7 ± 0.8 | 75.3 ± 2.0 |
| Comparative Example 14 | 4.8 ± 0.5 | 2.3 ± 0.2 | 269.8 ± 0.2 |
| Commercial PBAT | >19.5 | >293.1 | 100.8 |

The 2,5-PBAF copolymer produced is soft like that of the commercial PBAT. The expected ratio of FDCA to adipate of about 1:1 has been incorporated into the copolymer. The observed molecular weight of 2,5-PBAF and comparative example 14 (PBAT) are significantly lower than that of commercial PBAT. This is expected given the relatively small scale on which the copolymerisations were conducted and will be higher in a full scale production process. The NMR data provides an indication of the relative number of constitutional repeating units (CRU) and hence an indication of molecule weight, though the GPC provides more accurate values.

The differences in the data obtained for the copolymers of the invention and the commercial BPAT may be attributed to a lack of branching in 2,5-PBAF.

Example 18

Stabilised green waste compost is matured in a composting bin under controlled aeration conditions. Before use, the mature compost is sieved on a screen of 5 mm. The fine fraction forms the inoculum with a total solids content of approximately 50-55% and the volatile content of the total solids is more than 30%.

The standard and control materials are mixed with the inoculum in a ratio of approximately 1 to 1.5 parts of total solids to 6 parts of total solids and introduced into a reactor. These reactors are closed and put into an incubator. The temperature of the reactors is maintained at 58° C.+/−2° C. Pressurised air is pumped through a gas flow controller and blown into the composting vessel at the bottom through a porous plate. During biodegradation, solid carbon of the test sample is converted into $CO_2$.

The gas leaving each individual reactor is analysed at regular intervals for $CO_2$ and $O_2$ concentrations. As the flow rate is continually measured, the cumulative $CO_2$ production can be determined. The percentage of biodegradation is determined as the percentage of solid carbon of the test compound that is converted into $CO_2$.

Those skilled in the art will recognise or be able to ascertain using no more than routine experimentation many equivalents to the specific embodiments described herein. The scope of the present embodiments described herein is not intended to be limited to the above description, but rather is as set forth in the appended claims. Those of ordinary skill in the art will appreciate that various changes and modifications to this description may be made without departing from the spirit or scope of the present invention, as defined in the following claims.

The invention claimed is:

1. A process for the formation of furandicarboxylic acid (FDCA) from hydroxymethylfurfural (HMF), said process comprising the steps of
   (i) providing hydroxymethylfurfural, and
   (ii) (a) adding xanthine oxidoreductase (XOR) and/or galactose oxidase variant $M_{3-5}$ (GOase $M_{3-5}$), or
   (b) adding galactose oxidase variant $M_{3-5}$ (GOase $M_{3-5}$), periplasmic aldehyde oxidase (PaoABC), and horseradish peroxidase (HRP) to the hydroxymethylfurfural, or
   (c) adding galactose oxidase variant $M_{3-5}$ (GOase $M_{3-5}$), periplasmic aldehyde oxidase (PaoABC), and a metal complex to the hydroxymethylfurfural, or
   (d) adding galactose oxidase variant $M_{3-5}$ (GOase $M_{3-5}$), aldehyde dehydrogenase (ALD), nicotinamide oxidase (NOX) and either nicotinamide adenine dinucleotide phosphate ($NADP^+$) or nicotinamide adenine dinucleotide ($NAD^+$) to the hydroxymethylfurfural provided in step (i), or (e) adding aldehyde dehydrogenase (ALD), nicotinamide oxidase (NOX) and either nicotinamide adenine dinucleotide phosphate (NADP⁺) or nicotinamide adenine dinucleotide (NAD⁺) to the hydroxymethylfurfural provided in step (i), or (f) adding ketoreductase (KRED), and either nicotinamide adenine dinucleotide phosphate (NADP⁺) or nicotinamide adenine dinucleotide (NAD⁺).

2. The process of claim 1, wherein, in step (ii)(a), the process comprises the addition of xanthine oxidoreductase (XOR) and galactose oxidase variant M$_{3-5}$ (GOase M$_{3-5}$).

3. The process as claimed in claim 1, wherein, in step (ii)(a), the xanthine oxidoreductase is selected from the group consisting of *E. coli* XDH, *Rhodococcus capsulatus* xanthine dehydrogenase (XDH) single variant E232V, and double mutant XDH E232 V/R310, and periplasmic aldehyde oxidase (PaoABC).

4. The process as claimed in claim 1, wherein, in steps (i) and (ii), the process comprises the steps of
   (i) converting hydroxymethylfurfural (HMF) into formylfurancarboxylic acid (FFCA); and
   (ii) converting formylfurancarboxylic acid into furandicarboxylic acid (FDCA), wherein steps (i) and (ii) are carried out in the presence of xanthine oxidoreductase (XOR) and galactose oxidase variant M$_{3-5}$ (GOase M$_{3-5}$).

5. The process as claimed in claim 1, wherein, in step (i) and (ii), the process comprises the steps of
   (i) providing hydroxymethylfurfural;
   (ii) adding galactose oxidase variant M$_{3-5}$ (GOase M$_{3-5}$) to the hydroxymethylfurfural provided in step (i) to convert the hydroxymethylfurfural to diformyl furan (DFF); then
   (iii) adding periplasmic aldehyde oxidase (PaoABC) to the diformyl furan in step (ii) to convert the diformyl furan to furandicarboxylic acid via formylfurancarboxylic acid (FFCA).

6. A process for the formation of furandicarboxylic acid (FDCA) from diformyl furan (DFF) comprising the steps of
   (i) providing diformyl furan, and
   (ii) (a) adding aldehyde dehydrogenase (ALD), nicotinamide oxidase (NOX) and either nicotinamide adenine dinucleotide phosphate (NADP⁺) or nicotinamide adenine dinucleotide (NAD⁺) to the diformyl furan provided in step (i), or
   (b) adding periplasmic aldehyde oxidase (PaoABC), catalase and H$_2$O$_2$, or
   (c) adding immobilised periplasmic aldehyde oxidase (PaoABC).

7. A process for the formation of formylfurancarboxylic acid (FFCA) from hydroxymethylfurfural (HMF), said process comprising the steps of
   (i) providing hydroxymethylfurfural; and
   (ii) adding ketoreductase (KRED), and either nicotinamide adenine dinucleotide phosphate (NADP⁺) or nicotinamide adenine dinucleotide (NAD⁺).

8. The process as claimed in claim 7, wherein the process comprises adding nicotinamide oxidase (NOX) in step (ii).

9. The process as claimed in claim 7, wherein the process comprises the step of obtaining the hydroxymethylfurfural from glucose and/or fructose.

10. The process as claimed in claim 9, wherein the process comprises the step of obtaining the glucose and/or fructose from lignocellulose.

11. A process for the formation of a mono- or diester of furandicarboxylic acid from furandicarboxylic acid, comprising the step of (i) providing furandicarboxylic acid; and
(ii) adding an alcohol and a catalyst,
wherein the furandicarboxylic acid is obtained by a process as defined in claim 1.

12. The process as claimed in claim 11, wherein the mono- or diester of furandicarboxylic acid is selected from the group consisting of

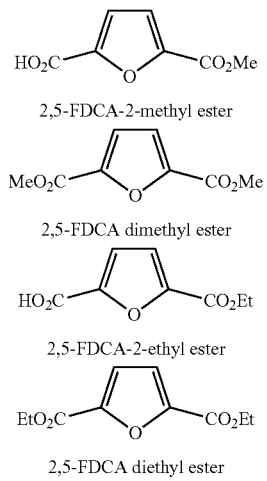

2,5-FDCA-2-methyl ester 2,5-FDCA dimethyl ester 2,5-FDCA-2-ethyl ester 2,5-FDCA diethyl ester and a combination thereof.

13. The process as claimed in claim 11, wherein the catalyst is an organic acid or inorganic acid.

14. The process as claimed in claim 11, wherein the catalyst is sulphuric acid.

15. A process for the formation of a copolymer comprising the copolyester of
   (I) (a) at least one furandicarboxylic acid (FDCA) or a mono- or diester of furandicarboxylic acid,
   (b) at least one diol,
   wherein the process comprises reacting together components (a) and (b) (c), and wherein the furandicarboxylic acid is obtained by a process as defined in claim 1; or
   (II) (a) at least one mono- or diester of furandicarboxylic acid,
   (b) at least one diol, and
   (c) at least one aliphatic dicarboxylic acid or a mono- or diester derivative thereof,
   wherein the process comprises reacting together components (a), (b) and (c), wherein the aliphatic dicarboxylic acid or a mono- or diester derivative thereof is selected from the group consisting of adipic acid, adipic acid monomethyl ester, adipic acid dimethyl ester, adipic acid monoethyl ester, adipic acid diethyl ester, succinic acid, succinic acid monomethyl ester, succinic acid dimethyl ester, succinic acid monoethyl ester, succinic acid diethyl ester, and a combination thereof; or
   (III) (a) at least one mono- or diester of furandicarboxylic acid,
   (b) at least one diol, and
   (c) at least one aliphatic dicarboxylic acid or a mono- or diester derivative thereof,
   wherein the process comprises reacting together components (a), (b) and (c), and wherein the mono- or diester of furandicarboxylic acid is selected from the group consisting of

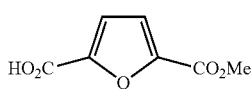

2,5-FDCA-2-methyl ester

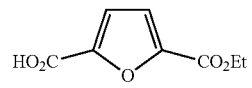

2,5-FDCA-2-ethyl ester

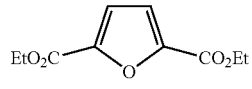

2,5-FDCA diethyl ester and a combination thereof.

16. The process as claimed in claim 15, wherein the copolymer comprises the copolyester of
(a) at least one furandicarboxylic acid (FDCA) or a mono- or diester of furandicarboxylic acid;
(b) at least one diol; and
(c) at least one aliphatic dicarboxylic acid or a mono- or diester derivative thereof.

17. The process as claimed in claim 15 (I), wherein the furandicarboxylic acid or a mono- or diester of furandicarboxylic acid is selected from the group consisting of

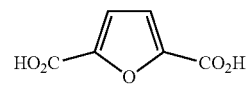

2,5-FDCA

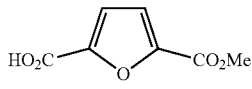

2,5-FDCA-2-methyl ester

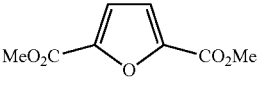

2,5-FDCA dimethyl ester

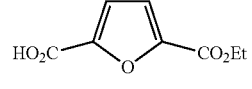

2,5-FDCA-2-ethyl ester

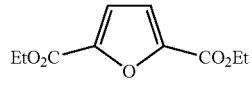

2,5-FDCA diethyl ester and a combination thereof.

18. The process as claimed in claim 15, wherein the aliphatic dicarboxylic acid or a mono- or diester derivative thereof is

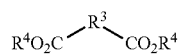

wherein $R^3$ is a straight, branched or cyclic, $C_1$ saturated or $C_2$ to $C_{10}$ saturated or unsaturated alkylene, and wherein each $R^4$ independently represents H or a straight, branched or cyclic, $C_1$ to $C_6$ alkyl group.

19. The process as claimed in claim 15, wherein the aliphatic dicarboxylic acid or a mono- or diester derivative thereof is selected from the group consisting of adipic acid, adipic acid monomethyl ester, adipic acid dimethyl ester, adipic acid monoethyl ester, adipic acid diethyl ester, succinic acid, succinic acid monomethyl ester, succinic acid dimethyl ester, succinic acid monoethyl ester, succinic acid diethyl ester, and a combination thereof.

20. The process as claimed in claim 15, wherein the diol is

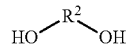

wherein $R^2$ is a straight, branched or cyclic $C_2$ to $C_{10}$ alkylene.

21. The process as claimed in claim 15, wherein the diol is selected from the group consisting of 1,2-ethanediol, 1,4-butanediol, and a combination thereof.

22. The process as claimed in claim 15, wherein the copolymer comprises the copolyester of
(1) (A) furandicarboxylic acid diethyl ester;
(B) 1,4-butanediol; and
(C) adipic acid dimethyl ester or diethyl ester; or
(2) (A) furandicarboxylic acid dimethyl ester or diethyl ester;
(B) 1,4-butanediol; and
(C) adipic acid dimethyl ester or diethyl ester; or
(3) (A) furandicarboxylic acid (FDCA) or a mono- or diester of furandicarboxylic acid; and
(B) 1,2-ethanediol, 1,4-butanediol, or a combination thereof; or
(4) (a) from 1 to 98 mol % of at least one furandicarboxylic acid or a mono- or diester of furandicarboxylic acid;
(b) from 1 to 98 mol % of at least one diol; and
(c) when present, from 1 to 98 mol % of at least one aliphatic dicarboxylic acid or a mono- or diester derivative thereof.

23. The process as claimed in claim 1, wherein step (ii)(f) comprises adding nicotinamide oxidase (NOX).

24. The process as claimed in claim 1, wherein the process comprises the step of obtaining the hydroxymethylfurfural from glucose and/or fructose.

25. A process for the formation of a mono- or diester of furandicarboxylic acid from furandicarboxylic acid, comprising the step of
(i) providing furandicarboxylic acid; and
(ii) adding an alcohol and a catalyst,
wherein the furandicarboxylic acid is produced by a process as defined in claim 6.

26. The process as claimed in claim 11, wherein the mono- or diester of furandicarboxylic acid is selected from the group consisting of

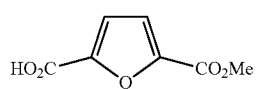

2,5-FDCA-2-methyl ester

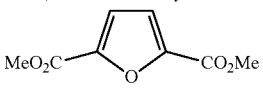

2,5-FDCA dimethyl ester

-continued

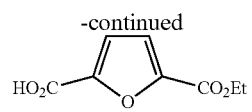

2,5-FDCA-2-ethyl ester

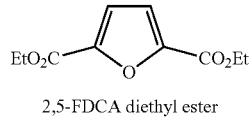

2,5-FDCA diethyl ester and a combination thereof.

27. The process as claimed in claim 11, wherein the catalyst is an organic acid or inorganic acid.

28. The process as claimed in claim 11, wherein the catalyst is sulphuric acid.

29. The process as claimed in claim 15 (II), wherein the furandicarboxylic acid or a mono- or diester of furandicarboxylic acid is selected from the group consisting of

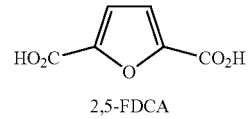

2,5-FDCA

-continued

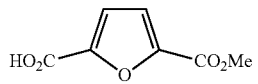

2,5-FDCA-2-methyl ester

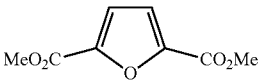

2,5-FDCA dimethyl ester

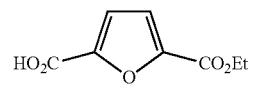

2,5-FDCA-2-ethyl ester

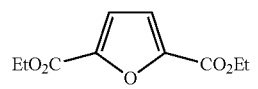

2,5-FDCA diethyl ester and a combination thereof.

30. The process as claimed in claim 15, wherein the diol is a heteroaromatic diol or aromatic diol.

* * * * *